US011293870B2

(12) United States Patent
Mizoguchi et al.

(10) Patent No.: US 11,293,870 B2
(45) Date of Patent: Apr. 5, 2022

(54) VITAL STAIN

(71) Applicant: Mie University, Mie (JP)

(72) Inventors: Akira Mizoguchi, Mia (JP); Takeshi Fujiwara, Mie (JP); Koji Tanaka, Mie (JP); Shujie Wang, Mie (JP); Kousyoku Sai, Mie (JP); Kazushi Kimura, Mie (JP)

(73) Assignee: MIE UNIVERSITY, Mie (JP)

( * ) Notice: Subject to any disclaimer, the term of this patent is extended or adjusted under 35 U.S.C. 154(b) by 103 days.

(21) Appl. No.: 14/780,927

(22) PCT Filed: Mar. 28, 2014

(86) PCT No.: PCT/JP2014/059351
§ 371 (c)(1),
(2) Date: Sep. 28, 2015

(87) PCT Pub. No.: WO2014/157703
PCT Pub. Date: Oct. 2, 2014

(65) Prior Publication Data
US 2016/0041100 A1 Feb. 11, 2016

(30) Foreign Application Priority Data

Mar. 29, 2013 (JP) .............................. JP2013-074953
Mar. 29, 2013 (JP) .............................. JP2013-075150
Mar. 29, 2013 (JP) .............................. JP2013-075256

(51) Int. Cl.
G01N 21/64 (2006.01)
A61B 5/00 (2006.01)
G01N 33/50 (2006.01)
C09B 11/26 (2006.01)
C09B 23/04 (2006.01)
G01N 1/30 (2006.01)

(52) U.S. Cl.
CPC ....... *G01N 21/6486* (2013.01); *A61B 5/0071* (2013.01); *C09B 11/26* (2013.01); *C09B 23/04* (2013.01); *G01N 21/6458* (2013.01); *G01N 33/50* (2013.01); *G01N 1/30* (2013.01); *G01N 2021/6439* (2013.01)

(58) Field of Classification Search
CPC ........... G01N 21/6486; G01N 21/6458; G01N 2021/6439; A61B 5/0071
See application file for complete search history.

(56) References Cited

U.S. PATENT DOCUMENTS

| | | | |
|---|---|---|---|
| 5,862,287 A | 1/1999 | Stock et al. | |
| 2004/0191839 A1 | 9/2004 | Tokunaga | |
| 2008/0045796 A1 | 2/2008 | Yamamoto et al. | |
| 2013/0087724 A1 | 4/2013 | Kuroda | |
| 2014/0010760 A1* | 1/2014 | Giri .................... | A61K 9/1075 424/9.6 |

FOREIGN PATENT DOCUMENTS

| | | |
|---|---|---|
| CN | 101785784 A | 7/2010 |
| CN | 101991588 A | 3/2011 |
| CN | 102256591 A | 11/2011 |
| CN | 102892433 A | 1/2013 |
| JP | 10-186424 H | 1/1999 |
| JP | 2005-501568 A | 3/2003 |
| JP | 2004-313184 | 11/2004 |
| JP | 2005-211355 | 8/2005 |
| JP | 2007-538289 A | 12/2005 |
| JP | 2008-286883 | 11/2008 |
| JP | 2010-8082 | 1/2010 |
| JP | 2012-223104 | 11/2012 |
| WO | WO 00/25665 | 5/2000 |
| WO | 2003/022042 | 3/2003 |
| WO | 2005/116717 | 12/2005 |
| WO | WO 2008/093528 | 8/2008 |
| WO | 2010051641 A1 | 5/2010 |
| WO | 2011122947 A1 | 10/2011 |
| WO | WO 2011/125972 | 10/2011 |
| WO | 2012070041 A1 | 5/2012 |
| WO | WO 2012/078853 | 6/2012 |

OTHER PUBLICATIONS

Ormond et al. "Dye Sensitizers for Photodynamic Therapy" (Mar. 6, 2013), Materials, vol. 6: 817-840. (Year: 2013).*
Yaroslavsky et al. "Fluorescence polarization of tetracycline derivatives as a technique for mapping nonmelanoma skin cancers", 2007, J of Biomedical Optics, vol. 12, No. 1: 1-9 (Year: 2007).*
Oron et al. "Depth-resolved multiphoton polarization microscopy by third-harmonic generation", 2003, Optics Letters, vol. 28, No. 23: 2315-2317. (Year: 2003).*
Fujii et al. Effectiveness of premedication with pronase for improving visibility during gastroendoscopy: a randomized controlled trial, 1998 Gastrointest Endosc 47:382-7. (Year: 1998).*
European Search Report dated Feb. 23, 2017 in corresponding European Patent Application No. 14773865.2.
Kumar et al., Applied Physics Letters, vol. 100, No. 20, May 14, 2012, pp. 203701-1 to 203701-4.
Kunwar et al., Biochimica et Biophysica ACTA (BBA), vol. 1780, No. 4, Dec. 15, 2007, pp. 673-679.
Saab et al., J. Biophotonics, vol. 4, No. 7-8, Mar. 10, 2011, pp. 533-543.
Wilken et al., Molecular Cancer, vol. 10, No. 1, Feb. 7, 2011, p. 12.
Rogart, J. N., et al., Clin Gastroenterol Hepatol Jan. 2008; 6(1): 95-101.
Cruz, J., et al. Biomedical Opticus Express 2010, 1, 5, 1320-1330.
Manabu Ito, "Introduction of 3D cell culture", The Cell, Oct. 20, 2012(Oct. 20, 2012), 44(11): 515-517.

(Continued)

Primary Examiner — Taeyoon Kim
Assistant Examiner — Alexandra F Connors
(74) Attorney, Agent, or Firm — Hunton Andrews Kurth LLP

(57) ABSTRACT

A vital stain for observation under multiphoton laser microscopy, the vital stain comprising one or more edible dye compounds.

1 Claim, 34 Drawing Sheets

(56) References Cited

OTHER PUBLICATIONS

International Search Report dated Jul. 1, 2014 issued in corresponding PCT Application No. PCT/JP2014/059351 [with English Translation].
Hogan,C., Characterization of the interface between normal and transformed epithelial cells, Nature Cell Biology, Mar. 15, 2009, 11, pp. 460-467.
Koji Matsumura, "Development of Methods to Inhibit Tumorigenesis after Transplantation of Differentiated iPS Cells", Cytometry Research, 2011, vol. 21, No. 2, pp. 35 to 41.
Partial Supplementary European Search Report dated Oct. 19, 2016, in corresponding European Application No. 14773865.2.
So, Peter T. C., et. al, Two-Photon Excitation Fluorescence Microscopy, Annual Review of Biomedical Engineering, vol. 2, pp. 399-429, 2000.
Skala, Melissa, et. al, Multiphoton Redox Ratio Imaging for Metabolic Monitoring in Vivo, Methods in Molecular Biology, vol. 594, pp. 155-162, 2009.
Erythrosine, Synonyms, CI Food Red FD&C Red No. C.I, pp. 1-4, 1993.
Roelofs, Theo A., et al, Multiphoton Versus Singel Photon Excitation of Photosensitzers for Laser-Induced Fluorescence Diagnosis and Photodynamic Therapy of Cancer Cells, Optical Sensing II (Proceedings of the SPIE), vol. 4262, pp. 259-262, 2001.
Examination Report from EP Application No. 14773865.2, dated Dec. 20, 2017.
Wong, Linda K. et al, Clinical Considerations of Dimethyl Sulfoxide, Iowa State Veterinarian, vol. 46, No. 2, 1984, pp. 89-95.
Hogan et al., "Characterization of the interface between normal and transformed epithelial cells," Nature Cell Biology, vol. 11(4), Apr. 2009, pp. 460-467.
Pena, A. et al., Three-Dimensional Investigation and Scoring of Extracellular Matrix Remodeling During Lung Fibrosis Using Multiphoton Microscopy, Microscopy Research and Technique, (Feb. 2007), vol. 70, No. 2, pp. 162-170, 9 pages.

\* cited by examiner

FIG. 6A
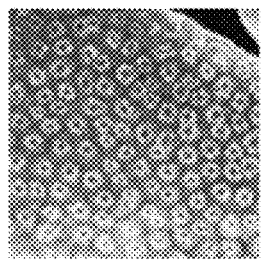
1.Curcumin(turmeric)
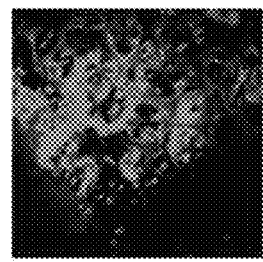
6.Green #3
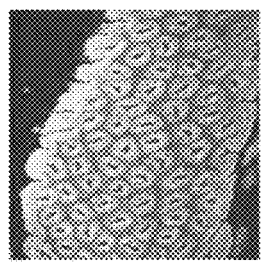
2.Sulfuretin
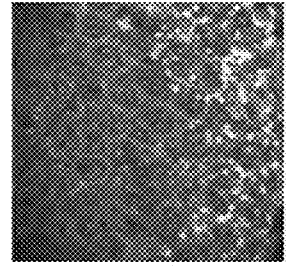
7.Red #2
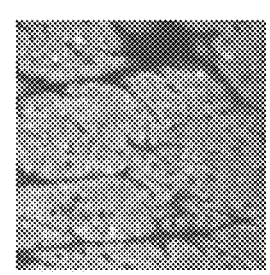
3.Epigallocatechin gallate
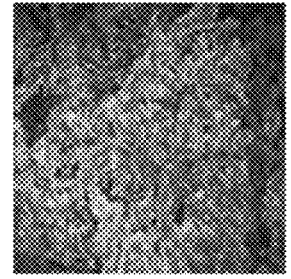
8.Red #102
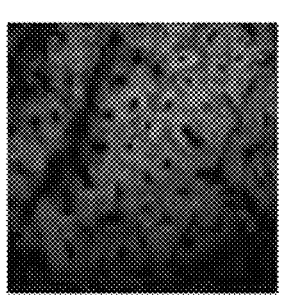
4.Red #3
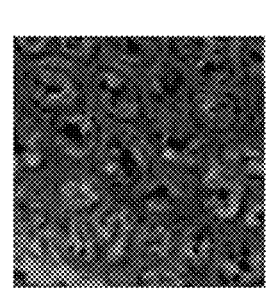
9.Red #104
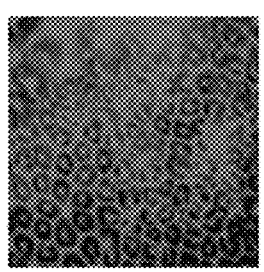
5.Red #106
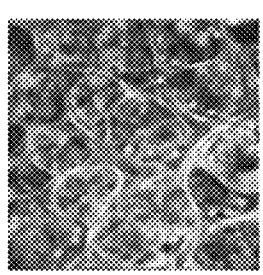
10.Blue #2 indigo carmine FIG. 6B
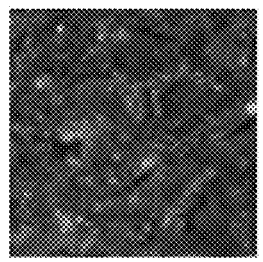
11. Yellow #4
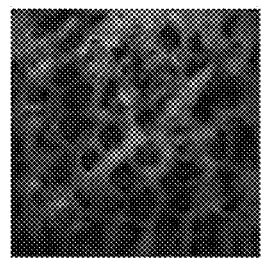
16. Gardenia Yellow pigment
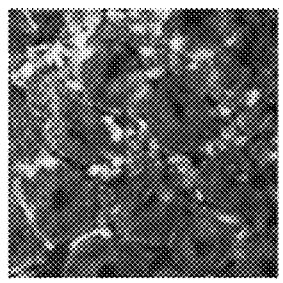
12. Yellow #5
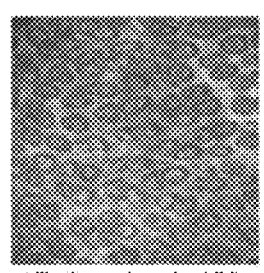
17. Crocin G-150
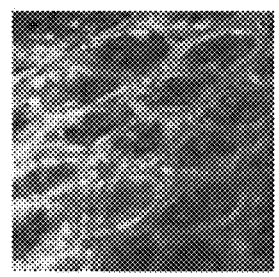
13. Haimeron
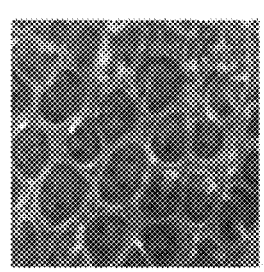
18. Safflomin
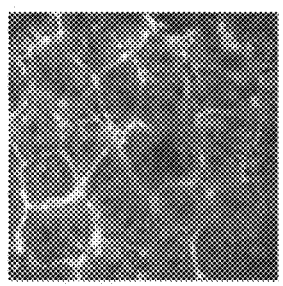
14. Annatto
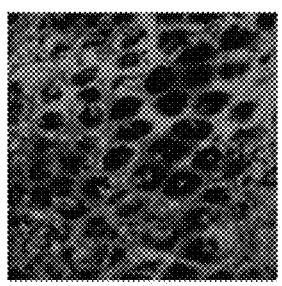
19. HI BLUE-AT
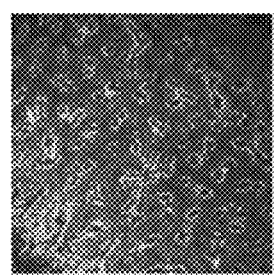
15. Indocyanine green
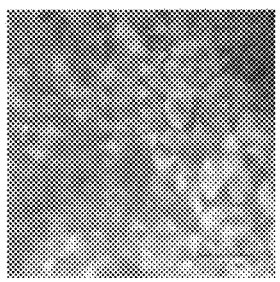
20. Fluorescein FIG. 6C
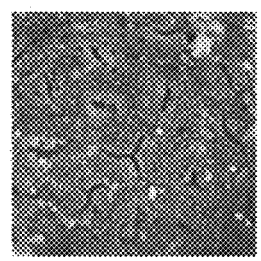
21. Cyanidin (blueberry)
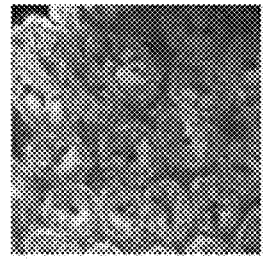
26. Apigeninidin (kaoliang)
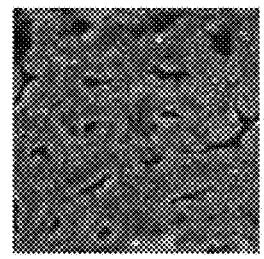
22. Delphinidin (eggplant)
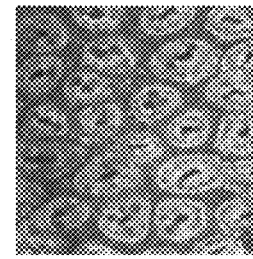
27. Malvidin (grape)
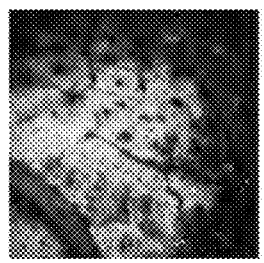
23. Fisetinidin (mangrove)
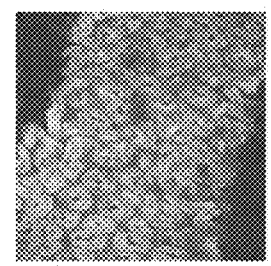
28. β-Carotene
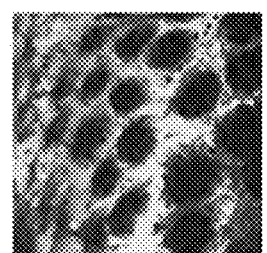
24. Robinetinidin
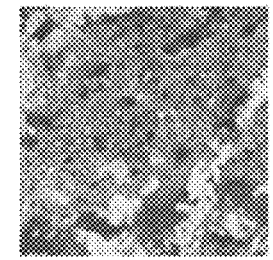
25. Pelargonidin
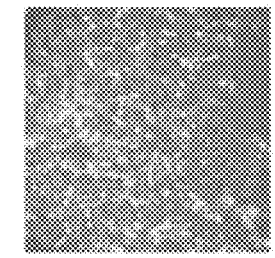
29. HI RED RA 200 (red radish)

FIG. 6D
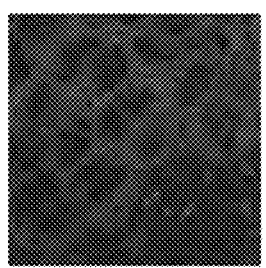
31. HI RED V80 (purple potato)
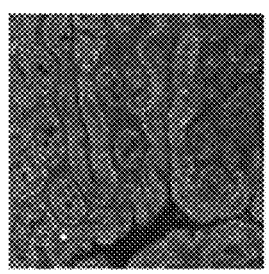
36. Tricetinidin (black tea)
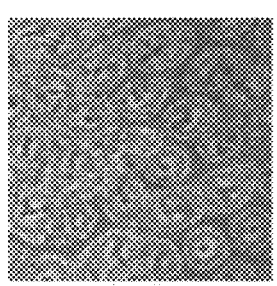
32. HI RED BL (red beet)
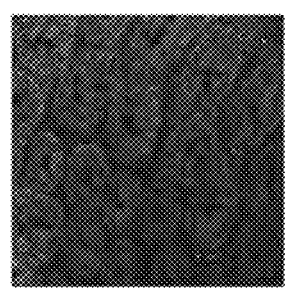
37. Petunidine (red berry)
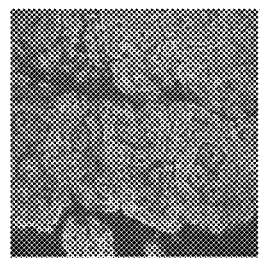
33. 6-Gingerol (ginger)
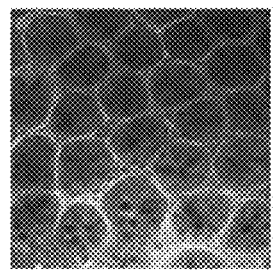
34. Quercetin (onion)
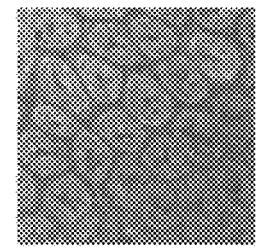
35. Myricetin (onion)

FIG. 21B
H1 RED V80 purple potato dye (cyanidin acyl glycoside and peonidin acyl glycoside)
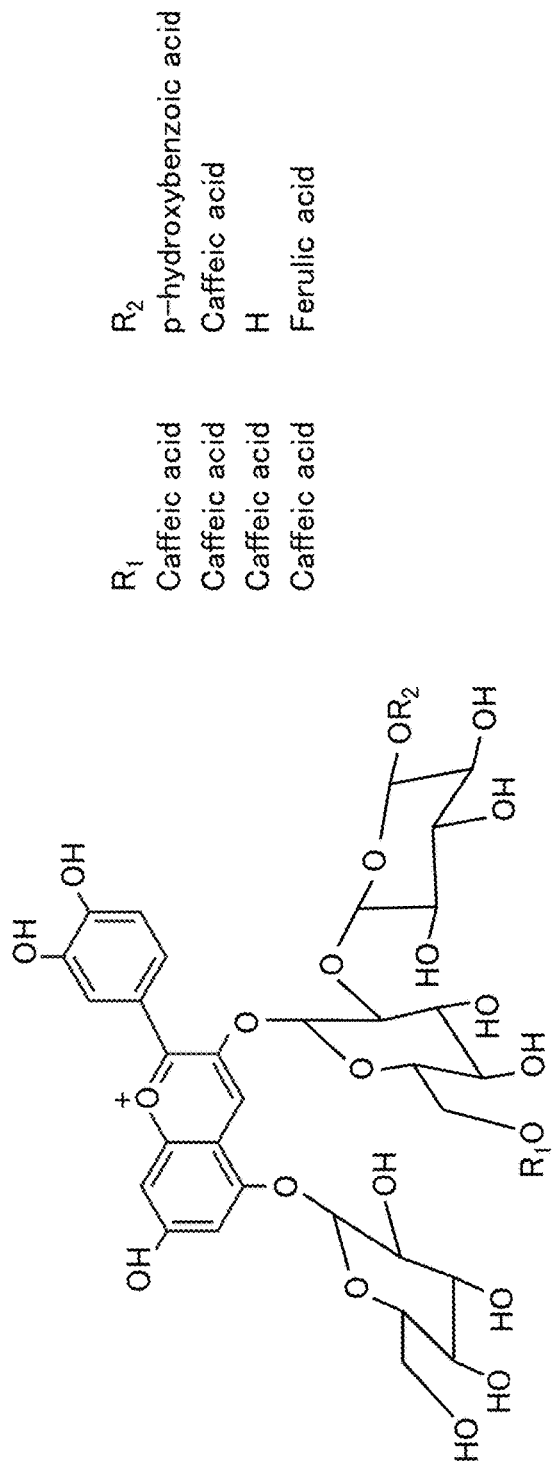
|  | $R_1$ | $R_2$ |
|---|---|---|
|  | Caffeic acid | p-hydroxybenzoic acid |
|  | Caffeic acid | Caffeic acid |
|  | Caffeic acid | H |
|  | Caffeic acid | Ferulic acid |
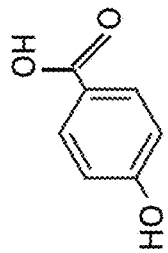
p-Hydroxybenzoic acid
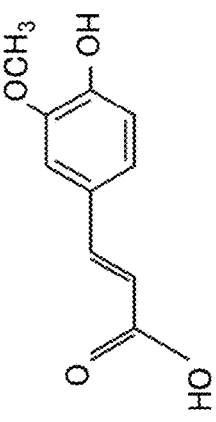
Ferulic acid
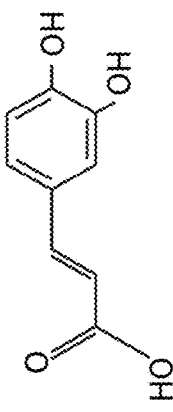
Caffeic acid (a)  (b)

(a)  (b)

(a)            (b)

1. Curcumin(turmeric)            2. Sulfuretin

FIG. 28
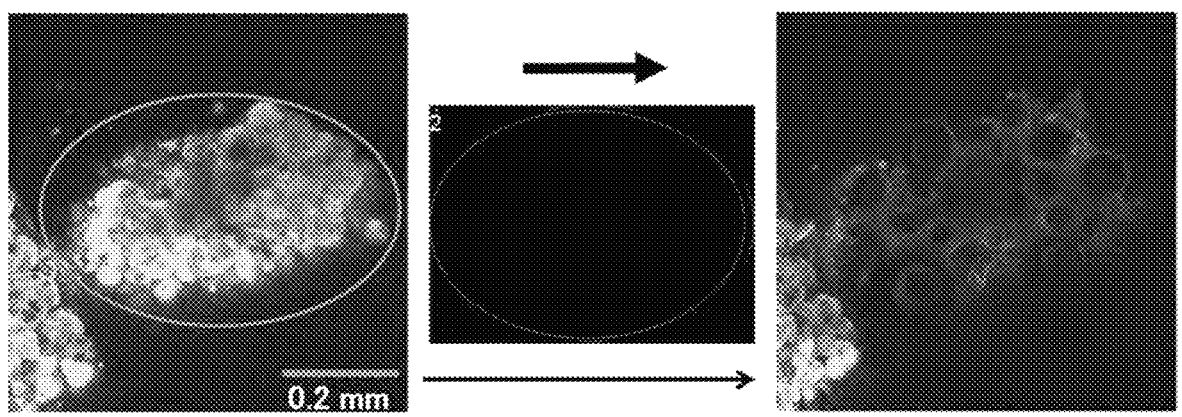
FIG. 29
(a) 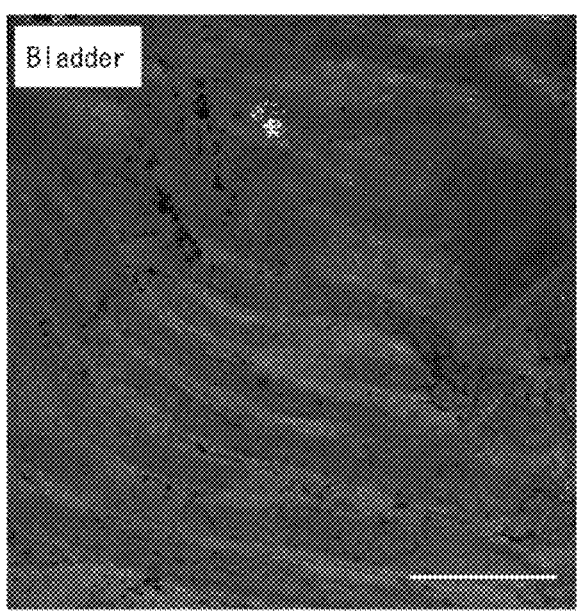 (b) 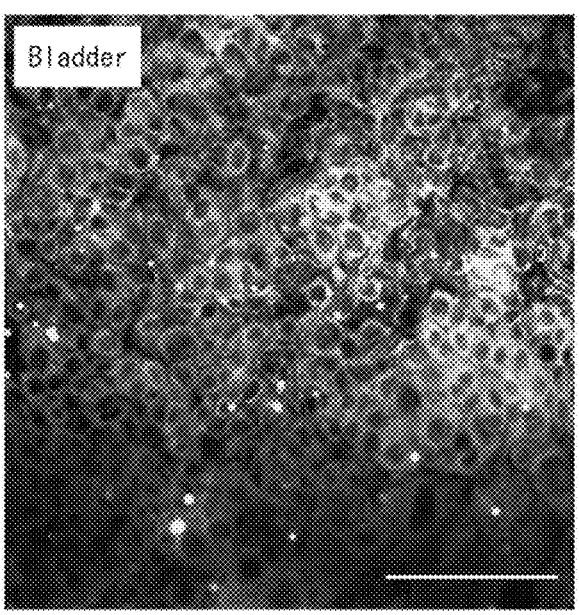
Bars: 50 μm

FIG.30
(a) 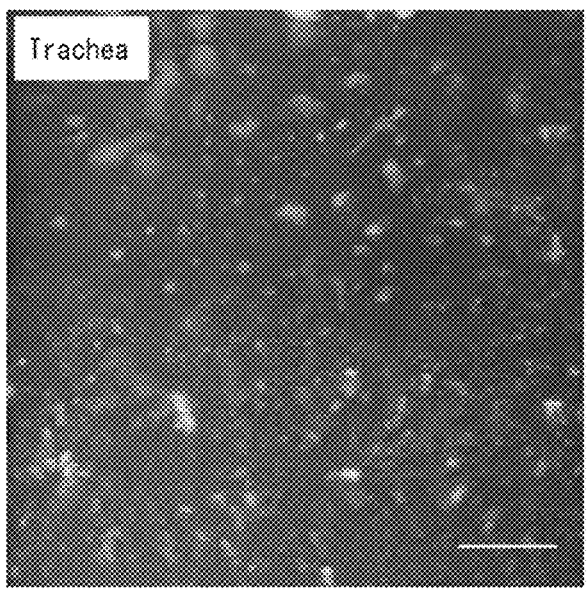
No staining
Laser power 82%
(b) 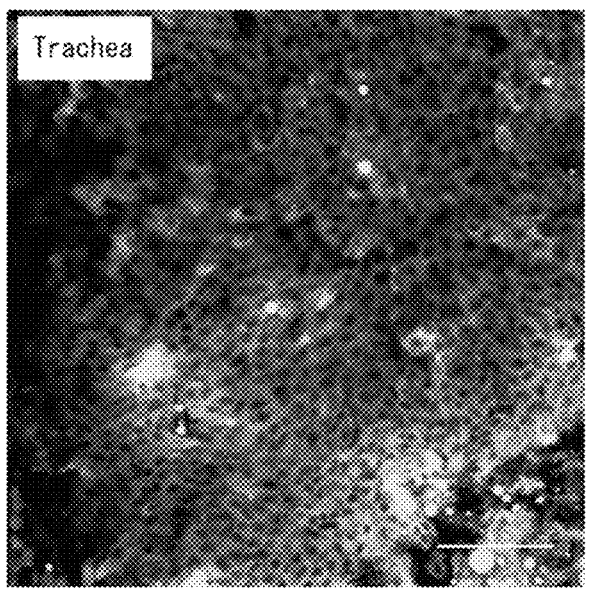
Curcumin staining
Laser power 3%
Bars:50 μm FIG. 31
(a) 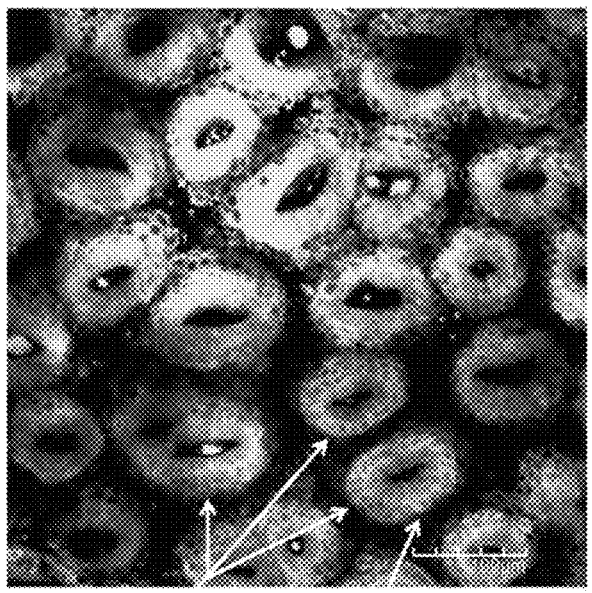
(b) [Human surgically excised stomach specimen: stomach cancer site]
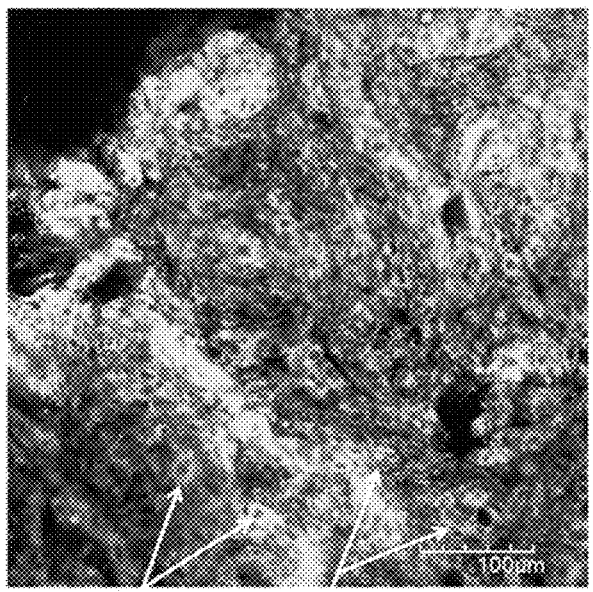
Circular structures    Normal epithelial cell          Large cells    Small cells

VITAL STAIN

CROSS-REFERENCE TO RELATED APPLICATIONS

This application is the U.S. National Phase of PCT/JP2014/059351, filed on Mar. 28, 2014, which is incorporated herein by reference it its entirety and which claims the benefit of JP Application No. 2013-074953, filed on Mar. 29, 2013, JP Application No. 2013-075150, filed on Mar. 29, 2013, and JP Application No. 2013-075256, filed on Mar. 29, 2013.

TECHNICAL FIELD

The present invention relates to a novel vital stain to be used in multiphoton laser microscopy and a method of observing cells using the stain, to a method of selecting and evaluating a novel vital stain to be used in multiphoton laser microscopy, to a novel cell stain selected by the method, to a novel tumor cell stain to be used in multiphoton laser microscopy and to a detection method for tumor cells using the stain, as well as to a multiphoton laser diagnosis and treatment apparatus for observation of patient tissues using the phenomenon of multiphoton absorption and for selective destruction of a portion of the tumor tissues by laser ablation.

BACKGROUND ART

Various diagnostic methods are used for cancer diagnosis, and in recent years, there have been developed noninvasive diagnostic methods in which affected area cells are observed using endoscopes (including both flexible scopes such as fiberscopes and rigid endoscopes such as bronchoscopes), to confirm diseases of the digestive system, respiratory system, renal/urinary system, utero-ovarian reproductive system, cerebrospinal nervous system and the like, or the presence or absence of tumorous cancer cells.

Since 1981, when cancer surpassed stroke as a cause of Japanese deaths, the number of deaths by cancer has continued to increase. It has therefore become a matter of social urgency to reduce the number of cancer patient deaths. Because cancers progress gradually with time after onset, its early detection is considered important for treatment. Endoscopy plays an important role in early detection of digestive organ cancers.

As has been shown by research on breast cancers, most cancers reach a diameter of about 5 millimeters by 6 years after onset. It is extremely difficult to detect cancers of this size with existing endoscopes. Thereafter, by the 7th year, it is referred to as "early cancer", having a diameter of about 10 millimeters, and if it is detectable at that point it is often curable by demucosation surgery by a physician using an endoscope. Because of the detection limit, however, with endoscopy it is only possible to discover early cancer in patients that have undergone medical examination during a period of 6 months before or after the 7th year.

The detectable period for early cancer is therefore limited. In cases of advanced cancers that have exceeded this period, treatment by endoscope is difficult, and for advanced cancers in stage 2 or 3 it is necessary to rely on laparotomy by a surgeon for excision of the cancer. When cancers further progress to stage 4, there is a high probability of distant metastasis of the cancers to organs outside of the gastrointestinal tract, such as the liver, lungs or brain, and chemotherapy or radiation therapy by a physician becomes necessary. Consequently, it may be said that the cancer detecting power of an endoscope determines the rate of detection of early cancers, and thus the curability of the cancers.

Endoscopy allowing direct observation of lesions plays an important role in the histopathological diagnosis of digestive organs. In recent years, early detection of microlesions is becoming possible due to the development of endoscope systems for Narrow Band Imaging (NBI)®, that accentuate mucosal surface layer capillaries and fine mucosal patterns. However it is not possible to observe individual cells even by NBI, and biopsy is necessary for accurate diagnosis of lesions.

Thus, biopsy tissue diagnosis plays an important role in the diagnosis of gastrointestinal tract diseases such as stomach cancers. Biopsy tissue diagnosis is conducted by performing hematoxylin eosin staining (HE staining) of tissue from an affected area that has been sampled by endoscopy, and having a histological diagnosis of the sample made by a pathologist. However, biopsy is an invasive procedure and also costly, while about 10 days are necessary to obtain diagnosis results.

Attempts to diagnose diseases from cellular images taken upon staining living cells have also been proposed for years, but the safety of the dyes or dye compounds used have been an issue. In particular, for the development of new dyes there is a legal requirement to verify whether or not any harmful effects are produced by administration of a candidate dye. The safety verification procedure for a new dye compound requires a minimum of 10 years and a cost of several billion yen per compound.

Methods that have been proposed for observing deep parts of live tissues include diagnostic methods using multiphoton laser microscopy, as described in PTLs 1 to 3. In multiphoton laser microscopy, the multiphoton excitation phenomenon is utilized to focus ultra-short pulse laser light inside the tissues, and the fluorescence emitted upon excitation by the ultra-short pulse laser light at the focal point is observed. Because multiphoton laser microscopy is capable of pinpoint excitation in principle, it is possible to scan the ultra-short pulse laser while detecting the fluorescence, and perform image processing to obtain a high-resolution fluorescent image.

Multiphoton laser microscopic visualization of FAD (flavin adenine dinucleotide) that is present in cells is expected to have applications in endoscope technology because it allows low-invasive analysis of the behavior of living cells and molecules. Since multiphoton laser microscopy accomplishes visualization of intracellular flavin at a wavelength of about 730 nm, it allows an autologous fluorescent image to be obtained without exogenous staining of the cells (Rogart, J. N., et al., "Multiphoton imaging can be used for microscopic examination of intact human gastrointestinal mucosa ex vivo", Clin Gastroenterol Hepatol 2008 January; 6(1): 95-101). However, the images obtained under multiphoton laser microscopy are of low contrast. In addition, because ultraviolet rays are emitted in the body upon irradiation of the multiphoton laser, it has not been approved for use in humans due to the risk of DNA damage. Furthermore, the strength of the autologous fluorescence of cells differs significantly with different organs, and while epithelial cells of the gastrointestinal tract such as the large intestine, which have strong autologous fluorescence, allow visualization of cellular images using currently marketed multiphoton laser microscopes, ovarian epithelial cells or bladder epithelial cells, which have weak autologous fluorescence, are difficult to be visualized as cellular images using currently marketed multiphoton laser microscopes (Cruz, J., et al. BIOMEDICAL OPTICUS EXPRESS 1, 5, 1320-1330, 2010).

CITATION LIST

Patent Literature

[PTL 1] Japanese Unexamined Patent Publication HEI No. 10-186424
[PTL 2] Japanese Unexamined Patent Publication No. 2008-286883
[PTL 3] Japanese Unexamined Patent Publication No. 2010-8082

Non-Patent Literature

[NPL 1] Rogart, J. N., et al., Clin Gastroenterol Hepatol 2008 January; 6(1): 95-101
[NPL 2] Cruz, J., et al. BIOMEDICAL OPTICUS EXPRESS 2010, 1, 5, 1320-1330
[NPL 3] Hogan, C., et al., Nat. Cell Biol., 2009, 11(4), 460-467

DISCLOSURE OF THE INVENTION

Problems to be Solved by the Invention

In order to realize early detection of diseases of the digestive system, respiratory system, renal/urinary system, utero-ovarian reproductive system, cerebrospinal nervous system and the like by examination using endoscopes (including both flexible scopes such as fiberscopes and rigid endoscopes such as bronchoscopes), and thus promptly reduce the number of cancer patient deaths, which is an issue of social urgency, the present invention, according to a first aspect, provides a novel vital stain to be used under multiphoton laser microscopy and a method of observing cells using the stain, according to a second aspect, provides a method for evaluating a novel vital stain to be used under multiphoton laser microscopy, and according to a third aspect, provides a novel tumor cell stain to be used under multiphoton laser microscopy and a detection method for tumor cells using the stain.

Furthermore, multiphoton laser microscopy allows high-resolution fluorescent images to be obtained, so that small clusters of cancer cells at the early cancer stages can be detected. However, even when cancer cells or cancer tissue are detected by multiphoton laser microscopy, they cannot be treated, as treatment requires the use of other devices or surgical intervention, and therefore in lesions such as early cancer that are small, effort is still necessary to identify the locations of the cancer cells or cancer tissues during treatment.

It is therefore another object of the invention to eliminate this problem of the prior art, and to provide a diagnosis and treatment apparatus that facilitates detection of small cancer tissues in the body, and also allows removal of the detected cancer tissues.

The invention therefore provides, according to a fourth aspect, a multiphoton laser diagnosis and treatment apparatus for observation of patient tissues utilizing the multiphoton absorption phenomenon, and selective destruction of a portion of the tissues.

Means for Solving the Problems

For the first aspect, among numerous natural dyes and artificial synthetic dyes, the present inventors focused on food coloring dyes that have been approved for oral administration to humans. As a result of studying the multiphoton laser-induced fluorogenic activity and cellular stainability of numerous dyes, many were found that allow imaging of cellular tissue morphology at high contrast and high resolution under multiphoton laser microscopy, and the present invention has thereupon been completed.

According to the first embodiment, the invention provides a vital stain for observation under multiphoton laser microscopy, the vital stain comprising one or more edible dye compounds. The dye compound is selected from among the group of fluorescent dyes including tar-based dye (Red #3 (erythrosine), Red #104 (phloxine), Red #106, Green #3 (Fast Green FCF), Red #2, Red #102, Blue #2 (indigo carmine), Yellow #4 (tartrazine), Yellow #5 (Sunset Yellow FCF), and the like), iridoid dyes (Haimeron P-2 (*Gardenia* Blue: geniposide), HI BLUE AT (*Gardenia* Blue dye: geniposide), and the like), carotenoid-based dyes (Haimeron P-2 (yellow dye: crocin), annatto (annatto N2R25, achiote fruit: bixin, norbixin), Haimeron P-2 (*Gardenia* Blue: geniposide), crocin G150 (*Gardenia* Yellow dye), crocin L (*Gardenia* Yellow dye), β-carotene, annatto WA-20 (annatto dyes, achiote seed: norbixin), and the like), flavonoid-based dyes (HI RED G150 (grape peel dye, anthocyanin), HI RED RA200 (red radish dye: pelargonidin acyl glucoside), HI RED V80 (purple potato dye: cyanidin acyl glucoside and peonidin acyl glucoside), apigeninidin (kaoliang dye), cyanidin, delphinidin (eggplant dye), fisetinidin (*Acacia mearnsii* dye), malvidin (blue sweet pea dye), pelargonidin, robinetinidin (*Robinia pseudoacacia* tree pigment), tricetinidin (black tea dye), petunidine (red berry dye), capsanthin (*capsicum* pigment), epigallocatechin gallate, green tea, Safflower Y1500 (safflower dye, safflomin A+B), curcumin, sulfuretin, myricetin (grape, onion dye) or quercetin (onion, citrus dyes), quinoid-based dyes (cochineal (Cochineal Red AL, carminic acid), HI RED S (lac dye/laccaic acid), and the like), betalain-based dyes (HI RED BL (red beet dye: betanin, isobetanin), and the like), India cyanine green, and gingerol (ginger spice component).

The vital stain of the invention can dye luminal epithelial cells, and adenocytes and/or connective tissue or capillary system cells, and preferably cancer cells. The dye compound is excited with a multiphoton laser emitting a long wavelength of 700 nm or greater, and preferably 800 nm or greater.

According to a second embodiment, the invention provides a method of observing cells in the body of a subject or taken from the body of a subject, or the cultured cells, using the aforementioned vital stain, the method comprising 1) applying the vital stain to the cells, and 2) observing the cells under a multiphoton laser microscope. According to another embodiment, the observing method of the invention further comprises 3) distinguishing between normal cells and cancer cells based on differences in stainability between the cells.

For the second aspect, the present inventors conducted an extensive research on the issue of providing a method of efficiently evaluating and selecting stains having a cell staining property such that they preferentially stain cancer cells or preferentially stain normal cells, or stain both to the same extent, and have completed a method of evaluating and selecting such stains. Furthermore, this method of evaluating and selecting was utilized to discover stains having cell staining properties, from among a large number of as many as 1200 different food dyeing agents.

According to the first embodiment, the invention provides a method of evaluating the cell staining property of a vital stain by observation under a multiphoton laser microscope, the method comprising a) mixing cancer cells and normal cells, b) culturing the mixture to a confluent or a sub-confluent state, c) applying the stain to be evaluated to the cultured product, and d) determining whether the stain) specifically stains cancer cells, ii) specifically stains normal cells, or iii) stains both cancer cells and normal cells. Preferably, in step b), culturing of the mixture is to a confluent or sub-confluent state under conditions in which cancer cells preferentially proliferate. Preferably, the method is designed such that the cancer cells are canine renal tubular epithelial cells that express Ras$^{V12}$ (MDCK-Ras$^{V12}$), and addition of tetracycline causes preferential proliferation of cancer cells. Preferably, the method includes a step of labeling the cancer cells with a reporter gene and comparing expression of the reporter gene with staining by the stain, in order to evaluate whether or not cancer cells are specifically stained. Preferably, the reporter gene is the GFP gene.

According to a second embodiment, the invention provides a stain that specifically stains cancer cells in contrast to normal cells, for observation under a multiphoton laser microscope, the cell stain comprising one or more dye compounds selected from the group consisting of meclocycline sulfosalicylate, methacycline hydrochloride, merbromin, Fast Green FCF, Red #3 (erythrosine) and Red #104.

In addition, the invention provides a cell stain that specifically stains normal cells in contrast to cancer cells, for observation under a multiphoton laser microscope, the cell stain comprising one or more dye compounds selected from the group consisting of mitoxantrone dihydrochloride and doxorubicin hydrochloride.

Furthermore, the invention provides a stain that equally stains normal cells and cancer cells, for observation under a multiphoton laser microscope, the cell stain comprising one or more dye compounds selected from the group consisting of pyrvinium pamoate, Chicago Sky Blue 6B, Acid Red and HI RED V80 (purple potato dye).

Yet furthermore, the invention provides a cell stain comprising a mixture of a cell stain that specifically stains cancer cells in contrast to normal cells, for observation under a multiphoton laser microscope, the cell stain comprising one or more dye compounds selected from the group consisting of meclocycline sulfosalicylate, methacycline hydrochloride, merbromin, Fast Green FCF, Red #3 (erythrosine) and Red #104, and a cell stain that equally stains normal cells and cancer cells, the cell stain comprising one or more dye compounds selected from the group consisting of pyrvinium pamoate, Chicago Sky Blue 6B, Acid Red and HI RED V80 (purple potato dye).

Preferably, the cell stain is used at a concentration of 0.1 μM to 10 μM as the total concentration of the stain. Also preferably, the cell stain further contains an isotonizing agent, a pH regulator, a stabilizer, a thickening agent, an antiseptic agent, an aromatic agent and/or a pressure-sensitive adhesive. Preferably, the cells are luminal epithelial cells, and adenocytes and/or connective tissue or capillary system cells. Also preferably, the dye compound is excited by a multiphoton laser with a wavelength of 700 nm or longer.

According to a third embodiment, the invention provides a method of detecting cancers in cells obtained from a subject or in cultured cells, using the aforementioned cell stain, the method comprising 1) applying the cancer cell stain to the cells, and 2) distinguishing normal cells and cancer cells based on the difference in stainability, under a multiphoton laser microscope. This method preferably further comprises 3) eliminating the tumor cells by multiphoton laser irradiation.

According to a fourth embodiment, the invention provides a method of evaluating the cell staining property of a vital stain for pluripotent stem cell-derived cells, by observation under a multiphoton laser microscope, the method comprising a) applying a stain to be evaluated to a cultured product containing a mixture of normal differentiated cells and undifferentiated cells derived from pluripotent stem cells, and b) determining whether the stain) specifically stains undifferentiated cells, ii) specifically stains normal differentiated cells, or iii) stains both normal differentiated cells and undifferentiated cells. Culturing of the cultured product as a mixture of normal differentiated cells and undifferentiated cells may be continued until the culture mixture reaches a confluent or sub-confluent state, before application of the stain. The pluripotent stem cells may be iPS cells, ES cells or MUSE cells. Preferably, the method includes labeling the pluripotent stem cells with a reporter gene and comparing expression of the reporter gene with staining by the stain, in order to evaluate whether or not pluripotent stem cells are specifically stained. Preferably, the reporter gene is the GFP gene. The undifferentiated cells may also be cancer cells.

For the third aspect, among numerous natural dyes and artificial synthetic dyes, the present inventors focused on food coloring dyes and the like that have been approved for oral administration to humans. As a result of studying the multiphoton laser-induced fluorogenic activity and cellular stainability of numerous dyes, it was learned that certain dyes allow imaging of cellular tissue morphology at high contrast and high resolution under multiphoton laser microscopy, to a degree that permits distinction between normal cells and tumor cells, and the present invention has thereupon been completed.

Consequently, according to the first embodiment, the invention provides a tumor cell stain for observation under multiphoton laser microscopy, the tumor cell stain comprising one or more dye compounds selected from the group consisting of curcumin, sulfuretin, erythrosine, epigallocatechin gallate and Acid Red. The stain of the invention can dye luminal epithelial cells, and adenocytes and/or connective tissue or capillary system cells. The dye compound is excited with a multiphoton laser emitting a long wavelength of 700 nm or greater, and preferably 800 nm or greater.

According to the second embodiment, the invention provides a method of detecting a tumor in cells in the body of a subject or taken from the body of a subject, or the cultured cells, using the aforementioned tumor cell stain, the method comprising 1) applying the tumor cell stain to the cells, and 2) distinguishing normal cells and tumor cells based on the difference in stainability, under a multiphoton laser microscope. Depending on the embodiment, the detecting method of the invention further comprises 3) eliminating the tumor cells by multiphoton laser irradiation.

Multiphoton laser microscopy allows high-resolution fluorescent images to be obtained, so that small clusters of cancer cells at the early cancer stages can be detected. However, even when cancer cells or cancer tissues are detected by multiphoton laser microscopy, they cannot be treated, as treatment requires the use of other devices or surgical intervention, and therefore in lesions such as early cancers that are small, effort is still necessary to identify the locations of the cancer cells or cancer tissues during treatment. It is therefore desirable to eliminate this problem of the prior art, and to provide a diagnosis and treatment apparatus that facilitates detection of small cancer tissues in the body, and also allows removal of the detected cancer tissues.

Thus, in light of the object stated above, according to the fourth aspect the invention provides a multiphoton laser diagnosis and treatment apparatus for observation of patient tissues using the multiphoton absorption phenomenon and selective destruction of a portion of the tissues, the multiphoton laser diagnosis and treatment apparatus comprising a laser light source that emits pulse laser light with adjustable frequency and output, an optical system that irradiates the pulse laser light from the laser light source onto a focal point in tissues, a focal point displacing device that displaces the focal points, a photodetector that detects fluorescence emitted from tissues by irradiation of the pulse laser light, a fluorescent image generating device that generates a fluorescent image of the tissues by processing in coordination with the parameter representing the focal points, obtained from the focal point displacing device, and the intensity of fluorescence detected by the photodetector, and a controller, wherein the periphery of the optical system is covered by a tubular shield member, the shield member forming a space that encloses the optical system by contact bonding with the perimeter of the tissues to be observed, the shield member being provided with a vent hole for adjustment of the pressure in the space, the controller including a pulsed light intensity setting adjuster that sets the intensity of the pulse laser light, an irradiation range setting adjuster that sets the irradiation range for pulse laser light on the fluorescent image, and an irradiation time setting adjuster that sets the irradiation time for the pulse laser light, and wherein pulse laser light of an intensity established by the pulsed light intensity setting adjuster is irradiated while scanning by the focal point displacer in the coordinate range established by the irradiation range setting adjuster, for the time established by the irradiation time setting adjuster, selectively destroying cells of the tissues within the irradiation range established by the irradiation range setting adjuster using the energy of the pulse laser light.

The shield member may further comprise a fluid supply inlet and a fluid drainage outlet for supply and drainage of fluid in the space, in which case the fluid supply inlet and the fluid drainage outlet may be the same one or different, and the fluid supply inlet and the fluid drainage outlet may also serve as a gas inlet and a gas outlet. Preferably, the fluid is a staining solution containing the stain for staining of the tissues, and a cleaning fluid for cleaning of the staining solution.

In the multiphoton laser diagnosis and treatment apparatus, pulse laser light from the laser light source is irradiated onto patient tissues by an optical system, and the fluorescence excited by the pulse laser light due to the multiphoton absorption phenomenon is detected at the photodetector, to generate a fluorescent image of the patient tissues by the fluorescent image generating device. In particular, since multiphoton excitation takes place in a pinpoint manner in principle, a high-resolution fluorescent images can be obtained. A physician can perform diagnosis and identify the site of cancer tissues, based on the high-resolution fluorescent images. Also, the fluorescent image is processed in correlation with the parameter representing the focal point obtained from the focal point displacing device (i.e. the coordinates), and the intensity of fluorescence emitted from the tissue at the focal point, and with one-to-one correspondence possible between each of the coordinate points on the fluorescent images and the setting of the focal point displacing device, settings may be rendered that displace the focal point of the pulse laser light to a point on the patient tissues corresponding to the point of each coordinate on the fluorescent image. Thus, if the site of the cancer tissue is set as the irradiation range for the pulse laser by the irradiation range setting adjuster of the controller on the generated fluorescent image, and the intensity of the pulse laser light and the irradiation time are set to sufficient values for destruction of the cancer cells, by the pulsed light intensity setting adjuster and irradiation time setting adjuster of the controller, carrying out irradiation of pulse laser light in the set irradiation range, then it is possible to selectively destroy and treat cancer tissues in an accurate manner by the multiphoton absorption phenomenon, utilizing the irradiation range indicated on the fluorescent images. Furthermore, since the multiphoton excitation takes place in a pinpoint manner in principle to allow destruction of the cancer tissues in cellular units, it is possible to destroy the minimum area of cancer tissues. Consequently, the burden on the patient during destruction of the cancer cells can be kept to a minimum.

Preferably, the tissue is one that has been stained with application of stain on the surface, and the fluorescent image generating device generates a fluorescent images based on the fluorescence from the stained tissues.

Furthermore, the focal point displacing device preferably further includes a two-dimensional scanner that scans the pulse laser light in the two axial directions that are perpendicular to the optical axis of the pulse laser light, and a focal depth controller for adjustment of the depth of the focal points of the laser light on the tissues.

In addition, the pulse intensity setting adjuster preferably includes a diagnostic pulse intensity setting adjuster that adjusts the pulse laser light intensity for diagnosis, and a treatment pulse intensity setting adjuster that sets the pulse laser light intensity for treatment. In this case, the pulse laser intensity set at the diagnostic pulse intensity setting adjuster is more preferably no greater than $1/10$ of the intensity set at the treatment pulse intensity setting adjuster.

The optical system includes an objective lens for focusing of the pulse laser light onto the focal points, the numerical aperture of the objective lens preferably being 1.0 or greater.

The optical system and the focal point displacing device are provided in a laser light irradiating head, and the multiphoton laser diagnosis and treatment apparatus may further comprise a patient immobilizing platform for immobilization of the patient, and a moving apparatus that moves the patient immobilizing platform and the laser light irradiating head relative to each other in 3 axial directions, while the optical system may be provided inside an endoscope, the pulse laser light being irradiated onto the tissues from the laser light source through the endoscope.

Effect of the Invention

During the course of analyzing numerous orally ingestible compounds for multiphoton laser fluorogenic activity and cellular stainability, it was found that the staining patterns of different dyes in normal cells and/or cancer cells are categorized according to certain staining specificities. According to the invention, therefore, it is possible to rapidly identify lesion sites utilizing the difference in dye affinities between cancer and normal cells, to ascertain the quality (disease state) of mucosal lesions from cytomorphology.

Because a staining method by the vital stain of the invention can reduce the laser light exposure dose required for taking cellular images of sufficient image quality for image diagnosis to approximately $1/30$ compared to conventional autologous fluorescence observation methods (approximately 1/100 when using a gallium arsenide high-sensitivity photomultiplier), it is possible to vastly reduce photodamage to mucosal cells, and since the laser excitation wavelength can be set to the long wavelength end (800 nm or longer), ultraviolet ray generation in tissues is minimized and DNA damage in mucosal cells can be reduced. Furthermore, images visualized by the vital stain of the invention are of sufficiently high image quality even compared to confocal laser microscope images with intravenous systemic administration of fluorescent dyes or multiphoton laser microscope images by autologous fluorescence without exogenous staining.

In addition, the apparatus of the invention allows cancer diagnosis to be performed using the multiphoton absorption phenomenon of pulse laser light, to take high-resolution fluorescent images. Moreover, by adjusting the intensity of the pulse laser light and the irradiation time, it is possible to destroy cells in a specified region on a fluorescent image, and to easily and accurately remove detected cancer tissues.

BRIEF DESCRIPTION OF THE DRAWINGS

FIG. 6A is a set of photomicrographs showing the staining patterns of dye compounds that provide high-contrast multiphoton laser images.

FIG. 6B is a set of photomicrographs showing the staining patterns of dye compounds that provide high-contrast multiphoton laser images.

FIG. 6C is a set of photomicrographs showing the staining patterns of dye compounds that provide high-contrast multiphoton laser images.

FIG. 6D is a set of photomicrographs showing the staining patterns of dye compounds that provide high-contrast multiphoton laser images.

FIG. 21B shows the constituent component cyanidin acyl glucoside of HI RED V80.

FIG. 28 is a set of multiphoton laser microscope photographs showing a process in which a tumor having a diameter of 0.5 millimeter was eliminated by laser irradiation (power: 100%, irradiation time: 20 seconds).

FIG. 29 is a pair of multiphoton laser microscope photographs of mouse bladder epithelial cells, which are (a) a photograph taken of non-curcumin-stained cells at 82% laser power (autologous fluorescence) and (b) a photograph taken of curcumin-stained cells at 3% laser power.

FIG. 30 is a pair of multiphoton laser microscope photographs of mouse tracheal epithelial cells, which are (a) a photograph taken of non-curcumin-stained cells at 82% laser power (autologous fluorescence) and (b) a photograph taken of curcumin-stained cells at 3% laser power.

FIG. 31 is a pair of multiphoton laser microscope photographs taken with curcumin staining and 1% laser power, of normal gastric mucosa site (a) and a stomach cancer site (b), in fresh surgically excised gastric mucosa.

BEST MODE FOR CARRYING OUT THE INVENTION

<Novel Vital Stain>

Figure 1:
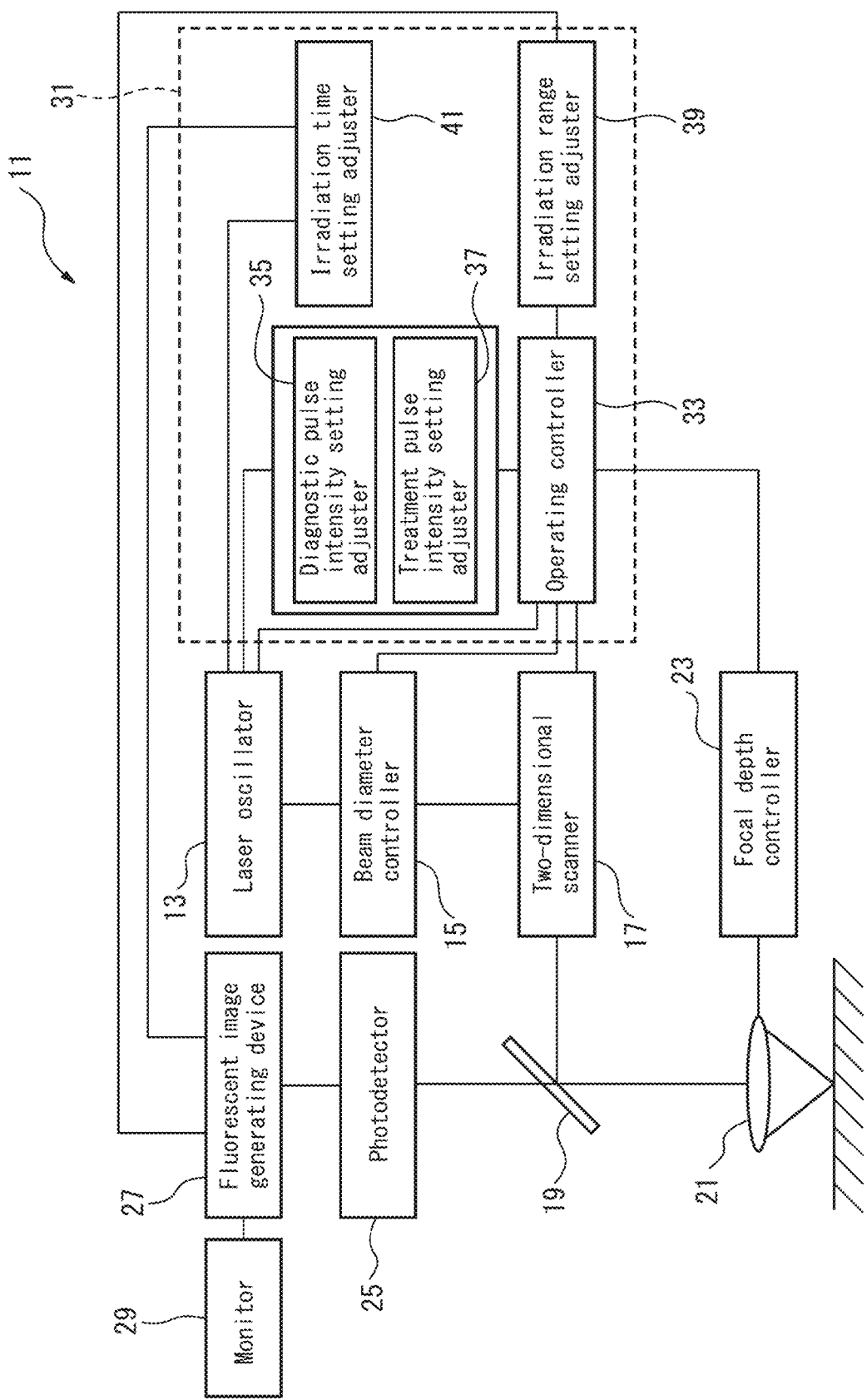
FIG. 1 is a general schematic drawing of a multiphoton laser diagnosis and treatment apparatus according to the invention.

A vital stain of the invention contains an edible natural (animal or vegetable) or synthetic dye compound that is approved as a food additive or the like. As used herein, the term "edible" means not that the compound of interest is originally tended to be used for food, but that it is guaranteed to have sufficient safety to be added to foods and the like, and that it can be administered to animals having luminal organs, including humans. Edible dye compounds according to the invention are selected from the group of fluorescent dye compounds that include, for example, tar-based dyes, and especially edible tar-based dyes, iridoid dyes, carotenoid-based dyes, flavonoid-based dyes (for example, catechins and anthocyanins, and especially anthocyanidins, chalcones and curcuminoids), quinoid-based dyes and betalain-based dyes. Dye compounds of the invention may be classified as follows, according to structure.

1. Tar-Based Dyes

Examples of tar-based dyes include the following compounds:

Red #3 (erythrosine), Red #104 (phloxine), Red #106 (Acid Red), Green #3 (Fast Green FCF), Red #2, Red #102, Blue #2 (indigo carmine), Yellow #4 (tartrazine), Yellow #5 (Sunset Yellow FCF), and the like.

2. Iridoid Dyes

Examples of iridoid dyes include the following compounds:

Haimeron P-2 (*Gardenia* Blue: geniposide), HI BLUE AT (*Gardenia* Blue dye: geniposide), and the like.

3. Carotenoid-Based Dyes

Examples of carotenoid-based dyes include the following compounds:

Haimeron P-2 (yellow dye: crocin), annatto (annatto N2R25, achiote fruit: bixin, norbixin), Haimeron P-2 (*Gardenia* Blue: geniposide), crocin G150 (*Gardenia* Yellow dye), crocin L (*Gardenia* Yellow dye), β-carotene, annatto WA-20 (annatto dye achiote seed: norbixin), and the like.

4. Flavonoid-Based Dyes

Examples of flavonoid-based dyes include anthocyanins, and particularly anthocyanidins, catechins, chalcones, curcuminoids and the like.

Examples of anthocyanins include the following compounds:

HI RED G150 (grape peel dye, anthocyanin), HI RED RA200 (red radish dye: pelargonidin acyl glycoside), HI RED V80 (purple potato dyes: cyanidin acyl glucoside and peonidin acyl glucoside), apigeninidin (kaoliang dye), cyanidin, delphinidin (eggplant dye), fisetinidin (*Acacia mearnsii* dye), malvidin (blue sweet pea dye), pelargonidin, robinetinidin (*Robinia pseudoacacia* tree pigment), tricetinidin (black tea dye), petunidine (red berry dye), capsanthin (*capsicum* pigment), and the like.

Examples of catechins include epigallocatechin gallate, green tea, and the like.

Examples of chalcones include Safflower Y1500 (safflower dye, safflomin A+B), and the like.

Examples of curcuminoids include curcumin and the like.

Examples of other flavonoid-based dyes include the following compounds:

Sulfuretin, myricetin (grape, onion dye), quercetin (onion, citrus dyes), and the like.

5. Quinoid-Based Dyes

Examples of quinoid-based dyes include the following compounds:

Cochineal (cochineal red AL, carminic acid), HI RED S (lac dye/laccaic acid), and the like.

6. Betalain-Based Dyes

Examples of betalain-based dyes include HI RED BL (red beet dye: betanin, isobetanin), and the like.

Other fluorescent dye compounds include indocyanine green, gingerol (ginger spice component), and the like.

The dye compounds to be used for the invention each have different stainabilities, and may be classified as follows based on their stainability for normal cells.

1) Dyes that are Strongly Excited by Multiphoton Laser Light and Produce Bright Living Cell Images Curcumin (derived from turmeric or the like), sulfuretin, epigallocatechin gallate, Red #3 (erythrosine), Red #106, Green #3, Red #2, Red #102, Red #104 (phloxine), Blue #2, Yellow #4, Yellow #5, Haimeron, annatto, indocyanine green, *Gardenia* Yellow dye, crocin G-150, safflomin, HI BLUE AT, fluorescein, cyanidin, delphinidin, fisetinidin, robinetinidin, pelargonidin, apigeninidin, malvidin, β-carotene, HI RED RA200, HI RED V80, HI RED BL, 6-gingerol, quercetin, myricetin, tricetinidin and petunidine.

2) Dyes that Preferentially Darkly Stain Specific Cell Structures Composing Luminal Organs Such as in the Gastrointestinal Tract The cellular structures of the gastrointestinal tract mucosa can be classified into a cell group composed of epithelial cells covering the mucosal surface through which food passes and adenocytes where the epithelial cells are invaginated into an urn shape and secrete mucus (first series), and a cell group composed of capillaries and connective tissue cells that fill in the peripheries of the epithelial cells and adenocytes (second series). When an objective lens approaches the mucosal surface, epithelial cells are observed for the most part when the focus is directed onto the mucosal surface, while adenocytes and connective tissue and capillaries are observed when the focus is directed more deeply.

2-1) Dyes that Preferentially Stain First Series Cell Group

Curcumin (Dye No. 1), sulfuretin (Dye No. 2), epigallocatechin gallate (Dye No. 3), Red #3 (erythrosine) (Dye No. 4), Red #104 (phloxine) (Dye No. 9), indocyanine green (Dye No. 15), malvidin (Dye No. 27), β-carotene (Dye No. 28), HI RED BL (Dye No. 32), 6-gingerol (Dye No. 33), myricetin (Dye No. 35), tricetinidin (Dye No. 36) and petunidine (Dye No. 37).

Among these dyes, curcumin and sulfuretin are preferred because of their high stainability.

2-2) Dyes that Preferentially Stain Second Series Cell Group

Annatto (Dye No. 14), quercetin (Dye No. 34), Blue #2 (Dye No. 10), Gardenia Yellow dye (Dye No. 16), crocin G-150 (Dye No. 17), safflomin (Dye No. 18), robinetinidin (Dye No. 24), HI RED V80 (Dye No. 31) and quercetin as Dye No. 34 (Dye No. 34).

Among these dyes, annatto and quercetin are preferred because of their high stainability.

2-3) Dyes that Stain Both First Series and Second Series Cell Groups

Red #106 (Dye No. 5) strongly stains the cell membranes of epithelial cells and adenocytes, and also connective tissue/capillaries. Also, Green #3 (Dye No. 6) strongly stains some adenocytes and connective tissue/capillaries.

A vital stain of the invention can stain not only normal cells but also cancer cells. For example, many types of dyes such as curcumin, sulfuretin and Red #3 (erythrosine) stain cancer lesion sites more darkly than normal mucosa. By utilizing such staining specificity, it is possible to rapidly probe lesion sites. Incidentally, prior to the present invention it has not been known that cancer cells are more intensely stained than normal cells, when imaging gastrointestinal tract mucosal cells using a confocal laser microscope with intravenous injection of a fluorescent dye.

Furthermore, when a lesion site consists of cancer cells, because cancer cells have different morphological characteristics than normal cells, it is possible to distinguish normal cells from cancer cells based on their differences in morphology. Specifically, atypia is classified into two types, namely structural atypia (the cell population is not arranged in an orderly fashion on the basal membrane and does not form a glandular structure, etc.), and cellular atypia (disparate sizes of individual cells, unevenly located large nuclei, irregular polarity, etc.). With existing endoscopes it is difficult to detect cancer sizes of about 5 millimeters in diameter, but by using the vital stain of the invention under a multiphoton laser microscope that allows imaging of cytomorphology, it is possible to accomplish early visual detection of cancer sizes of about 1 millimeters in diameter based on differences in morphology, without conducting biopsy. When cancer has been detected, it may be eliminated by burning with multiphoton laser irradiation.

The dye compounds to be used for vital staining are appropriately selected from the group of compounds mentioned above. The vital stain of the invention may include one or a plurality of types of selected dye compounds. By combining different dye compounds, it is possible to obtain different staining patterns. The content of each dye compound is not particularly restricted so long as the dye compound does not precipitate in the vital stain solutions and the image necessary for pathological diagnosis can be taken. The concentration of the dye compound is also determined in consideration of toxicity to the subject. The concentration of the dye compound is also appropriately adjusted so that it does not precipitate in the vital stain solutions, and for example, the dye compound may be added in a range of approximately 0.01 mg/ml to 5 mg/ml, such as approximately 1 mg/ml, in the vital stain solutions. The dye compound may be suitably used at a concentration of 0.1 μM to 10 μM (molar concentration). In addition to the dye compound, there may be included publicly known dyes such as iodine that have been used in the prior art for endoscopy and the like. The dye compound is dissolved in a common solvent such as PBS, ethanol/glycerol, DMSO or the like.

The dye compound will have characteristic fluorogenic activity, but in all cases is excited with a multiphoton laser emitting a long wavelength of 700 nm or greater and preferably 800 nm or greater. Observation of the excitation light is conducted under multiphoton laser microscopy, and as used throughout the present specification, the term "multiphoton laser microscopy" means a fluorescent microscope that utilizes a multiphoton excitation process. Using two-photon excitation light as an example for illustration, the multiphoton excitation process is a nonlinear optical phenomenon in which a single fluorescent molecule simultaneously absorbs two photons having approximately twice the wavelength, i.e. ½ the energy, compared to one-photon excitation, and is converted to an excited state. Also, when it returns to a low-energy stable state from the excited state, energy is released as fluorescence and the fluorescence intensity is measured to construct a high-contrast image. Such multiphoton excitation is accomplished forcibly by using as the light source a pulse laser with a pulse width on the femtosecond order and a large peak power. The vital stain of the invention can be utilized with not only a two-photon, but even with a three-photon or greater multiphoton excitation process, and the multiphoton laser microscope used is not particularly restricted so long as it is provided with a function of generating long wavelength laser light.

The vital stain of the invention can stain a lumen, and preferably the epithelial cells/adenocytes/and/or cells of connective tissue/capillaries in digestive organs. The vital stain of the invention can also be used for observation of cells in vitro, and the cells may be obtained by biopsy from a subject, or cultured cells (for example, monolayer culture cells). As used herein, the term "cultured cells" includes cultured products of various types of stem cells, such as induced pluripotent stem cells (iPS cells), embryonic stem cells (ES cells), MUSE cells and tissue stem cells. Using the observation method of the invention, it is also possible to detect cancerized cells or undifferentiated cells arising during culturing, when such cells are to be applied for regenerative medicine.

There are no particular restrictions on the method of administering the vital stain, and for example, the vital stain may be directly administered to the lumen or administered submucosally, or it may be administered perorally, intravenously or intraperitoneally. When the vital stain has weak stainability, the mucosal surface is treated with pronase to remove the mucus, thereby improving the visibility of the cell structure. When the stain is to be directly applied to the inner surface of a lumen (for example, by coating or spraying), the dosage form is preferably liquid, although forms such as granules or tablets may also be used. Other appropriate added components that are necessary, including additives such as isotonizing agents, pH regulators, stabilizers, thickening agents, antiseptic agents, aromatics or pressure-sensitive adhesives, may be combined with the vital stain, depending on the dosage form and other factors.

For example, pronase may be preadded to the vital stain of the invention. Pronase is a specific example that may be used as a mucosa removing agent. Specific examples of isotonizing agents include sodium chloride, glycerin and the like, specific examples of pH regulators used as food additives include citric acid, gluconic acid, succinic acid, potassium carbonate, lactic acid and the like, specific examples of stabilizers and thickening agents include carrageenan, carboxymethyl cellulose sodium, xanthan gum, guar gum, pectin and the like, specific examples of antiseptic agents (preservatives) include benzoic acid and the like, and specific examples of pressure-sensitive adhesives include gelatin, starch, casein and the like, although there is no limitation to these so long as the substances can be safely used for living cells.

The method of observing the cells according to the invention includes applying the vital stain to cells obtained from a subject or cultured cells, and observing the stained cells under a multiphoton laser microscope. According to another embodiment, the observing method of the invention further includes detecting a cancerous lesion based on differences in stainability between the stained cells.

<Method for Evaluating Cell Staining Property of Novel Vital Stain>

The invention provides a method of evaluating the cell staining property of a vital stain under multiphoton laser microscope observation, or in other words, evaluating whether it specifically stains cancer cells, whether it specifically stains normal cells, or whether it equally stains both cancer cells and normal cells. The normal cells and cancer cells to be used in the evaluation method of the invention are preferably mammalian cells derived from the same species, and for example, cancer cells may be normal cells that have been transformed with oncogenes. Examples of mammalian cells include MDCK cells, MDBK cells, COS-cells, BSC-1 cells, LLC-MK cells, CV-1 cells, VERO cells, CRFK cells, RAF cells, RK-cells, TCMK-1 cells, LLC-PK cells, PK15 cells, LLC-RK cells, MDOK cells, BHK-21 cells, CHO cells, NS-1 cells, MRC-5 cells, WI-38 cells, BHK cells, 293 cells and RK-cells, with no limitation to these. Also, as normal cells, the cells used in the evaluation method of the invention are preferably MDCK normal cells, as a cell line derived from canine renal tubular epithelial cells, while cancer cells are preferably MDCK-GFP-Ras$^{V12}$ cells expressing the oncogene product Ras$^{V12}$ (Ras$^{V12}$ being Ras wherein the 12th amino acid residue glycine is replaced by valine, a mutation found in 30% to 40% of colon cancer cases). Cells expressing the oncogene product Ras$^{V12}$ have the property of being able to proliferate preferentially over normal cells, in the presence of added tetracycline.

In this evaluation method, preferably the cancer cells are labeled with a reporter gene, allowing expression of the reporter gene to be compared with staining by the stain, and allowing confirmation of whether or not the cancer cells are specifically stained by the stain. The reporter gene is not particularly restricted so long as it codes for a reporter protein that can function as a detection marker, and preferred examples are genes coding for proteins such as GFP, firefly luciferase, β-galactosidase, *Renilla* luciferase, alkaline phosphatase or the like. Among these reporter genes, a gene coding for GFP allows identification and detection by a simple method based on the presence or absence of fluorescence, and is therefore preferred for the invention.

Preferably, the reporter gene is functionally linked to a promoter for the oncogene, and is expressed together with expression of the oncogene.

As a result of evaluating 1200 different types of vital stains by the evaluation method described above, the present inventors have discovered the following cell staining properties.

Stains that specifically stain cancer cells compared to normal cells, under multiphoton laser microscopy observation:
  Meclocycline sulfosalicylate
  Methacycline hydrochloride
  Merbromin
  Fast Green FCF
  Red #3 (erythrosine)
  Red #104 (phloxine)

Stains that specifically stain normal cells compared to cancer cells, under multiphoton laser microscopy observation:
  Mitoxantrone dihydrochloride
  Doxorubicin hydrochloride Stains that equally stain normal cells and cancer cells, under multiphoton laser microscopy observation:
  Pyrvinium pamoate
  Chicago Sky Blue 6B
  Acid Red
  HI RED V80 (purple potato dye)

Stains that specifically stain cancer cells compared to normal cells under multiphoton laser microscopy observation stain cancer lesion sites more intensely than normal mucosa. Such staining specificity can be utilized to allow rapid exploration of lesion sites. In particular, since cancer cells have different morphological characteristics from normal cells, it is possible to distinguish normal cells and cancer cells based on morphological differences. Specifically, atypia is classified into two types, namely structural atypia (the cell population is not laid out in an orderly fashion on the basal membrane and does not form a glandular structure, etc.), and cellular atypia (disparate sizes of individual cells, unevenly located large nuclei, irregular polarity, etc.). With existing endoscopes it has been difficult to detect cancer sizes of about 5 millimeters in diameter, but by using a stain of the invention under a multiphoton laser microscope that allows imaging of cytomorphology, it is possible to accomplish early visual detection of cancer sizes of about 1 millimeter in diameter based on differences in morphology, without conducting biopsy tissue examination. Distinction between normal cells and cancer cells can be made not only by a physician but even by a cell laboratory technician, for example.

Stains that specifically stain normal cells compared to cancer cells under multiphoton laser microscopy observation stain normal mucosa more intensely than cancer lesion sites. Such staining specificity can likewise be utilized to allow confirmation of whether or not an observed site is a lesion site.

A stain that equally stains normal cells and cancer cells under multiphoton laser microscope observation may be used in combination with, for example, a stain that specifically stains cancer cells compared to normal cells under multiphoton laser microscopy observation, to allow further confirmation of a lesion site. When using only a stain that specifically stains cancer cells it is sometimes difficult to judge whether a stained site is indeed a cancer-affected site. Using a stain that specifically stains cancer cells compared to normal cells in combination with a stain that equally stains normal cells and cancer cells is advantageous as it can prevent false negative assessments.

Thus, the invention further provides a cocktail of a cell stain comprising a mixture of a cell stain that specifically stains cancer cells in contrast to normal cells, for observation under a multiphoton laser microscope, the cell stain comprising one or more dye compounds selected from the group consisting of meclocycline sulfosalicylate, methacycline hydrochloride, merbromin, Fast Green FCF, Red #3 (erythrosine) and Red #104, and a cell stain that equally stains normal cells and cancer cells, the cell stain comprising one or more dye compounds selected from the group consisting of pyrvinium pamoate, Chicago Sky Blue 6B, Acid Red and HI RED V80 (purple potato dye).

When cancers have been detected using the aforementioned stain under a multiphoton laser microscope, a multiphoton laser diagnosis and treatment apparatus of the invention as described below, for example, may be used to for removal of the cancer cells by burning and ablation by multiphoton laser irradiation. During the procedure, the coordinate axes of the image used for detection may be used directly to target on the cancer cells to be ablated, and then the laser power increased for irradiation of a high-power laser beam, allowing elimination of only the cancer cells as single units in a pinpoint manner. Generally speaking, the laser power for cellular imaging with the vital stain by multiphoton laser microscopy on a mucosal surface is sufficient at no greater than 3% (0.09 W), but for elimination of cancer cells, the laser power may be set to about 45% (1.35 W), and elimination can be accomplished with an irradiation time of about 2 seconds for clusters of several cancer cells, or about 10 seconds for clusters of several dozen.

During ablation of the cancer cells, laser irradiation does not need to be onto the whole cell, but instead the scanning zone of the multiphoton laser may be limited to only a portion of the cell membrane, to allow destruction of the cells by a smaller amount of light.

The quality of an image visualized by the stain of the invention is a sufficiently high image quality even compared to confocal laser microscope images with intravenous systemic administration of fluorescent dyes or multiphoton laser microscope images by autologous fluorescence without exogenous staining.

Dye compounds used for the invention may all be commercially available ones. There is no particular restriction on the content of the dye compound in the cell stain, and for example, the content may be 0.01 mg/ml to 1 mg/ml in the stain. The dye compound may be suitably used at a concentration of 0.1 µM to 10 µM. In addition to the dye compound, there may be included publicly known dyes such as iodine that have been used in the prior art for endoscopy and the like.

The dye compound of the invention will have characteristic fluorogenic activity, but in all cases is excited with a multiphoton laser emitting a long wavelength of 700 nm or greater and preferably 800 nm or greater. Observation of the excitation light may be carried out under multiphoton laser microscopy, and multiphoton laser microscopy allows real time histological diagnosis. The multiphoton laser used is not particularly restricted so long as it can emit long wavelength laser light.

There are no particular restrictions on the method of administering the stain, and for example, the stain of the invention may be directly administered to the lumen or administered submucosally, or it may be administered perorally, intravenously or intraperitoneally. When the stain has weak stainability, the mucosal surface is treated with pronase to remove the mucus, thereby improving the visibility of the cell structure. When the stain is to be directly applied to the inner surface of a lumen (for example, by coating or spraying), the dosage form is preferably liquid, although forms such as granules or tablets may also be used. Other appropriate added components that are necessary, including additives such as isotonizing agents, pH regulators, stabilizers, thickening agents, antiseptic agents, aromatics or pressure-sensitive adhesives, may be combined with the stain, depending on the dosage form and other factors. For example, pronase may be preadded to the stain of the invention.

The invention still further provides a method of evaluating the safety of an implant for regenerative medicine, since it is possible to judge the state of differentiation of pluripotent stem cells from the staining properties exhibited using a vital stain under multiphoton laser microscopy. Pluripotent stem cells such as iPS cells, ES cells or tissue-derived stem cells are considered promising for application and development in regenerative medicine, and for example, when a cell population is to be formed from iPS cells, differentiated into tissue cells that are destined to be transplanted, it is currently the case that iPS cell-derived differentiation-induced tissue cell populations partially contain undifferentiated cells that have not completely differentiated to the desired tissue cells, cells that have differentiated to cells other than the desired tissue cells, and the original iPS cells that have undergone essentially no differentiation. It has been pointed out that when such undifferentiated cells or original iPS cells are transplanted as is into the body, they can potentially become cancerated in the future. Thus, when an iPS cell-derived differentiation-induced tissue cell population is to be used for transplantation, undifferentiated cells or original iPS cells remaining in the transplanted cell population are preferably identified and confirmed, and also eliminated. If a stain could be found that allows judgment of the state of differentiation of pluripotent stem cells, including iPS cells, or the risk of canceration, by the method of the invention, then it would allow contamination by iPS cell-derived undifferentiated cells during transplantation to be prevented, and would be highly effective from the viewpoint of ensuring transplant safety. Pluripotent hepatocytes also have the staining properties of undifferentiated cells, and have been confirmed to exhibit undifferentiated cell staining by Red #104, for example.

In this method as well, it is preferred for the pluripotent stem cells to be labeled with a reporter gene. The reporter gene used may be the same type used for labeling of cancer cells as described above. Preferably, the reporter gene is functionally linked to a promoter for the pluripotent marker gene of the pluripotent stem cells, and is expressed together with the pluripotent marker gene. There are no particular restrictions on the pluripotent stem cell marker, and Nanog, Oct4, TRA-1-60, SSEA-3, AFP and the like may be mentioned as examples. In order to evaluate whether or not pluripotent stem cell-derived undifferentiated cells or normal differentiated cells are specifically stained, the reporter gene may be introduced into the pluripotent stem cells, and depending on the type of reporter gene, it may be determined whether the reporter gene is expressed in the normally differentiated cells, or whether the reporter gene is expressed only in undifferentiated cells, and comparison made with the staining by the stain. The method for expressing the reporter gene in normal differentiated cells may employ GFP as a reporter gene downstream from the promoter for a marker gene for normal differentiated cells, such as AFP (liver), Fox3 (nerves), betaIII-tubulin (nerves), neurofilament (nerves), Nkx2.5 (cardiac muscle), cTnt (cardiac muscle) or the like. The method for expressing the reporter gene in pluripotent stem cells and undifferentiated cells may also employ GFP as a reporter gene downstream from the promoter for a marker gene such as Nanog, Oct4, TRA-1-60, SSEA-3 or the like.

<Tumor Cell Stain>

The curcumin, sulfuretin and epigallocatechin gallate to be used as dye compounds for the invention are types of flavonoids. Erythrosine (Red #3) and Acid Red (Red #106) are known as tar-based dyes. All of the dye compounds are suitable for oral administration. These dye compounds are all strongly excited by multiphoton laser light and can provide bright living cell images. Also, the dye compounds have properties by which they preferentially intensely stain specific cell structures composing luminal organs such as in the gastrointestinal tract.

The cellular structures of the gastrointestinal tract mucosa can be classified into a cell group composed of epithelial cells covering the mucosal surface through which food passes and adenocytes where the epithelial cells are invaginated into an urn shape and secrete mucus (first series), and a cell group composed of capillaries and connective tissue cells that fill in the peripheries of the epithelial cells and adenocytes (second series). Curcumin, sulfuretin, epigallocatechin gallate and erythrosine can preferentially stain the first series cell group. Acid Red can stain both the first series and the second series cell group. The cytoarchitecture of the gastrointestinal tract mucosa observed under a microscope appears differently depending on the focal plane. Specifically, when an objective lens approaches the mucosal surface, epithelial cells are observed for the most part when the focus is directed onto the mucosal surface, while adenocytes and connective tissue and capillaries are observed when the focus is directed more deeply.

Furthermore, the dye compounds stain cancer lesion sites more intensely than normal mucosa. Such staining specificity can be utilized to allow rapid exploration of lesion sites. In particular, since cancer cells have different morphological characteristics from normal cells, it is possible to distinguish normal cells and cancer cells based on morphological differences. Specifically, atypia is classified into two types, namely structural atypia (the cell population is not laid out in an orderly fashion on the basal membrane and does not form a glandular structure, etc.), and cellular atypia (disparate sizes of individual cells, unevenly located large nuclei, irregular polarity, etc.). With existing endoscopes it has been difficult to detect cancer sizes of about 5 millimeters in diameter, but by using a stain of the invention under a multiphoton laser microscope that allows imaging of cytomorphology, it is possible to accomplish early visual detection of cancer sizes of about 1 millimeter in diameter based on differences in morphology, without conducting biopsy. Distinction between normal cells and cancer cells can be made not only by a physician but even by a cell laboratory technician, for example.

When cancer has been detected using a stain of the invention under multiphoton laser microscopy, it can be eliminated by burning with multiphoton laser irradiation. During the procedure, the coordinate axes of the image used for detection may be used directly and collimated with the cancer cells to be eliminated, and then the laser power increased for irradiation of a high-power laser beam, allowing elimination of only the cancer cells as single units in a pinpoint manner. Generally speaking, the laser power for cellular imaging by multiphoton laser microscopy on a mucosal surface is sufficient at no greater than 3% (0.09 W), but for elimination of cancer cells, the laser power may be set to about 45% (1.35 W), and elimination can be accomplished with an irradiation time of about 2 seconds for clusters of several cancer cells, or about 10 seconds for clusters of several dozen.

During elimination of the cancer cells, laser irradiation need not be onto the whole cell, but instead may be limited to only a portion of the cell membrane, to allow destruction of the cells by a smaller amount of light.

The quality of an image visualized by the stain of the invention is a sufficiently high image quality even compared to confocal laser microscope images with intravenous systemic administration of fluorescent dyes or multiphoton laser microscope images by autologous fluorescence without exogenous staining.

Dye compounds used for the invention may all be commercially available ones. For example, chemically synthesized pure curcumin or a turmeric extract containing curcumin may be used. Alternatively, it may be extracted from turmeric or the like by a known method. Curcumin and sulfuretin may each be used alone, or they may be used in combination to obtain different staining patterns. There is no particular restriction on the content, and for example, the content may be 0.01 mg/ml to 1 mg/ml in the stain. The dye compound may be suitably used at a concentration of 0.1 µM to 10 µM. In addition to the dye compound, there may be included publicly known dyes such as iodine that have been used in the prior art for endoscopy and the like.

The dye compounds of the invention will have characteristic fluorogenic activity, but in all cases are excited with a multiphoton laser emitting a long wavelength of 700 nm or greater and preferably 800 nm or greater. Observation of the excitation light may be carried out under multiphoton laser microscopy, and multiphoton laser microscopy allows real time histological diagnosis. The multiphoton laser used is not particularly restricted so long as it can emit long wavelength laser light.

The stain of the invention can be used for observation of cells in vitro, and the cells may be obtained by biopsy from a subject, or cultured cells (for example, monolayer culture cells). As used herein, the term "cultured cells" includes cultured products of various types of stem cells, such as induced pluripotent stem cells (iPS cells), MUSE cells, embryonic stem cells (ES cells) and tissue stem cells. The detection method of the invention can also be applied for detection and elimination of undifferentiated cells or cancerized cells, that are potentially generated when cells or ES cells are induced to differentiate and used to prepare transplant cells.

There are no particular restrictions on the method of administering the stain, and for example, the stain of the invention may be directly administered to the lumen or administered submucosally, or it may be administered perorally, intravenously or intraperitoneally. When the stain has weak stainability, the mucosal surface is treated with pronase to remove the mucus, thereby improving the visibility of the cell structure. When the stain is to be directly applied to the inner wall of a lumen (for example, by coating or spraying), the dosage form is preferably liquid, although forms such as granules or tablets may also be used. Other appropriate added components that are necessary, including additives such as isotonizing agents, pH regulators, stabilizers, thickening agents, antiseptic agents, aromatics or pressure-sensitive adhesives, may be combined with the stain, depending on the dosage form and other factors. For example, pronase may be preadded to the stain of the invention.

<Multiphoton Laser Diagnosis and Treatment Apparatus>

An embodiment of a multiphoton laser diagnosis and treatment apparatus according to the invention will now be explained with reference to the accompanying drawings.

First, the overall construction of a multiphoton laser diagnosis and treatment apparatus according to the invention will now be explained with reference to FIG. 1. The multiphoton laser diagnosis and treatment apparatus 11 comprises a laser oscillator 13, a beam diameter controller 15, a two-dimensional scanner 17, a dichroic mirror 19, an objective lens 21, a focal depth controller 23, a photodetector 25, a fluorescent image generating device 27, a monitor 29 and a controller 31.

The laser oscillator 13 emits ultra-short pulse laser light (hereunder referred to simply as "pulse laser light"), and allows adjustment of the intensity of the pulse laser light. The laser oscillator 13 used may be one that can adjust the output of the pulse laser light in a range for a pulse width of several dozen to several hundred femtoseconds and a pulse repeat frequency of several dozen to several hundred MHz. Also, the laser oscillator 13 may be one that can output pulse laser light of 3.2W at a wavelength of 800 nm, for example. The pulse laser light is preferably able to be output in a wavelength range of 680 to 1100 nm, for example. In the multiphoton absorption phenomenon, photons having wavelengths that are half the wavelength of the incident photon are produced, and therefore pulse laser light with a wavelength of 800 nm or longer is preferably used in order to prevent production of photons in the ultraviolet ray region (wavelength of <400 nm) that are harmful to the human body.

The beam diameter controller 15 is constructed so as to vary the beam diameter of the pulse laser light according to the beam diameter control signal from the controller 31. A beam expander, for example, may be used as the beam diameter controller 15.

The two-dimensional scanner 17 moves the focal point of the ultra-short pulse laser light with respect to the target site of the patient, in the biaxial direction perpendicular to the optical axis, based on a driving signal from the controller 31. The two-dimensional scanner 15 is composed of two galvano mirrors, for example, and two-dimensional scanning is accomplished by swinging around two mutually orthogonal optical axes, based on a driving signal.

The dichroic mirror 19 is provided to separate the fluorescence generated in patient tissue by irradiation of the pulse laser light. The mirror used has a property of reflecting light of the same wavelength as pulse laser light irradiated onto patient tissue, while transmitting light of other wavelengths. Thus, the pulse laser light sent from the two-dimensional scanner 17 is reflected by the dichroic mirror 19 toward the objective lens 21, while fluorescence generated in the tissue is transmitted through the dichroic mirror 19. In this manner, fluorescence generated in the tissue becomes separated by the dichroic mirror 19.

The objective lens 21 focuses pulse laser light directed from the two-dimensional scanner 17 and reflected by the dichroic mirror 19, to the focal points of the patient tissue, while also focusing fluorescence generated in the patient tissue by the multiphoton absorption phenomenon and directing it toward the dichroic mirror 19. The objective lens 21 is movable in the optical axis direction by the focal depth controller 23, based on a control signal, allowing adjustment of the focal points. The dichroic mirror 19 and objective lens 21 form an optical system that includes the optical path between them. Also, the two-dimensional scanner 17 and the focal depth controller 23 are parts of a focal point displacing device.

In order to produce multiphoton absorption in tissue, it is necessary to increase the photon density to a degree such that numerous photons simultaneously impact with the target. Consequently, since it is easy to create a high photon density state even with low-intensity pulse laser light, it is preferred to use an objective lens 21 with a large numerical aperture. Also, since a high photon density state sufficient to produce the multiphoton absorption phenomenon is only created at the focal point, the multiphoton absorption phenomenon only occurs at the focal point and not in the other regions. If an objective lens 21 with a large numerical aperture is used, the region in which the multiphoton absorption phenomenon occurs can be extremely reduced, thereby allowing selective destruction of cellular units. The numerical aperture of the objective lens 21 is preferably 0.6 or greater, and even more preferably is 1.0 or greater in order to allow destruction of cellular units.

The photodetector 25 detects fluorescence produced in tissue, and converts it to an electrical signal corresponding to the fluorescence intensity. The photodetector 25 used may be a photomultiplier tube (PMT) or the like.

The scanning state of the two-dimensional scanner 17 and the control position of the focal depth controller 23 (the position in the depthwise direction) are the parameters representing the coordinates of the focal point, and the fluorescent image generating device 27 matches the parameters representing these coordinates and the electrical signal sent from the photodetector 25 (i.e. the fluorescence intensity) and records them, processing the data to produce a fluorescent image. The fluorescent image that is produced is displayed on the monitor 29.

The controller 31 includes an operating controller 33, a diagnostic pulse intensity setting adjuster 35, a treatment pulse intensity setting adjuster 37, an irradiation range setting adjuster 39 and an irradiation time setting adjuster 41. The operating controller 33 controls operation of the laser oscillator 13, the beam diameter controller 15, the two-dimensional scanner 17 and the focal depth controller 23. The diagnostic pulse intensity setting adjuster 35 sets the pulse laser light intensity so that the laser oscillator 13 outputs pulse laser light of an intensity suitable for obtaining a fluorescent image of patient tissue for diagnosis, while the treatment pulse intensity setting adjuster 37 sets the pulse laser light intensity so that the laser oscillator 13 outputs pulse laser light of a sufficient intensity for destruction of patient tissue for treatment (which is greater than the pulse laser light intensity for diagnosis). The pulse laser light intensities set by the diagnostic pulse intensity setting adjuster 35 and the treatment pulse intensity setting adjuster 37 may be preset values, or instead, input means (not shown) such as a keyboard or the like, may be used for appropriate setting by the user. The irradiation range setting adjuster 39 sets the range for irradiation of pulse laser light of a pulse laser light intensity for treatment onto patient tissue, and by controlling operation of the two-dimensional scanner 17 and focal depth controller 23 by the operating controller 33, pulse laser light of the pulse laser light intensity for treatment is irradiated and focused within the set irradiation range at the set depth. The irradiation range set by the irradiation range setting adjuster 39 may be set by specifying a range using input means (such as a mouse) (not shown) by the user, on a fluorescent image that is taken by irradiation of pulse laser light of a pulse laser light intensity for diagnosis onto patient tissue, and that is displayed on a monitor 29. The fluorescence irradiation time setting adjuster 41 sets the time for irradiation of the pulse laser light of the pulse laser light intensity for treatment within the irradiation range of patient tissue, and by controlling the output of the laser oscillator 13 via the operating controller 33, pulse laser light of the pulse laser light intensity for treatment is irradiated only for the set time period, within the irradiation range set by the irradiation range setting adjuster 39. The irradiation time set by the irradiation time setting adjuster 41 may be a preset value, or instead, input means (not shown) such as a keyboard or the like, may be used for appropriate setting by the user.

Figure 2:
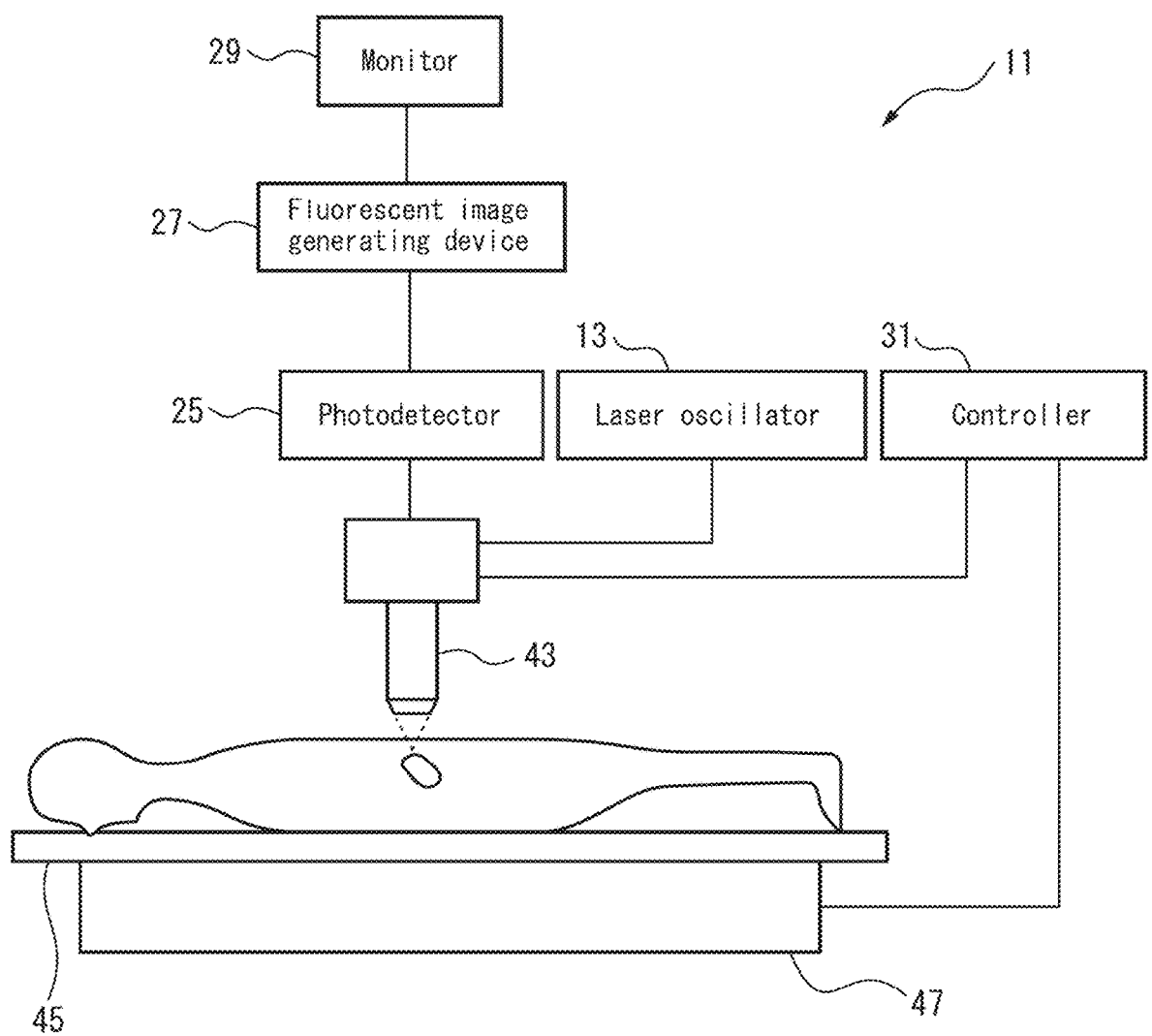
FIG. 2 is an overview block diagram showing a multiphoton laser diagnosis and treatment apparatus according to the first illustrated embodiment of the invention.
Figure 3:
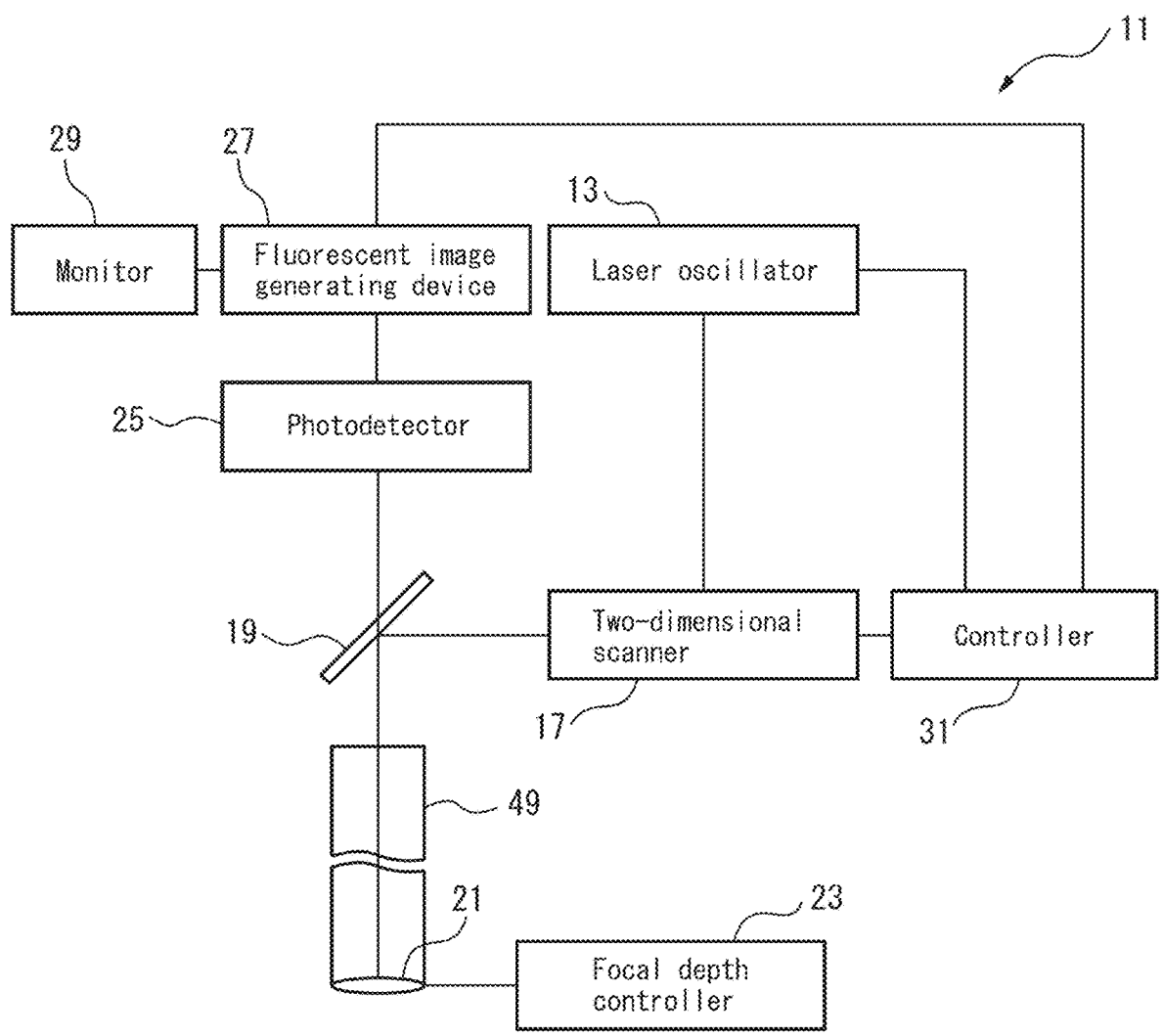
FIG. 3 is an overview block diagram showing a multiphoton laser diagnosis and treatment apparatus according to the second illustrated embodiment of the invention.

The multiphoton laser diagnosis and treatment apparatus 11 of the invention may be implemented in a variety of modes. For example, as shown in FIG. 2, in the laser light irradiating head 43 there are provided the beam diameter controller 15, two-dimensional scanner 17, the dichroic mirror 19 and objective lens 21 and the optical system formed by the optical path between them, and the focal depth controller 23, while there are further provided a patient immobilizing platform 45 for placement of the patient, and a moving apparatus 47, the laser light irradiating head 43 and the patient immobilizing platform 45 being movable relative to each other by the moving apparatus 47. Thus, if the design is such that the laser light irradiating head 43 and the patient immobilizing platform 45 can be relatively moved independently in the 3 axial directions, irradiation of laser light near the affected area of the patient is facilitated. Also, as shown in FIG. 3, part of the optical path between the dichroic mirror 19 and the objective lens 21 may be replaced by an endoscope 49 and the objective lens 21 and focal depth controller 23 may be situated at the tip of the endoscope 49. With such a construction, it is possible to perform cancer diagnosis and treatment of in vivo sites by low-invasive endoscopic surgery, and to thus reduce the physical burden on patients.

Figure 4:
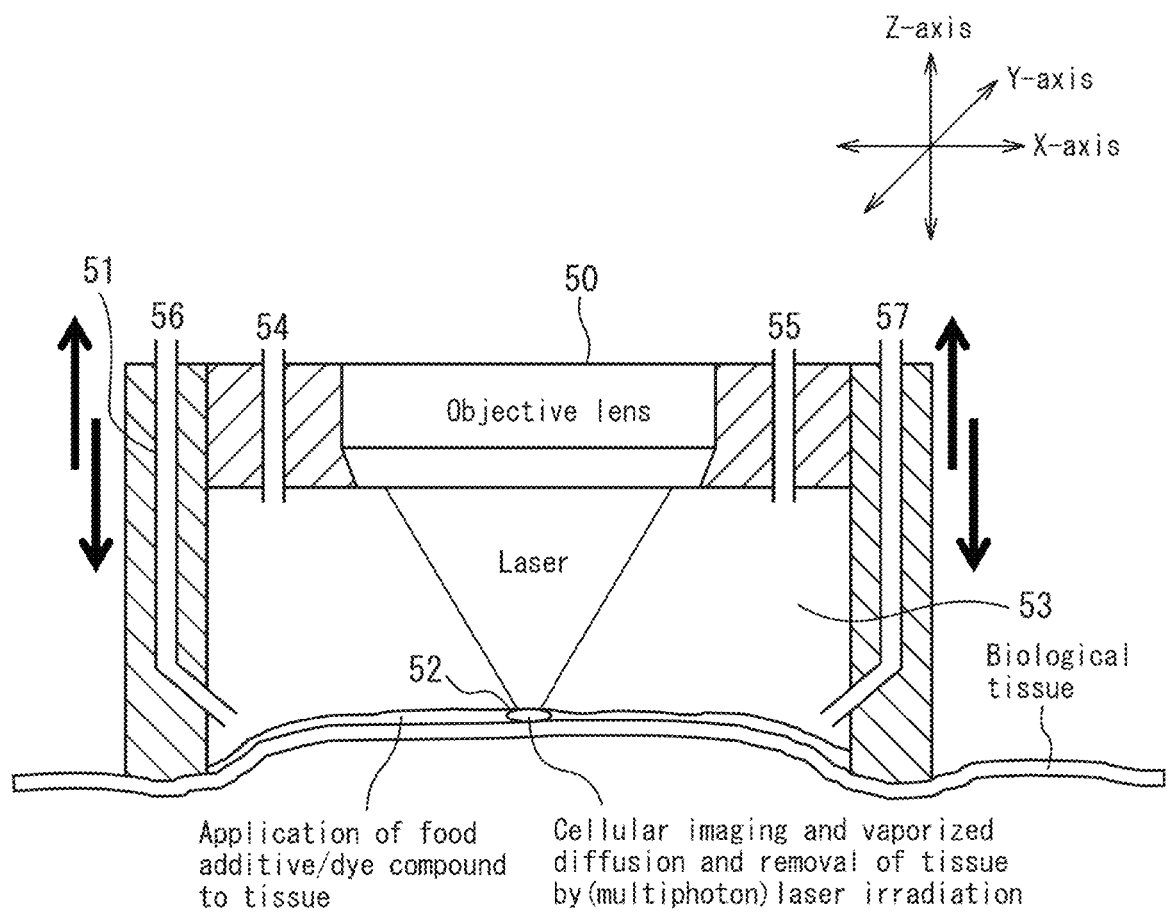
FIG. 4 shows a state where the optical system of a multiphoton laser diagnosis and treatment apparatus of the invention is surrounded by a shield member.

FIG. 4 shows the details of an optical system that includes the objective lens 21 of FIG. 1. In FIG. 4, the periphery of the objective lens 50 is covered by a tubular shield member 51, the shield member forming a space 53 for encapsulation of the optical system by contact bonding onto the perimeter of the tissue 52 to be observed. The shield member also comprises vent holes 54, 55 for adjustment of the pressure in the space. The vent holes 54, 55 are, for example, connected to aspiration means such as a vacuum pump, and the interior of the space is brought to a negative pressure to increase adhesiveness between the shield member and the tissue, so that as a result it is possible to maintain the relative positional relationship of the objective lens and the observed tissue even with slight movement by the patient, and thus prevent image blurring and the like. Upon completing the imaging and operation, the vent holes 54, 55 may be released to restore the negative pressure state in the space interior to normal pressure, and the optical system 50 may be detached from the tissue. There may be provided one or a plurality of vent holes 54, 55, and when they are a plurality, one may be permanently connected to the aspiration means while the other vent hole is opened and closed to facilitate adjustment of the air pressure in the space.

Preferably, the shield member further comprises a fluid supply inlet 56 and a fluid drainage outlet 57, for supply and drainage of the staining solution containing the stain used for staining of the tissue in the space, and a cleaning fluid for cleaning of the staining solution. The fluid supply inlet 56 and fluid drainage outlet 57 may be identical or different, and the fluid supply inlet 56 and fluid drainage outlet 57 may even serve as the vent holes 54, 55. According to a preferred embodiment, the staining solution is introduced into the space through the fluid supply inlet 56 and stains tissue, after which the staining solution is drained through the fluid drainage outlet 57 and, if necessary, a cleaning fluid is introduced into the space through the same or a different fluid supply inlet 56 and drained through the same or a different fluid drainage outlet 57, thereby cleaning the tissue.

There are no particular restrictions on the material of the sealing member, and it may be synthetic rubber, natural rubber, fluorine rubber, urethane rubber, silicone rubber, epoxy resin, silicone resin, phenol resin, melamine resin, urea resin, polyamide resin, polyimide resin, polyurethane resin, polyphenyl sulfide resin, polybutylene terephthalate resin, polyamideimide resin or the like. Preferably it is an elastic elastomer such as synthetic rubber, natural rubber, fluorine rubber, urethane rubber or silicone rubber, in order to increase adhesiveness between the shield member and the tissue. The objective lens 50 in FIG. 4 is shown anchored to the top side of the shield member 51, but adjustment may instead be accomplished electromagnetically. For electromagnetic adjustment, the section between the objective lens anchoring part of the shield member and the objective lens may be supported by an elastic member such as rubber or a spring, and adjustment accomplished by placement of an actuator employing a magnet or coil, with 3 axial directions, i.e. the X-axis (a first horizontal direction perpendicular to the optical axis), the Y-axis (second horizontal direction perpendicular to the optical axis and the first horizontal) and the Z-axis (the optical axis direction). By adding an actuator in this manner it is possible to effect external control by electric current, allowing the examination, analysis and ablation procedures to be carried out with higher precision and in a wider range. The two-dimensional scanner 17 shown in FIG. 3 may be used to change the position of the objective lens, and the actuator may be used to control scanning in the shield member. The actuator need not have 3 axes, and is effective if it has at least one axis.

Figure 5:
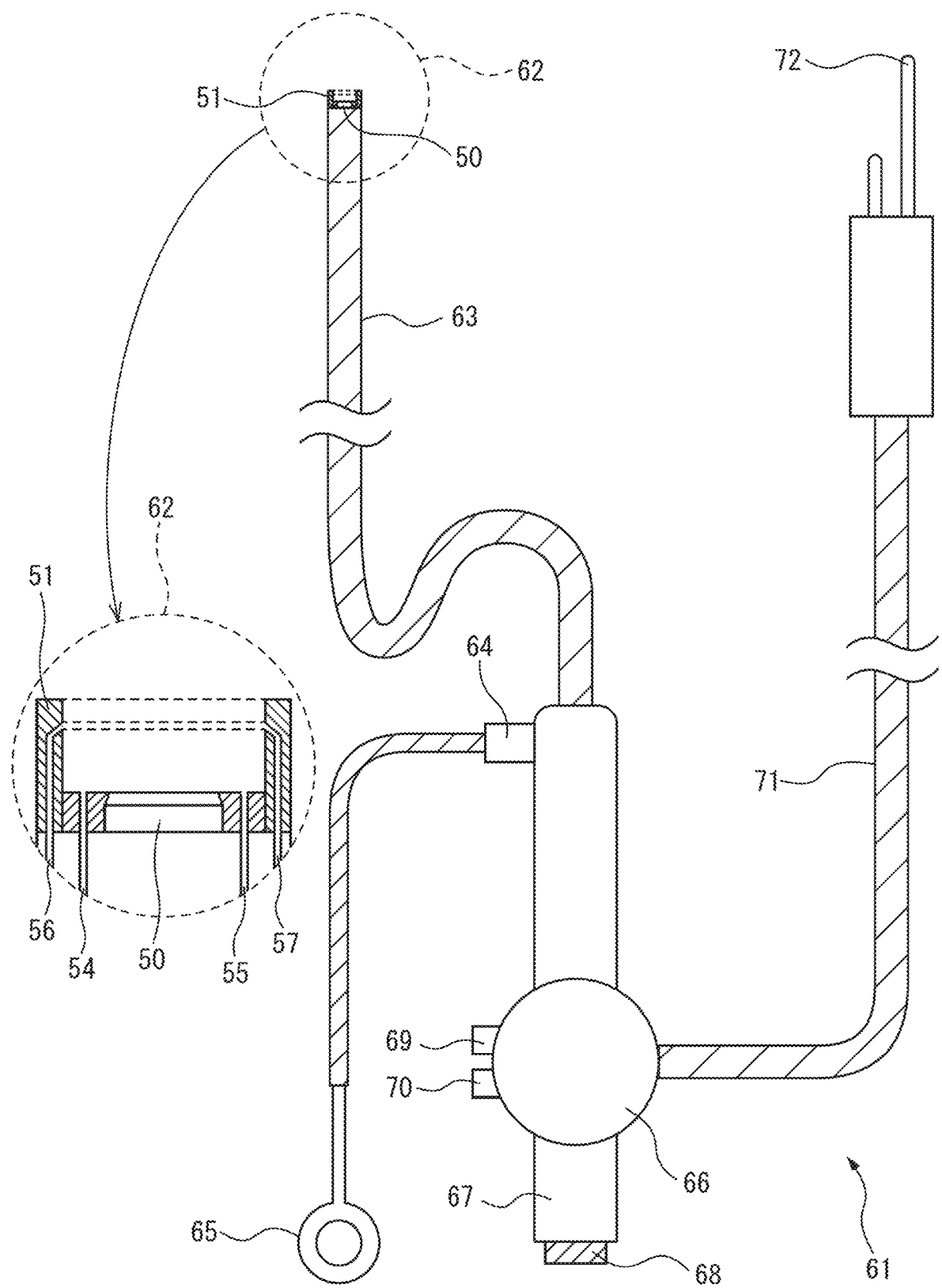
FIG. 5 shows an endoscope wherein the optical system is surrounded by a shield member.

FIG. 5 shows an endoscope 61 where the periphery of an optical system is covered by a tubular shield member 51. In FIG. 5, 63 denotes an insertion member having a flexible structure for smooth passage through digestive organs. For simplicity, 64 denotes a forceps hole, 65 denotes forceps, and 66 denotes a right-left, up-down angle knob actuator. The numeral 67 denotes an eyepiece for visibility adjustment, 68 denotes an eyepiece lens, 69 denotes an air supply and water supply actuator, 70 denotes an aspiration actuator, 71 denotes a connector for a tester body (not shown), and 71 denotes a light guide, the construction being such as to allow an air supply inlet, stain insertion opening, stain aspiration opening and the like in their vicinity to be connected to the tester body. If the periphery of the objective lens is covered by the tubular shield member 51 in the optical system 50 at the tip section 62 of the endoscope, the shield member will contact bond with the perimeter of the tissue to be observed, forming a space for encapsulation of the optical system, as explained in relation to FIG. 4 (53 of FIG. 4), while as also explained in relation to FIG. 4, the shield member of the endoscope 61 is provided with vent holes 54, 55 connected to aspiration means of the endoscope for adjustment of the pressure inside the space, allowing negative pressure to be created in the space and allowing increase in adhesiveness between the shield member and the tissue, and as a result, it is possible to maintain the relative positional relationship of the objective lens and the observed tissue even with slight movement by the patient, and thus prevent image blurring and the like during examination and operation with the endoscope. Upon completing the imaging and operation, the vent holes 54, 55 may be released to restore the negative pressure state in the space interior to normal pressure, and the optical system 50 may be detached from the tissue. This procedure may be carried out with operating buttons gathered on the air supply and water supply actuator 69 and the aspiration actuator 70, and since the staining operation is also a preparation process, it differs from imaging of the affected area and the surgical procedure of ablation and removal, and may be carried out with an operating button provided on the tester body side. By using such an endoscope, it is possible to discover pathological tissues such as cancers and surgically remove it with better accuracy than by conventional endoscopic surgery.

Operation of the multiphoton laser diagnosis and treatment apparatus 11 shown in FIG. 1 will now be described.

First, during diagnosis, pulse laser light is outputted from the laser oscillator 13 at a pulse laser light intensity set by the diagnostic pulse intensity setting adjuster 35 of the controller 31, and it is adjusted to the prescribed beam diameter by the beam diameter controller 15 according to an operation command from the operating controller 33 of the controller 31. The pulse laser light that has been adjusted to the prescribed beam diameter is controlled for two-dimensional scanning of a prescribed region by the two-dimensional scanner 17, based on the operation command from the operating controller 33 of the controller 31, while being guided to the dichroic mirror 19 and reflected toward the objective lens 21. The focal point of pulse laser light focused by the objective lens 21 is scanned over a two-dimensional plane at a prescribed depth in the patient tissue. The focal point of the pulse laser light is adjusted to a predetermined depth in the patient tissue, according to a command from the operating controller 33 of the controller 31.

The multiphoton absorption phenomenon takes place at the focal point in the patient tissue, and fluorescence is excited. Flavin in the patient cells can be excited to emit fluorescence, but the obtained fluorescence intensity is weak and the fluorescent image has low contrast. Therefore, in order to increase the contrast of the obtained fluorescent image, preferably the surface of the tissue is pre-stained with a stain, and the stained dye is excited to emit fluorescence. Also, when a stain is applied to the surface of affected tissue of a patient, and the multiphoton absorption phenomenon is utilized to obtain a fluorescent image after staining, the intensity of the fluorescence emitted from the dye molecules of the stain by the multiphoton absorption phenomenon is higher than the intensity of fluorescence emitted from intracellular flavin by the multiphoton absorption phenomenon, and therefore a clearer image can be obtained with pulse laser light of low intensity. The pulse laser light intensity for diagnosis can therefore be set to a lower value. Specifically, when a fluorescent image is obtained after applying a stain to the surface of tissue, it is possible to obtain a fluorescent image of comparable level to a fluorescent image obtained without application of a stain, at a pulse laser light intensity of 1/10 the pulse laser light intensity or lower. This allows adverse effects of pulse laser light on patient tissue to be kept to a minimum.

The stain used may be an approved fluorescent agent such as fluorescein, indocyanine green (ICG) or indigo carmine, but highly safe food colorings and the like are preferred for use in the human body. Erythrosine, curcumin, epigallocatechin gallate, sulfuretin, Acid Red and the like may be mentioned as examples where the present inventors have found that particularly clear images are obtained.

Since the dichroic mirror 19 has the property of reflecting light of the same wavelength as the pulse laser light irradiated onto the patient tissue while transmitting light of other wavelengths, it reflects the reflected pulse laser light of the incident light while transmitting the fluorescence emitted from the tissue, thereby separating the fluorescence. The separated fluorescence enters the photodetector 25 and is detected, being converted to an electrical signal of a size corresponding to the intensity. The fluorescent image generating device 27 produces a fluorescent image by matching the focal point data based on the converted electrical signal and the operating states of the two-dimensional scanner 17 and the focal depth controller 23, and displays it on the monitor 29.

For treatment, on the other hand, pulse laser light is outputted from the laser oscillator 13 at a pulse laser light intensity set by the treatment pulse intensity setting adjuster 37 of the controller 31, and it is adjusted to the prescribed beam diameter by the beam diameter controller 15 according to an operation command from the operating controller 33 of the controller 31. The pulse laser light intensity for treatment is a sufficient height to allow destruction in the tissue at the focal point of the pulse laser light by the multiphoton absorption phenomenon, and it is set to be higher than the pulse laser light intensity for diagnosis. The pulse laser light that has been adjusted to the prescribed beam diameter is controlled for scanning of the irradiation range set by the irradiation range setting adjuster 39 of the controller 31, by the two-dimensional scanner 17 based on the operation command from the operating controller 33 of the controller 31, while being guided to the dichroic mirror 19 and reflected toward the objective lens 21. The pulse laser light focused by the objective lens 21 is such that the focal point scans the irradiation range set by the irradiation range setting adjuster 39, on a two-dimensional plane at the prescribed depth in the patient tissue. The focal point can be controlled by the focal depth controller 23, which is controlled by the operating controller 33 of the controller 31. By irradiating pulse laser light on the desired irradiation range in this manner, cells of the tissue in the irradiation range are destroyed and cancer cells are eliminated.

Here, the tissue or cells are destroyed by the multiphoton absorption phenomenon because the intracellular molecules become ionized by the multiphoton absorption phenomenon, generating plasma, thereby causing destruction of the cell membrane.

During treatment, the tissue or cells are destroyed by the multiphoton absorption phenomenon produced in the tissue or cells at the focal point. Thus, it is necessary to expose the tissue or cells to sufficient energy to allow their destruction. For this purpose, the irradiation time is set by the irradiation time setting adjuster 41 of the controller 31 depending on the intensity of the pulse laser light being irradiated, and is controlled by the operating controller 33 of the controller 31 so that the irradiation range is irradiated for only the set time. The irradiation time may be selected from among predetermined values in the irradiation time setting adjuster 41, or the user may set it to an appropriate value by input to the irradiation time setting adjuster 41.

Since the multiphoton absorption phenomenon can be controlled in cellular units by using an objective lens with a large numerical aperture, it is possible to obtain a high-resolution fluorescent image of tissue of the affected area of the patient during diagnosis, thus facilitating distinction of normal tissue in contrast to even small clusters of cancer cells or cancer tissues. This renders it easier to discover cancer cells or cancer tissue. Furthermore, if the pulse laser light is irradiated at the set pulse laser light intensity for treatment in the irradiation range onto the cancer lesion site that has been discovered on the fluorescent image, matching the operating state of the two-dimensional scanner 17 and focal depth controller 23, and the detected fluorescence intensity, at the time the fluorescent image has been obtained during diagnosis, it is possible to accurately destroy the cancer lesion site in the designated irradiation range. Moreover, since using an objective lens with a large numerical aperture allows the irradiation of pulse laser light to be carried out in a range with a size smaller than a unit cell, this allows destruction of cellular units.

A procedure for diagnosis and treatment of cancer using a multiphoton laser diagnosis and treatment apparatus 11 that employs a laser oscillator 13 with a peak output of 3.2W at a wavelength of 800 nm, and an objective lens 21 with a numerical aperture of 1.05, will now be explained.

It is preferred for the stain to be applied beforehand to the surface of tissue of the patient that is to be diagnosed. Applying the stain to the surface of tissue stains cancer lesion tissues more intensely with the dye than normal tissue and increases the difference in fluorescence between the normal tissue and the cancer lesion tissues, thereby facilitating discovery of the cancer lesion sites. This is thought to be because in normal tissue, cellular adhesion is strong and there are virtually no intercellular gaps, whereas in a cancer lesion site, the adhesion between cells is weak and intercellular gaps are numerous, such that the stain can easily pool in the gaps. The stain used is preferably a food coloring that is highly safe for the human body, and examples of stains that may be used that produce especially notable differences in fluorescence between normal tissue and cancer lesion tissue include erythrosine, curcumin, epigallocatechin gallate, sulfuretin and Acid Red.

Next, pulse laser light outputted from the laser oscillator 13 at the pulse laser light intensity set by the diagnostic pulse intensity setting adjuster 35 of the controller 31 is focused onto the focal point in the tissue of the affected area of the patient by the objective lens 21, and the focal point is scanned by the two-dimensional scanner 17 on the two-dimensional plane perpendicular to the optical axis. The focal point in the tissue can be adjusted to various depths by control of operation of the focal depth controller 23 by the operating controller 33 of the controller 31. The fluorescence obtained by irradiating the patient tissue with pulse laser light to produce a multiphoton absorption phenomenon in this manner is detected by the photodetector 25, and a fluorescent image can be obtained if processing is performed matching the parameters that indicate the focal point (i.e., coordinates), obtained from the intensity of the detected fluorescence and the states of the two-dimensional scanner 17 and the focal point depth controller 23, after which the obtained fluorescent image is displayed on a monitor 29.

A physician can judge the presence of cancer cells or tissues from the fluorescent images on the monitor 29, based on differences in the fluorescent image forms of cancer cells and normal cells, and can make a diagnosis. The present inventors have found that when a fluorescent image is obtained after applying a stain on the surface of tissue to stain the tissue, cancer lesion tissue is stained more intensely than normal tissue, and stronger fluorescence is obtained. This is thought to be because in normal tissue, cellular adhesion is strong and there are virtually no intercellular gaps, whereas in a cancer lesion site, the adhesion between cells is weak and intercellular gaps are numerous, such that the stain can easily pool in the gaps. Utilizing this fact, cancer lesion tissue will emit stronger fluorescence than normal tissue, thereby facilitating discovery of the difference between normal tissue and cancer lesion tissue based on comparison of the fluorescence intensity, and facilitating diagnosis. Also, since the dye molecules of a stain emit fluorescence of higher intensity than intracellular flavin, due to the multiphoton absorption phenomenon, using a stain allows more distinct fluorescent images to be obtained using low-intensity pulse laser light, compared to not using a stain. The pulse laser light intensity for diagnosis can therefore be set to a lower value.

Specifically, when a fluorescent image is obtained after applying a stain to the surface of tissue, it is possible to obtain a fluorescent image of comparable level to a fluorescent image obtained without application of a stain, at a pulse laser light intensity of 1/10 the pulse laser light intensity or lower. For example, when fluorescent image diagnosis and treatment are to be conducted using a laser oscillator 13 with an output of 3.2W and an objective lens 21 with a numerical aperture of 1.05, the value set for the pulse laser light intensity for treatment is 50% of the maximum output whether or not dye staining is to be performed with a stain, but the value set for the pulse laser light intensity for diagnosis is 20% when dye staining is not to be performed, and no greater than 3% (about 1%) when dye staining is to be performed, in order to obtain equivalent fluorescent images.

In addition, when it is attempted to detect fluorescence from intracellular flavin, the wavelength of the irradiated pulse laser light must be around 735 nm, and therefore the wavelength of the generated fluorescence is about 370 nm, which corresponds to ultraviolet rays that carry the risk of cellular DNA damages. In contrast, staining with a stain allows generation of fluorescence with pulse laser light having a wavelength of 800 nm or longer, thus also providing the advantage of minimizing generation of ultraviolet rays.

When a cancer lesion site has been identified by a physician, the multiphoton absorption phenomenon is used to destroy the cancer cells at the identified cancer lesion site. Specifically, the irradiation range is set at the irradiation range setting adjuster 39, by designating the desired treatment region on the fluorescent image displayed on the monitor 29, and control by the focal depth controller 23 is carried out so that the depth is the same as the focus depth when the fluorescent image was taken, the pulse laser light outputted from the laser oscillator 13 at the pulse laser light intensity set by the treatment pulse intensity setting adjuster 37 of the controller 31 is focused onto the focal point of the patient tissue, and scanning is performed by the two-dimensional scanner 17 so that the set irradiation range is irradiated only for the time set by the irradiation time setting adjuster 41 of the controller 31. When the pulse laser light intensity for treatment has been set to 50% of the maximum output, destruction can be accomplished by irradiation for about 2 seconds for several cells, or irradiation for about 10 seconds for clusters of several dozen cells.

If pulse laser light of the pulse laser light intensity for treatment, which is higher than the pulse laser light intensity for diagnosis, is focused onto the focal point by the objective lens 21, the tissue or cells are destroyed by the multiphoton absorption phenomenon in the tissue at the focal point. Furthermore, since irradiating pulse laser light of the pulse laser light intensity for treatment in the region designated on the fluorescent image used during diagnosis results in destruction of the tissue or cells in that region, it is possible to accurately destroy the cancer lesion site in the designated region. Moreover, since using an objective lens 21 with a large numerical aperture allows the irradiation of pulse laser light to be carried out in a range with a size smaller than a unit cell, this allows destruction of cellular units.

After treatment, preferably the stain is again applied onto the surface of the tissue of the treatment site and pulse laser light is irradiated onto the tissue of the treatment site at the pulse laser light intensity set by the diagnostic pulse intensity setting adjuster 35, and the generated fluorescence is detected, to produce a fluorescent image and confirm based on the produced fluorescent image that the cancer lesion site has been destroyed and eliminated.

When staining of tissues with a stain has not been performed, the pulse laser light intensity for diagnosis must be at least 20% of the maximum output of the pulse laser light, resulting in a smaller difference from the pulse laser light intensity for treatment (about 50% of maximum output), and when pulse laser light irradiation is carried out twice, for confirmation and for diagnosis, the exposure dose of the pulse laser light on normal cells in the periphery of the cancer lesion site increases, raising the possibility of causing photodamage to normal cells as well. In contrast, if staining of tissues with a stain is carried out, the pulse laser light intensity for diagnosis can be 3% of the maximum output of the pulse laser light or lower, thus significantly reducing the potential for photodamage to normal cells.

The multiphoton laser diagnosis and treatment apparatus 11 of the invention was explained above with reference to the illustrated embodiments, but the invention is not limited to these embodiments. For example, the irradiation time for pulse laser light during diagnosis in the controller 31 may be set by the user.

The function of the multiphoton laser diagnosis and treatment apparatus 11 of the invention by which it can destroy multiple cancer cells in tissues may be utilized during the course of culturing of iPS cells, ES cells and tissue stem cells for regenerative medicine applications, for quality control of transplant cells by detection and elimination of cancerized cells or undifferentiated cells.

Concrete examples will now be provided for a more detailed explanation of the invention. However, the invention is in no way limited by the examples.

Example 1

1. Evaluation of Dye Compound Stainability

Drinking water containing 2% (w/v) dextran sodium sulfate (DSS) was given to 8-week-old C57B6 mice (male, approximately 20 g) for 7 days. After intraperitoneal injection of 0.2 ml of 5% chloral hydrate for anesthesia, the mouse abdominal wall was incised vertically to about 1 cm, and the gastrointestinal tract was raised over the abdominal wall to about 1 cm. Blood flow to the gastrointestinal tract was maintained during this time by the blood vessel flowing into the mesenteric attachment site. The gastrointestinal tract was incised vertically to about 1 cm on opposite side of the mesenteric attachment site, including the tunica muscularis and mucosa. The opposite side of the mesenteric attachment site was incised in order to prevent severance and damage of the blood vessel and minimize bleeding. When the incision site of the gastrointestinal tract was opened vertically, the mucosal surface of the gastrointestinal tract, as the food channel, became visible. When food digestion products were present they were wiped off with tissue paper.

In order to more clearly observe the gastrointestinal tract mucosal surface, a 1% pronase solution was dropped onto the mucosal surface and was allowed to stand still for 15 minutes. This pronase treatment removed the mucus from the mucosal surface, rendering the cell structure more easily visible. Next, the pronase was removed from the mucosal surface and rinsed with physiological saline (PBS).

A metal ring (outer diameter: 16 millimeters, inner diameter, 6 millimeters) was placed on a laboratory stage, and a rapid bonding adhesive (AronAlpha) was coated over the entire periphery of the ring surface on one side. Forceps were used to hold the rapid bonding adhesive-coated metal ring with the adhesive-coated surface facing downward, and it was set on the pronase-treated mucosal surface. During a period of about 5 minutes, the metal ring became anchored to the mucosa with the rapid bonding adhesive, and the region where the dye compound was to be applied was rinsed with PBS.

In order to avoid drying of the mucosal surface, a curcumin stock solution or sulfuretin stock solution diluted with physiological saline (PBS) (see Tables 1 to 3 for the dilution factors) was added dropwise onto the pronase-treated mucosal surface, and after allowing it to stand for 1 minute, it was rinsed 3 times with PBS, a cover glass was placed over the metal ring, and the objective lens of a multiphoton laser microscope (FV1000 MPE by Olympus Corp.) was brought near to the top of the cover glass for image observation.

The conditions used to evaluate the dye compound, and the evaluation results, are shown in the following tables.

TABLE 1

| | Exo vivo Large intestine | Small intestine | Stomach | Esophageal | Excitation wavelength | Concentration used |
|---|---|---|---|---|---|---|
| Red #3 | F | VG 0.1 mg/ml | | | 800 nm | 0.1 mg/ml |
| Red #104 | G 0.01 mg/ml Surface only. Invisible at high concentration. | VG Appeared as caliciform cells at 1.0 mg/ml, 0.01 mg/ml | | | 820 nm | 1 mg/ml |
| Red #105 (720 nm) | F 1.0 mg/ml Faintly stained epithelium. | F | | | 720 nm | 1 mg/ml |
| Red #105 (860 nm) | G 1.0 mg/ml cell membrane Appeared as caliciform cells at 0.1 mg/ml. Blood vessels visible even at low concentration. | G 1.0 mg/ml Stained epithelium | | | 860 nm | |

TABLE 1-continued

| Dye | Col2 | Col3 | Col4 | Col5 |
|---|---|---|---|---|
| Red #106 | VG<br>0.1 mg/ml Cell membrane.<br>Appeared as caliciform cells.<br>Blood vessels visible even at low concentration. | VG<br>0.1 mg/ml<br>Visible to muscle layer | 840 nm | 0.1 mg/ml |
| Green #3<br>Fast Green FCF | G<br>Caliciform cells | | 800 nm | 1 mg/ml |
| Red #2 | F | | | |
| Red #102 | G | | | |
| Blue #2<br>Indigo carmine | G | | | |
| Yellow #4<br>Tartrazine | F | | | |
| Yellow #5<br>Sunset Yellow FCF | G | | | |
| Haimeron P-2<br>(Gardenia Blue:<br>geniposide + yellow<br>dye: crocin) | | | | |
| HI RED G150<br>(Grape peel dye,<br>anthocyanin) | F | | | |
| Annatto<br>(Annatto N2R25,<br>achiote fruit:<br>bixin, norbixin) | F | | | |
| Crocin G150<br>(Gardenia Yellow<br>dye) | F | | | |
| Crocin L<br>(Gardenia Yellow<br>dye) | F | | | |

| | Stock concentration | Stock solvent | LD50 | | |
|---|---|---|---|---|---|
| Red #3 | | PBS | 6800 mg/kg | Mouse | Oral |
| Red #104 | | PBS | 310 mg/kg | Mouse | Intra-abdominal |
| Red #105 (720 nm) | | PBS | 6480 mg/kg | Mouse | Oral |
| Red #105 (860 nm) | | | | | |
| Red #106 | | PBS | >20,000 mg/kg | Mouse | Oral |
| Green #3<br>Fast Green FCF | | PBS | >2000 mg/kg | Rat | Oral |
| Red #2 | | | 1000 mg/kg | Mouse | Intra-abdominal |
| Red #102 | | | >8000 mg/kg | Mouse | Oral |
| Blue #2<br>Indigo carmine | | | 2000 mg/kg | Mouse | Oral |
| Yellow #4<br>Tartrazine | | | 12750 mg/kg | Mouse | Oral |
| Yellow #5<br>Sunset Yellow FCF | | | >6000 mg/kg | Mouse | Oral |
| Haimeron P-2<br>(Gardenia Blue:<br>geniposide + yellow<br>dye: crocin) | | | | | |
| HI RED G150<br>(Grape peel dye,<br>anthocyanin) | | | | | |
| Annatto<br>(Annatto N2R25,<br>achiote fruit:<br>bixin, norbixin) | | | 700 mg/kg | Mouse | Intra-abdominal |
| Crocin G150<br>(Gardenia Yellow<br>dye) | | | 24,000 mg/kg | Mouse | Oral |
| Crocin L<br>(Gardenia Yellow<br>dye) | | | 24,000 mg/kg | Mouse | Oral |

TABLE 2

| | Exo vivo Large intestine | Small intestine | Stomach | Esophageal | Excitation wavelength | Concentration used |
|---|---|---|---|---|---|---|
| Safflower Y1500 (Safflower dye safflomin A + B) | G | | | | | |
| Cochineal (Cochineal red AL, carminic acid) | P | | | | | |
| HI RED S (Lac dye/laccaic acid) | P | | | | | |
| HI BLUE AT (Gardenia blue dye: geniposide) | G | | | | | |
| Curcumin (Turmeric extract) | VG 0.05% | VG 0.05% | VG Epithelium and glands well stained. | G | 780-800 nm | 0.50% |
| Curcumin (pure) | VG 0.01 mg/ml | VG 0.1 mg/ml | | | 780-800 nm | |
| Sulfuretin | VG Blood vessels powerfully stained with 1 mg/ml, 0.1 mg/ml | VG 0.1 mg/ml | G Epithelium: OK Glands: P | G | 780-800 nm | 1 mg/ml |
| Epigallocatechin gallate Green tea | G 0.01 mg/ml Not directly visible. | G Mucosal layer stained at 0.1 mg/ml, 0.01 mg/ml | | | 760 nm | 0.1 mg/ml |
| Indocyanine green | G 0.01 mg/ml Not directly visible. Apical cells powerfully stained. Glands not visible at high concentration. | G 0.01 mg/ml Apical cells powerfully stained. Epithelium invisible at high concentration. | | | 800 nm | 0.01 mg/ml |
| HI RED RA200 (Red radish dye: pelargonidin acyl glycoside) | G | | | | 800, 860 nm | 0.50% |
| HI RED V80 (Purple potato dye: cyanidin acyl glucoside and peonidin acyl glucoside) | | | | | 870 nm | 0.50% |
| Apigeninidin Kaoliang dye | VG | VG | G Parietal cells well stained. | | 740 nm | 1 mg/ml |
| Cyanidin | VG | | | | 760 nm | 1 mg/ml |
| Delphinidin Eggplant dye | VG | | VG Parietal cells well stained. | | 740 nm | 1 mg/ml |
| Fisetinidin Acacia mearnsii dye | | | VG Epithelium well stained. Parietal cells discernible. | | 800 | 1 mg/ml |

| | Stock concentration | Stock solvent | LD50 | | |
|---|---|---|---|---|---|
| Safflower Y1500 (Safflower dye safflomin A + B) | | | >20,000 mg/kg | Mouse | Oral |
| Cochineal (Cochineal red AL, carminic acid) | | | 8900 mg/kg | Mouse | Oral |
| HI RED S (Lac dye/laccaic acid) | | | 4000 mg/kg | Mouse | Oral |
| HI BLUE AT (Gardenia blue dye: geniposide) | | | 5000 mg/kg | Mouse | Oral |
| Curcumin (Turmeric extract) | | | 2000 mg/kg | Mouse | Oral |
| Curcumin (pure) | 100 mg/ml | 45% EtOH/ glycerol | 2000 mg/kg | Mouse | Oral |
| Sulfuretin | 100 mg/ml | DMSO | 300 mg/k | Mouse | Oral |
| Epigallocatechin gallate Green tea | 100 mg/ml | DMSO | 2170 mg/kg | Mouse | Oral |
| Indocyanine green | | PBS | 60 mg/kg | Mouse | Intravenous |

TABLE 2-continued

|  | Stock concentration | Stock solvent | LD50 | | |
|---|---|---|---|---|---|
| HI RED RA200 (Red radish dye: pelargonidin acyl glycoside) | | | | | |
| HI RED V80 (Purple potato dye: cyanidin acyl glucoside and peonidin acyl glucoside) | | | | | |
| Apigeninidin Kaoliang dye | 100 mg/ml | DMSO | 300 mg/kg | Mouse | Oral |
| Cyanidin | 100 mg/ml | DMSO | 1500 mg/kg | Rat | Intra-abdominal |
| Delphinidin Eggplant dye | 100 mg/ml | DMSO | 1250 mg/kg | Rat | Intra-abdominal |
| Fisetinidin *Acacia mearnsii* dye | 100 mg/ml | DMSO | ND | | |

TABLE 3

|  | Exo vivo Large intestine | Small intestine | Stomach | Esophageal | Excitation wavelength | Concentration used |
|---|---|---|---|---|---|---|
| Malvidin Blue sweet pea dye | VG | VG | Parietal cells well stained. | | 760 | 1 mg/ml |
| Pelargonidin | VG | | G | | 770 | 1 mg/ml |
| Robinetinidin *Robinia pseudoacacia* tree dye | G Epithelium: OK Glands: P | G | G | | 780 | 1 mg/ml |
| β-Carotene | VG | VG | Parietal cells wells stained. | | 740 | |
| HI RED BL (Red beet dye: betanin, isobetanin) | G | G | G Cell borders: P | G | 740 nm | 0.50% |
| Annatto WA-20 (Annatto dye achiote seed: norbixin) | G Tissue dissolved. | | | | 800 nm | 0.50% |
| Gingerol Ginger spice component | G | | | | 740 nm | 1 mg/ml |
| Myricetin Grape, onion dye | G | G | G Parietal cells discernible. | G | 740 | 1 mg/ml |
| Quercetin Onion, citrus dye | G Basal membrane well stained. | G | G Glands unstained. | G | 800 | 1 mg/ml |
| Tricetinidin Black tea dye | G | G | | | 740 | 1 mg/ml |
| Petunidine Red berry dye | G | G | | | 740 | 1 mg/ml |
| Capsanthin Capsicum dye | P | | | | 740 | 1 mg/ml |

|  | Stock concentration | Stock solvent | LD50 | | |
|---|---|---|---|---|---|
| Malvidin Blue sweet pea dye | 100 mg/ml | DMSO | 18 mg/kg | Mouse | Intravenous |
| Pelargonidin | 100 mg/ml | DMSO | 300 mg/kg | Mouse | Oral |
| Robinetinidin *Robinia pseudoacacia* tree dye | 100 mg/ml | DMSO | ND | | |
| β-Carotene | | | 5000 mg/kg | Rat | Oral |
| HI RED BL (Red beet dye: betanin, isobetanin) | | | >5000 mg/kg | Rat | Oral |
| Annatto WA-20 (Annatto dye achiote seed: norbixin) | | | 700 mg/kg | Mouse | Intra-abdominal |
| Gingerol Ginger spice component | 100 mg/ml | DMSO | 250 mg/kg | Mouse | Oral |
| Myricetin Grape, onion dye | 100 mg/ml | DMSO | 300 mg/kg | Mouse | Oral |
| Quercetin Onion, citrus dye | 100 mg/ml | DMSO | 160 mg/kg | Mouse | Oral |
| Tricetinidin Black tea dye | 100 mg/ml | DMSO | 300 mg/kg | Mouse | Oral |

TABLE 3-continued

| | | | | | |
|---|---|---|---|---|---|
| Petunidine Red berry dye | 100 mg/ml | DMSO | 4110 mg/ml | Mouse | Intra-abdominal |
| Capsanthin Capsicum dye | 100 mg/ml | DMSO Un-dissolved | 300 mg/kg | Mouse | Oral |

VG: Image having ideal brightness and contrast for image diagnosis; G: Image having sufficient brightness and contrast for image diagnosis, P: Image having insufficient brightness and contrast for image diagnosis; F: State between G and P.

Surprisingly, many types of dyes such as curcumin, sulfuretin and Red #3 (erythrosine) stained cancer lesion sites much more intensely than normal mucosa, regardless of pronase treatment of the mucosal surface. While it is not our intent to be constrained by theory, it is possible that the reason for intense staining of the cancer lesion sites is that in cancer lesion sites the intercellular adhesion is weak and many gaps are present between the cells, compared to normal mucosa where cellular adhesion is strong and there are virtually no intercellular gaps, and therefore the dye easily remained in the gaps. A second conceivable possibility is that cancer cells, which undergo rapid cell division, have higher uptake activity for extracellular lipophilic substances (most dyes having the nature of dissolving well in oils), compared to normal cells.

2. Dyes that are Strongly Excited and Provide Bright Living Cell Images

Of the aforementioned dye compounds, certain compounds were strongly excited by a multiphoton laser when coated onto the mucosal surface of mouse large intestine, and provided bright images. Dye compounds with which particularly bright images were obtained are shown in the fluorescent image lists of FIG. 6. The procedure from administration of the dye compound to observation was conducted as described above under "Evaluation of stainability" (same hereunder). Also, the administered concentration of dye to the mucosal surface was 5 mg/ml for curcumin as Dye No. 1, and 1 mg/ml for all of the other dyes.

3. Dyes that Preferentially Stain Epithelial Cells/Adenocytes

Figure 7A:
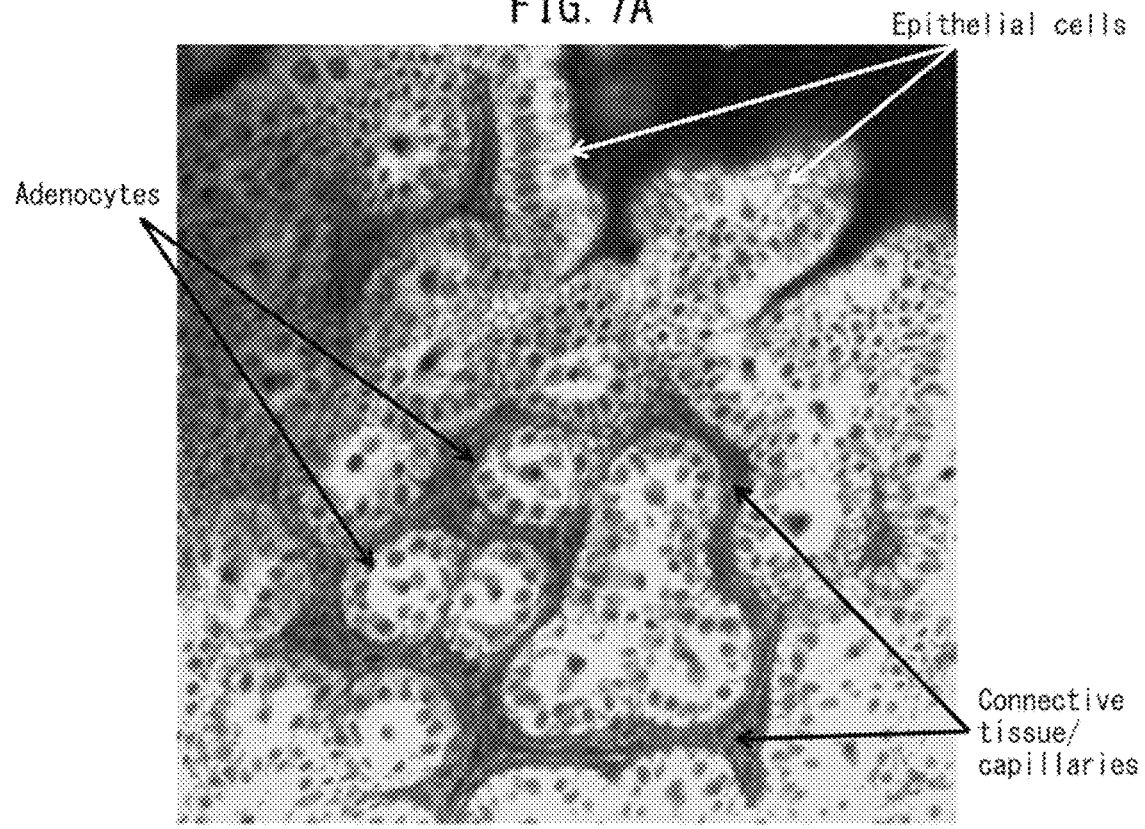
FIG. 7A is a photomicrograph showing curcumin preferentially staining epithelial cells/adenocytes.
Figure 7B:
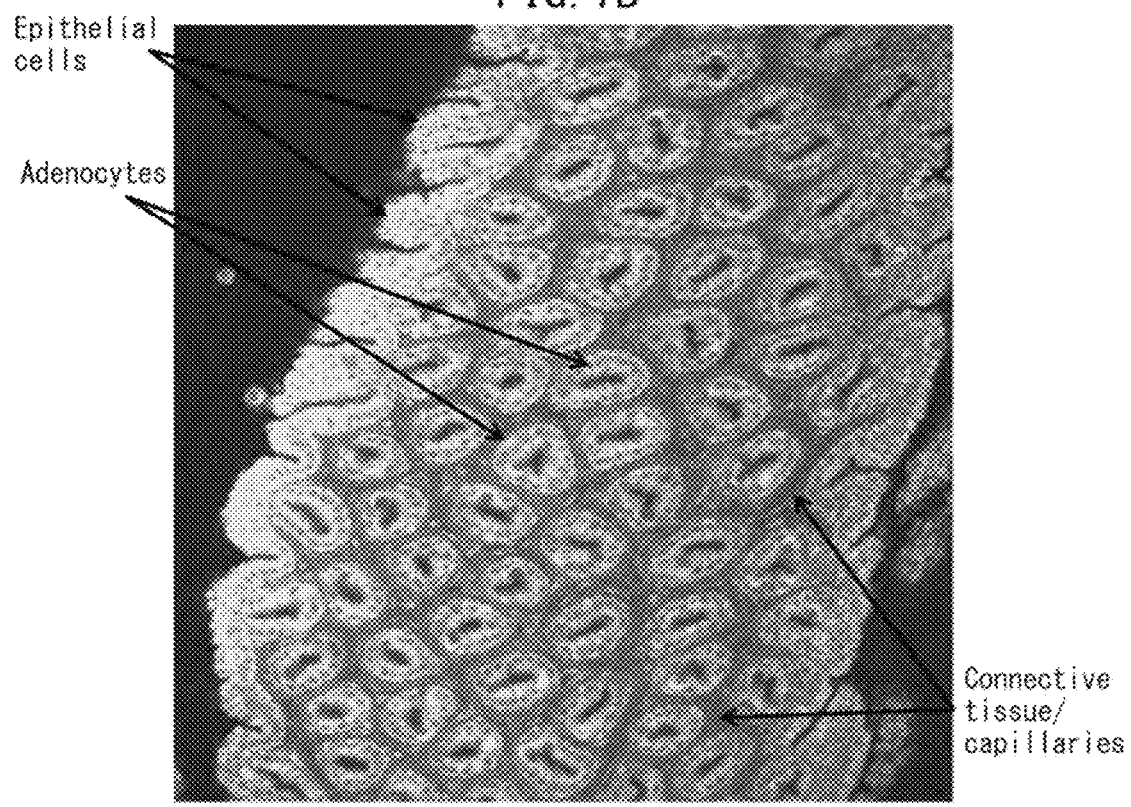
FIG. 7B is a photomicrograph showing sulfuretin preferentially staining epithelial cells/adenocytes.

Various dyes that preferentially stain epithelial cells/adenocytes were confirmed, and FIG. 7 shows staining patterns for curcumin as Dye No. 1 and sulfuretin as Dye No. 2, as representative examples. These dyes intensely stained epithelial cells/adenocytes and faintly stained connective tissue/capillaries. In addition, epigallocatechin gallate as Dye No. 3, Red #3 (erythrosine) as Dye No. 4, Red #104 (phloxine) as Dye No. 9, indocyanine green as Dye No. 15, malvidin as Dye No. 27, β-carotene as Dye No. 28, HI RED BL as Dye No. 32, 6-gingerol as Dye No. 33, myricetin as Dye No. 35, tricetinidin as Dye No. 36 and petunidine as Dye No. 37 also preferentially stained epithelial cells/adenocytes (results not shown).

4. Dyes that Preferentially Stain Connective Tissue/Capillaries

Figure 8A:
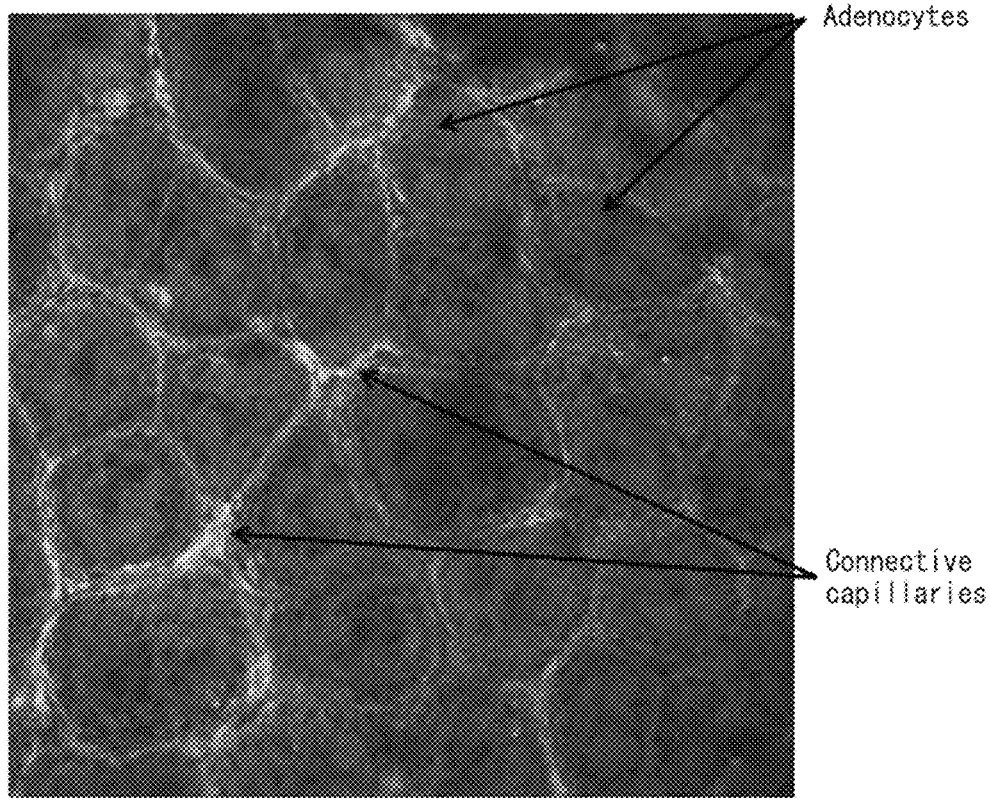
FIG. 8A is a photomicrograph showing annatto preferentially staining connective tissue/capillaries.
Figure 8B:
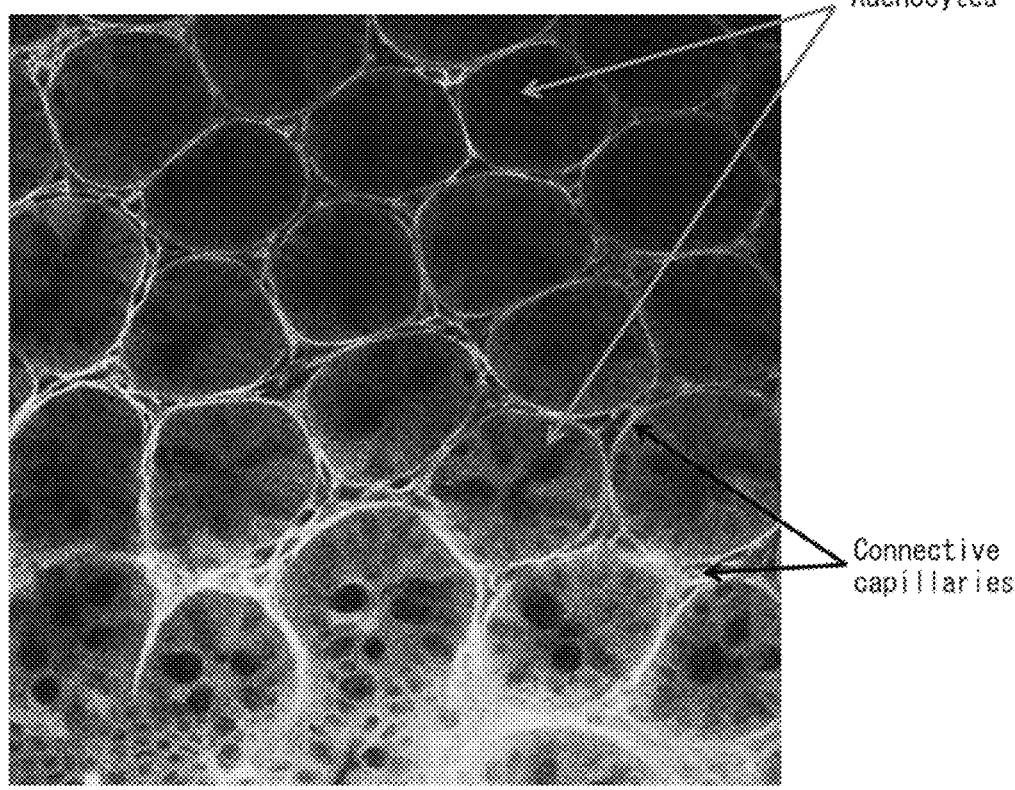
FIG. 8B is a photomicrograph showing annatto and quercetin preferentially staining connective tissue/capillaries.

Various dyes that preferentially stain connective tissue/capillaries were confirmed, and FIG. 8 shows staining patterns for annatto as Dye No. 14 and quercetin as Dye No. 34, as representative examples. These dyes intensely stained connective tissue/capillaries and faintly stained epithelial cells/adenocytes. In addition, Blue #2 as Dye No. 10, Gardenia Yellow dye as Dye No. 16, crocin G-150 as Dye No. 17, safflomin as Dye No. 18, robinetinidin as Dye No. 24, HI RED V80 as Dye No. 31 and quercetin as Dye No. 34 also preferentially stained connective tissue/capillaries.

Figure 9A:
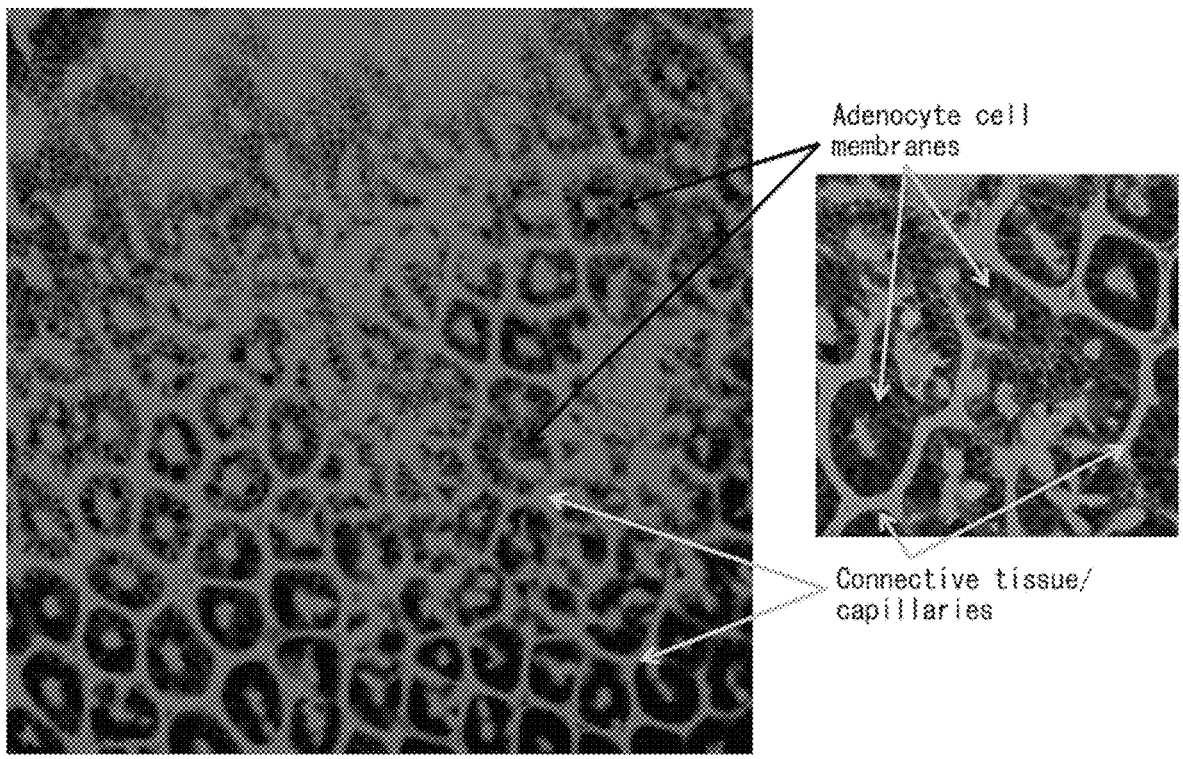
FIG. 9A is a pair of photomicrographs showing Red #106 preferentially staining both epithelial cells/adenocytes and connective tissue/capillaries.
Figure 9B:
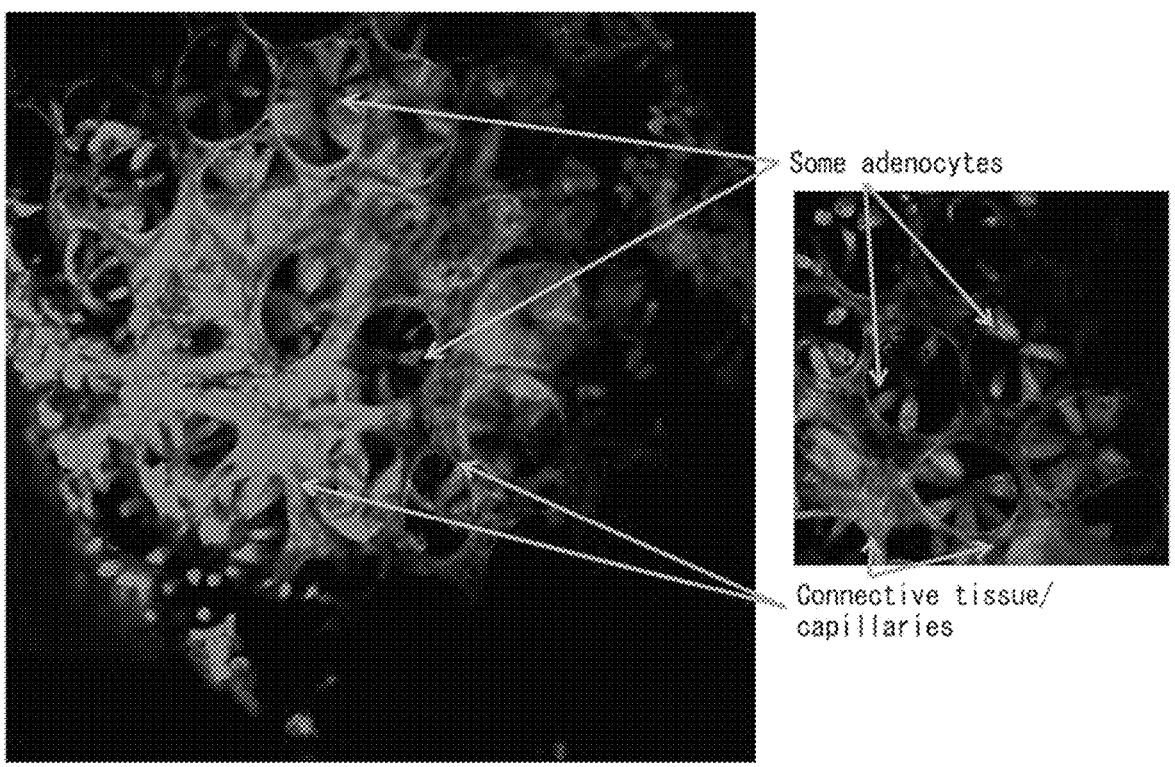
FIG. 9B is a pair of photomicrographs showing Green #3 preferentially staining both epithelial cells/adenocytes and connective tissue/capillaries.

5. Dyes that Stain Both Epithelial Cells/Adenocytes and Connective Tissue/Capillaries Dyes that stain both epithelial cells/adenocytes and connective tissue/capillaries were also confirmed, and FIG. 9 shows staining patterns for Red #106 as Dye No. 5 as Green #3 as Dye No. 6, as representative examples. With Red #106 (Dye No. 5) the cell membranes of epithelial cells and adenocytes, and connective tissue/capillaries were strongly stained. With Green #3 (Dye No. 6) some adenocytes and connective tissue/capillaries were strongly stained.

Example 2

In vitro assay of MDCK-Ras$^{V12}$ cancerized cell small aggregates as a very early cancer model
(Materials)
  MDCK normal cells; canine renal tubular epithelial cell-derived cell line.
  MDCK-GFP-Ras$^{V12}$ cells that express GFP-Ras$^{V12}$ which is the green fluorescent protein GFP fused to the constitutively activated oncogene product Ras$^{V12}$ (Ras$^{V12}$ being Ras with the 12th amino acid residue glycine replaced by valine, as a mutation found in 30% to 40% of colon cancers).
  DMEM (high glucose) with Phenol Red (Wako Pure Chemical Industries, Ltd.)
  DMEM (high glucose) without Phenol Red (Wako Pure Chemical Industries, Ltd.)
  Tetracycline System Approved Fetal bovine serum (Clontech)
  Penicillin/Streptomycin (×100) (Nacalai Tesque, Inc.)
  GlutaMax (×100) (Invitrogen)
  Trypsin (0.25%) (no phenol red, Invitrogen)+EDTA (3 mM) (Nacalai Tesque, Inc.)
  Zeocin (100 mg/ml, InvivoGen)
  Blasticidin (10 mg/ml, InvivoGen)
  Tetracycline (SIGMA)/100% ethanol (100 mg/ml)
  10 cm dish (BD Falcon)
  6 cm dish (BD Falcon)
  96-well dish (Lumox® multi well 96, SARSTEDT)
  DMSO (Nacalai Tesque, Inc.)
  USFDA (Food and Drug Administration)-approved compounds, Prestwick Chemical Library (1200 types)
  Japanese Ministry of Health, Labour and Welfare-approved food additives (30 types)
  Multiphoton laser microscope (FV1000 MPE, Olympus)
(Method)
  The MDCK normal cells were cultured in a 10 cm dish, and the MDCK-GFP-Ras$^{V12}$ cells were cultured in a 6 cm dish. The culture solution used for the MDCK normal cells was DMEM (containing Phenol Red)+10% FBS+penicillin/streptomycin.
  The solution used for the MDCK-GFP-Ras$^{V12}$ cells was DMEM (containing Phenol Red)+10% FBS+penicillin/streptomycin+Zeocin (400 μg/ml)+blasticidin (5 μg/ml). When both reached approximately 90% confluency, the respective cells were stripped from the dish using Trypsin (0.25%)+EDTA (3 mM), and seeded in a 96-well dish to MDCK normal cell:MDCK-GFP-Ras$^{V12}$ cell ratio of 50 to 100:1. The seeding was carried out using a DMEM+10% FBS+penicillin/streptomycin culture solution, to 1.0 to 3.0× $10^4$ cells per well of the 96-well dish. Tetracycline at a concentration of 2 μg/ml was added to the culture solution after 4 days when seeding was to 1.0×$10^4$ or after 1 day when seeding was to 3.0×$10^4$, and GFP-Ras$^{V12}$ was expressed, forming cancerized cell small aggregates among the MDCK normal cells (NPL 3). After 18 to 36 hours, the cells in each of the wells were rinsed 3 times with 200 μl of PBS, and then the Prestwick Chemical Library compounds and the Ministry of Health, Labour and Welfare-approved food additives, each diluted to 1 μM with a 100 μl volume of PBS, were added to the respective wells and taken up by the cells for 5 minutes at room temperature. They were then rinsed 3 times with 200 μl of PBS, and in certain cases further rinsed once with 100 μl of DMEM without Phenol Red, and observed under a multiphoton laser microscope. Compounds that intensely label GFP-Ras$^{V12}$-positive cancerized cell small aggregates compared to normal cells upon excitation with pulse laser photons in a stepwise manner in the range of 750, 800, 850, 900 nm, or compounds that intensely label MDCK normal cells compared to cancerized cell small aggregates, in the red visible light region, were searched for and identified from among 1200 different types of compounds included in the Chemical Library and from among Ministry of Health, Labour and Welfare-approved food additives.

(Results)

Figure 10:
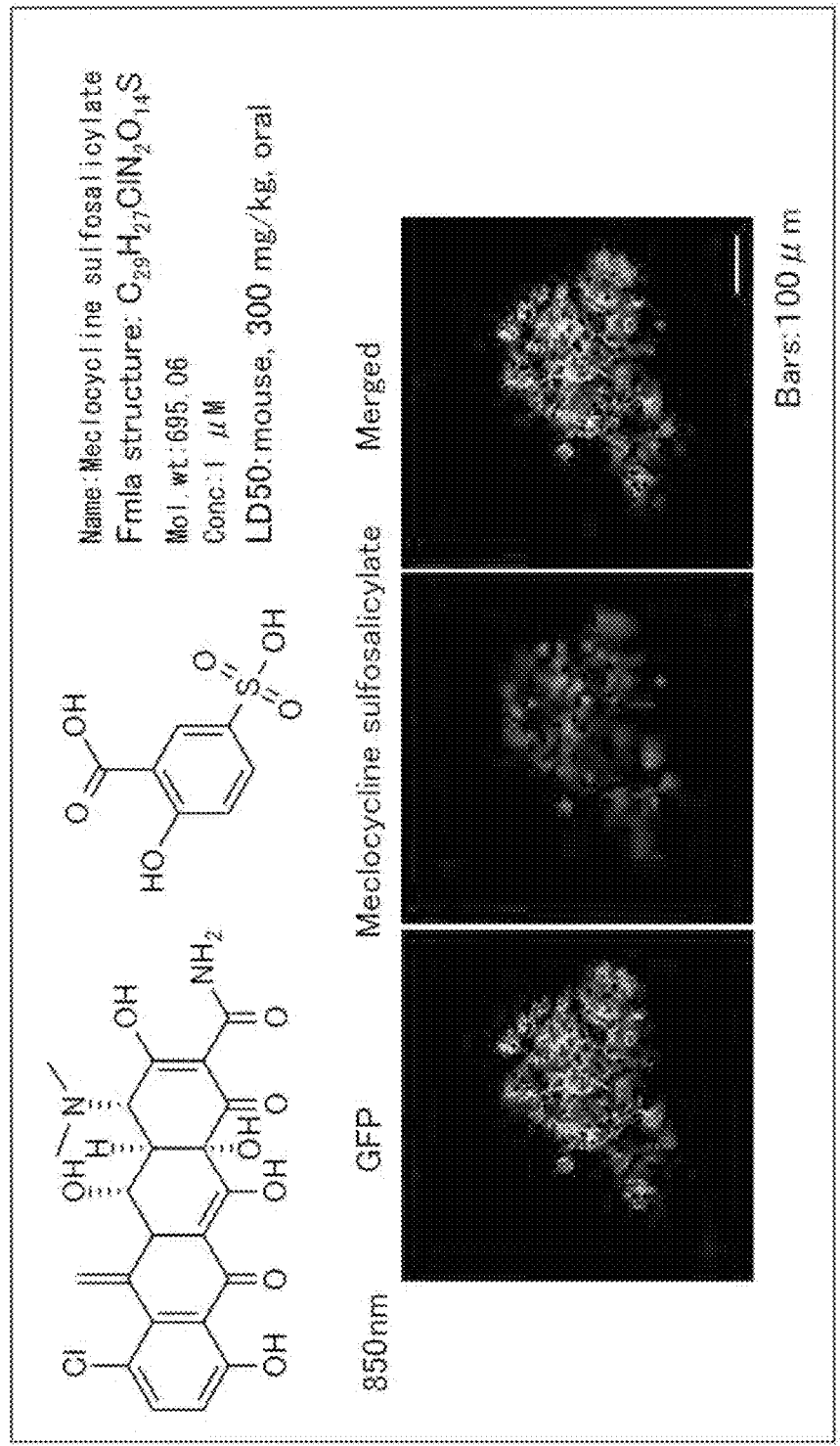
FIG. 10 shows specific staining of cancer cells by meclocycline sulfosalicylate. GFP-Ras$^{V12}$ positive cells were preferentially stained. The GFP-Ras$^{V12}$ positive cells were stained from a minimum of one to a cell population of several.
Figure 11:
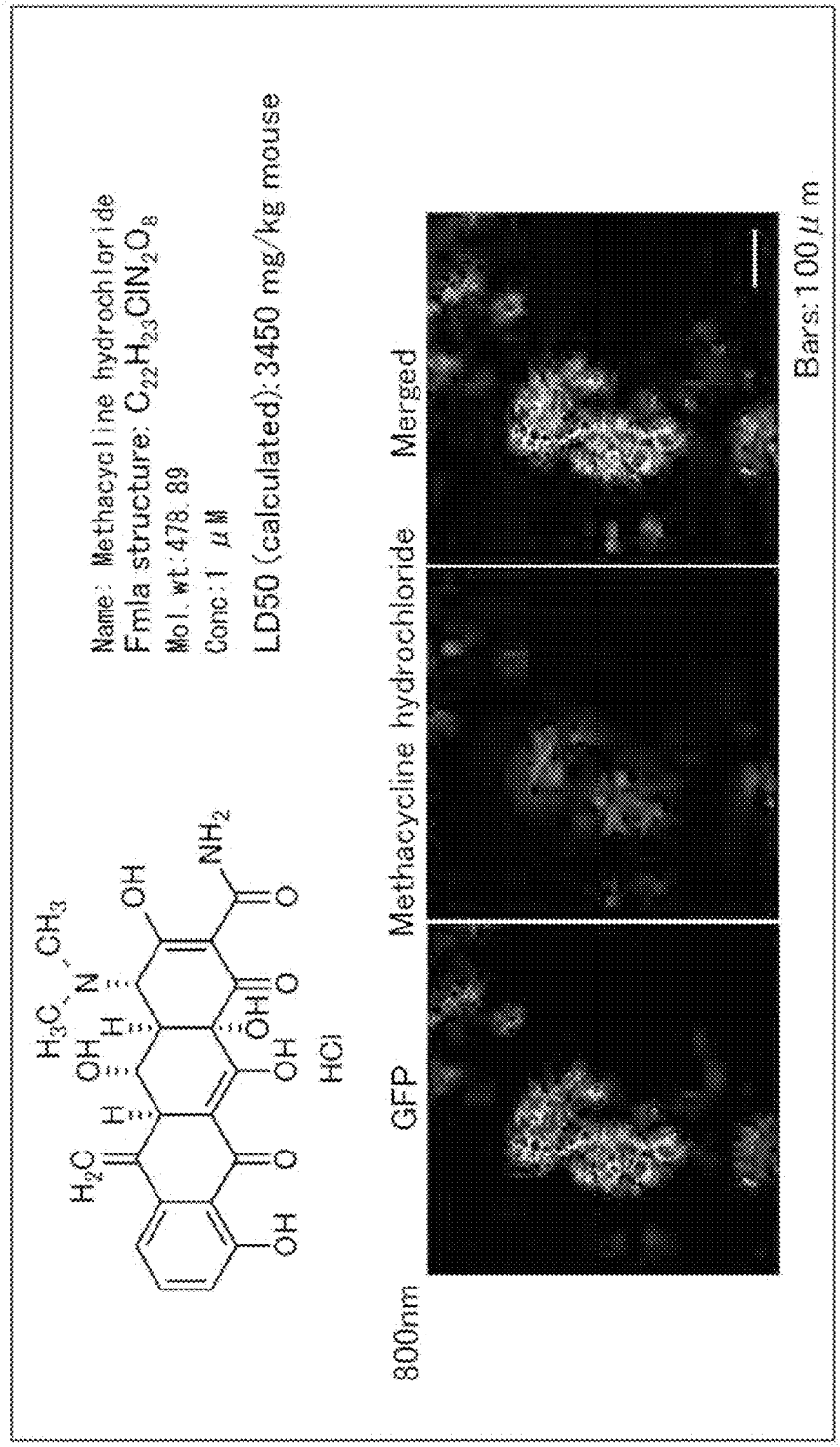
FIG. 11 shows specific staining of cancer cells by methacycline hydrochloride. GFP-Ras$^{V12}$ positive cells were preferentially stained. The GFP-Ras$^{V12}$ positive cells were stained from a minimum of one to a cell population of several.
Figure 12:
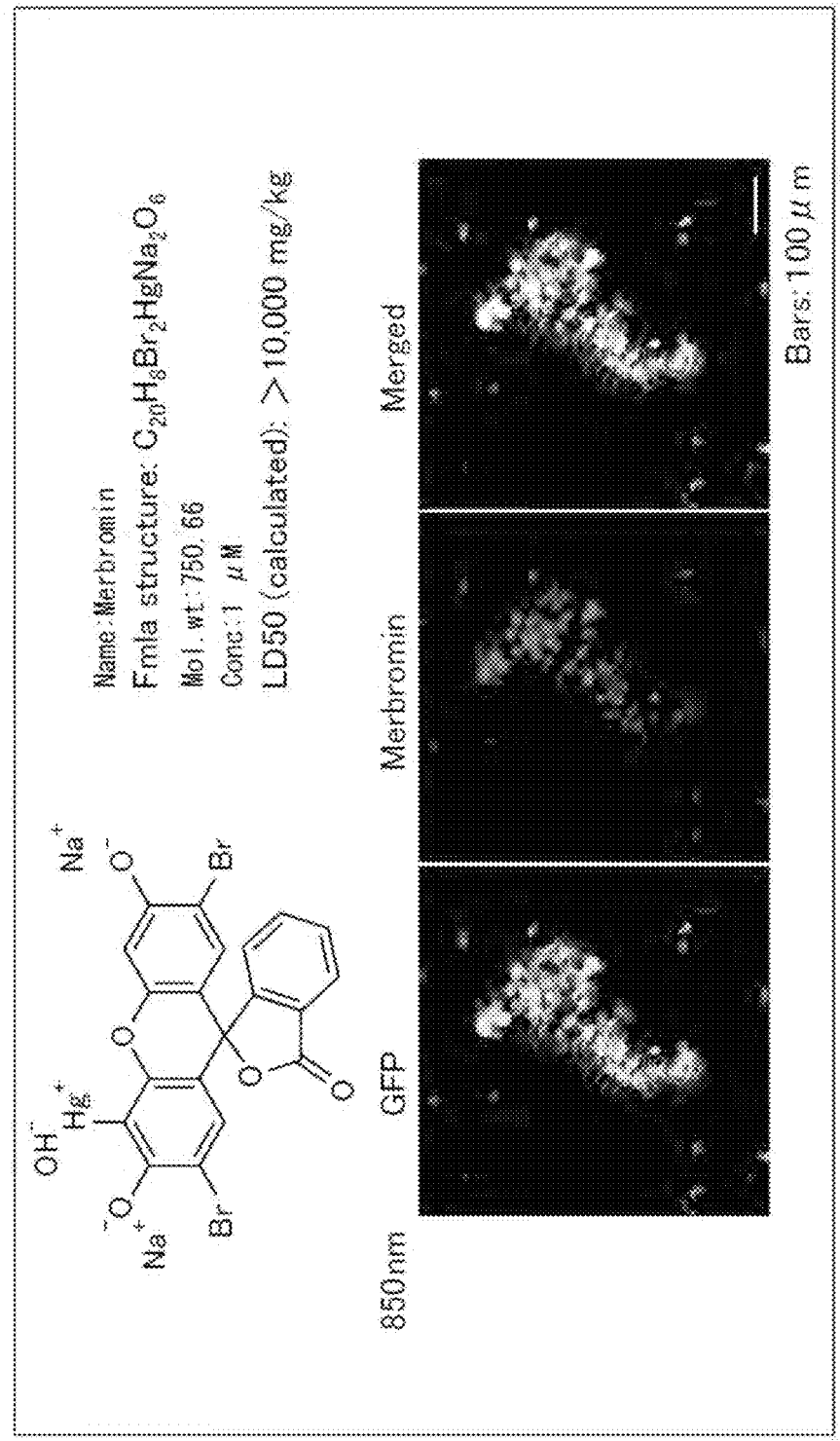
FIG. 12 shows specific staining of cancer cells by merbromin. GFP-Ras$^{V12}$ positive cells were preferentially stained. The GFP-Ras$^{V12}$ positive cells were stained from a minimum of one to a cell population of several.
Figure 13:
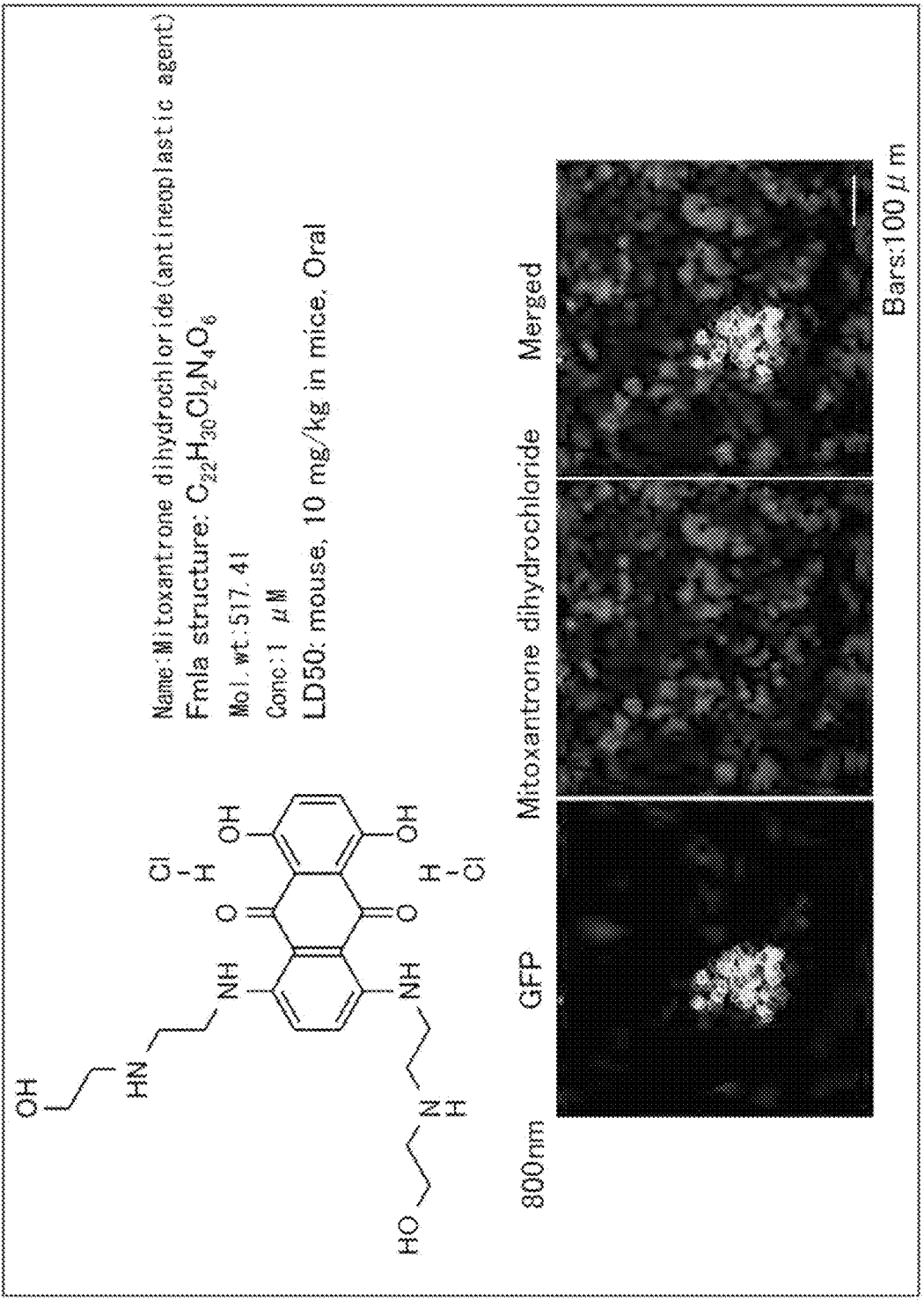
FIG. 13 shows specific staining of normal cells by mitoxantrone dihydrochloride, compared to cancer cells. GFP-Ras$^{V12}$ cells were not specifically stained, but normal cells were stained.
Figure 14:
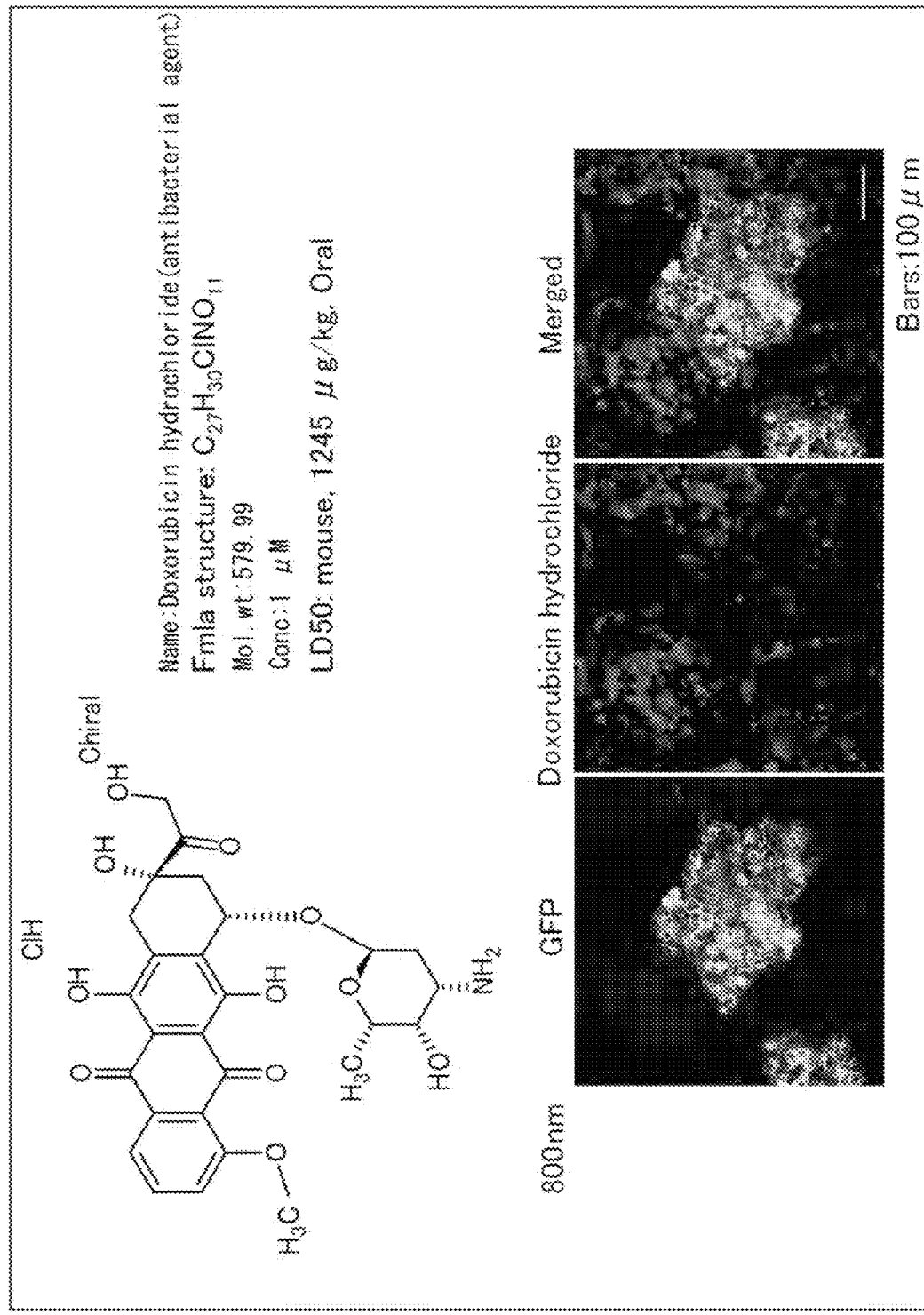
FIG. 14 shows specific staining of normal cells by doxorubicin hydrochloride, compared to cancer cells. GFP-Ras$^{V12}$ cells were not specifically stained, but normal cells were stained.
Figure 15:
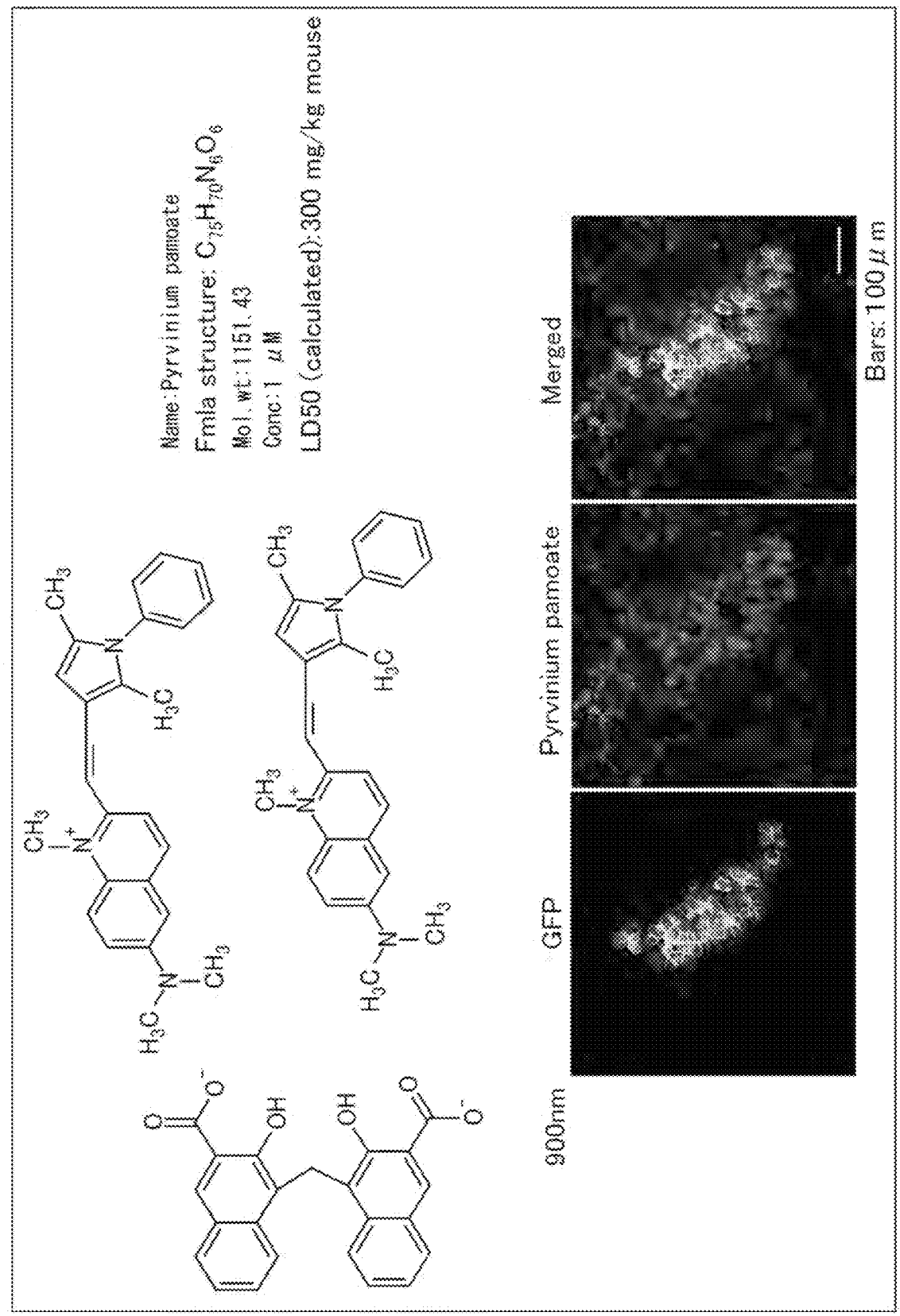
FIG. 15 shows staining of both normal cells and cancer cells by pyrvinium pamoate.
Figure 16:
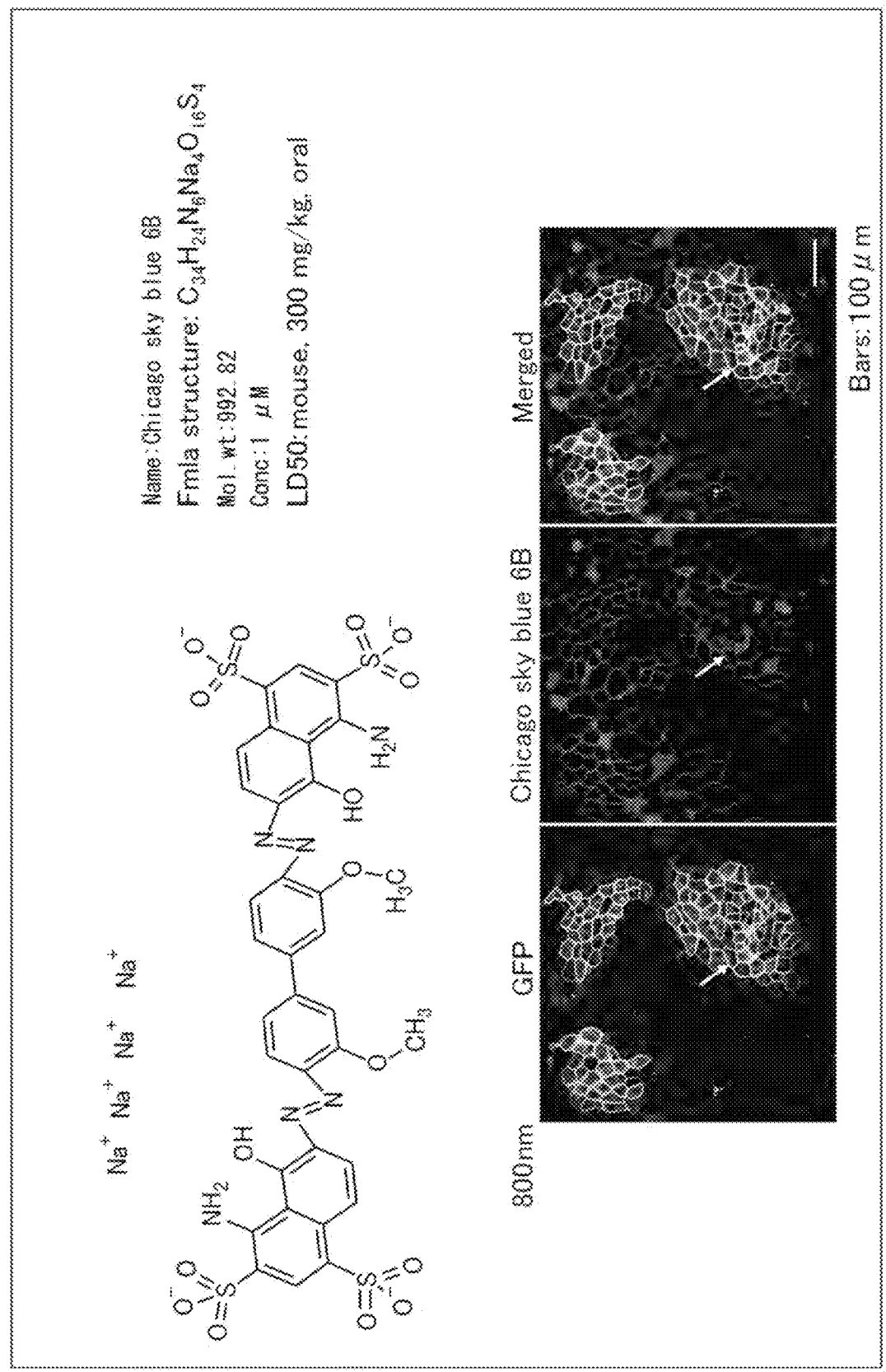
FIG. 16 shows equal staining of normal cells and cancer cells by Chicago Sky Blue 6B. White arrows: cell adhesion sites of GFP-Ras$^{V12}$ positive cells stained with Chicago Sky Blue 6B. Some of the GFP-Ras$^{V12}$ positive cells were stained in the cytoplasm.
Figure 17:
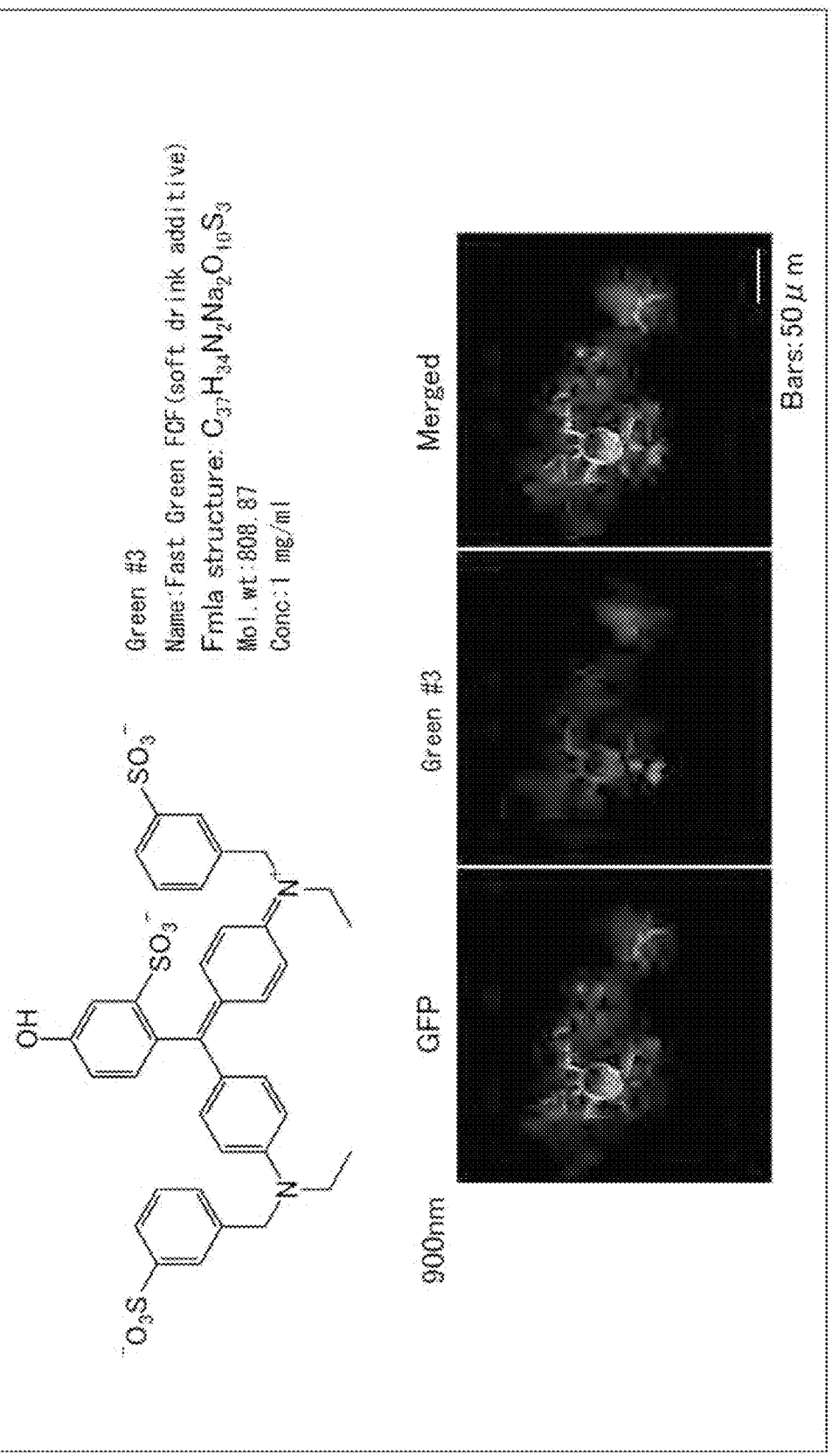
FIG. 17 shows specific staining of cancer cells by Fast Green FCF.
Figure 18:
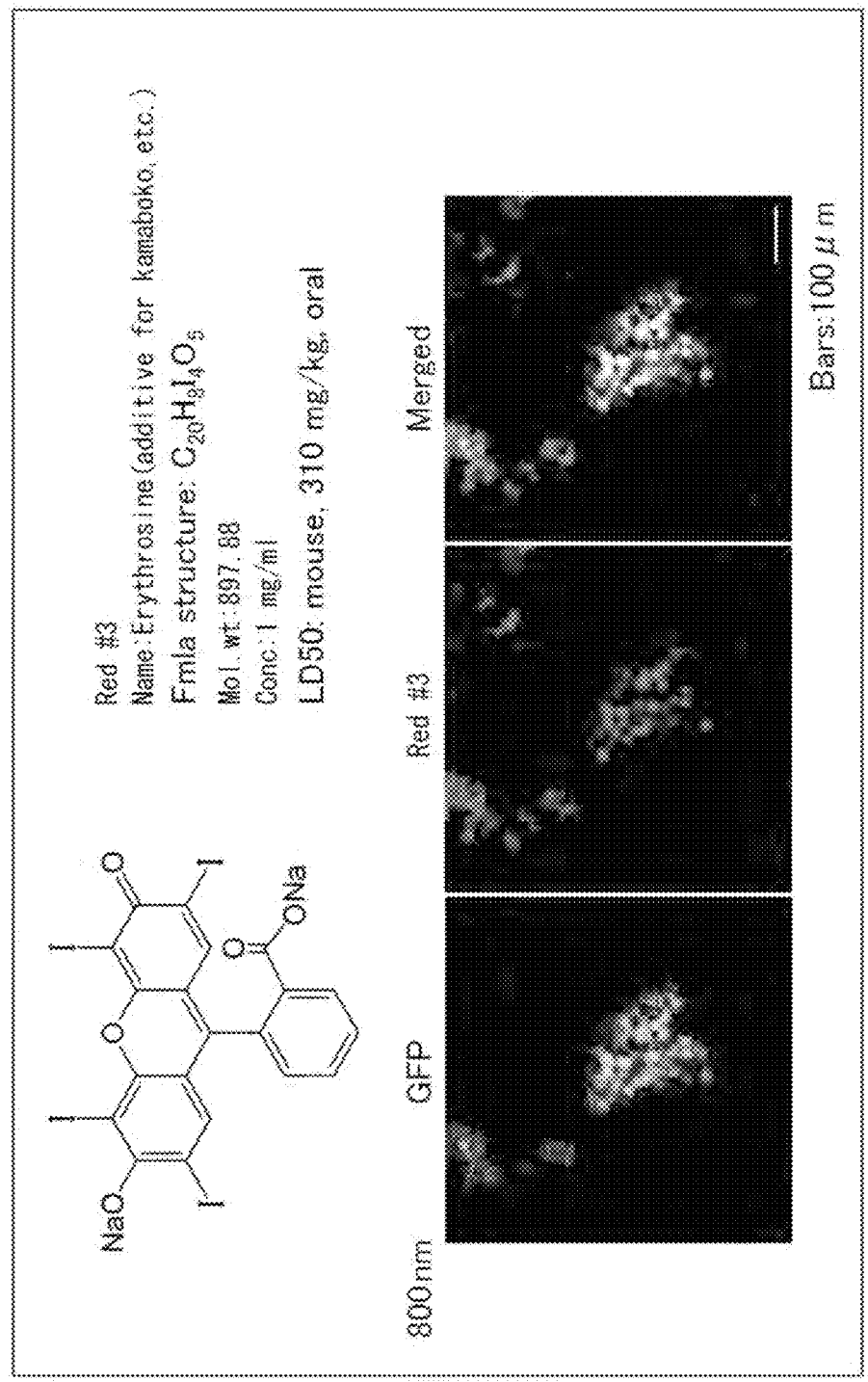
FIG. 18 shows specific staining of cancer cells by Red #3 (erythrosine). GFP-Ras$^{V12}$ positive cells were preferentially stained. The GFP-Ras$^{V12}$ positive cells were stained from a minimum of one to a cell population of several. A small number of normal cells were also stained with Red #104 dye.
Figure 19:
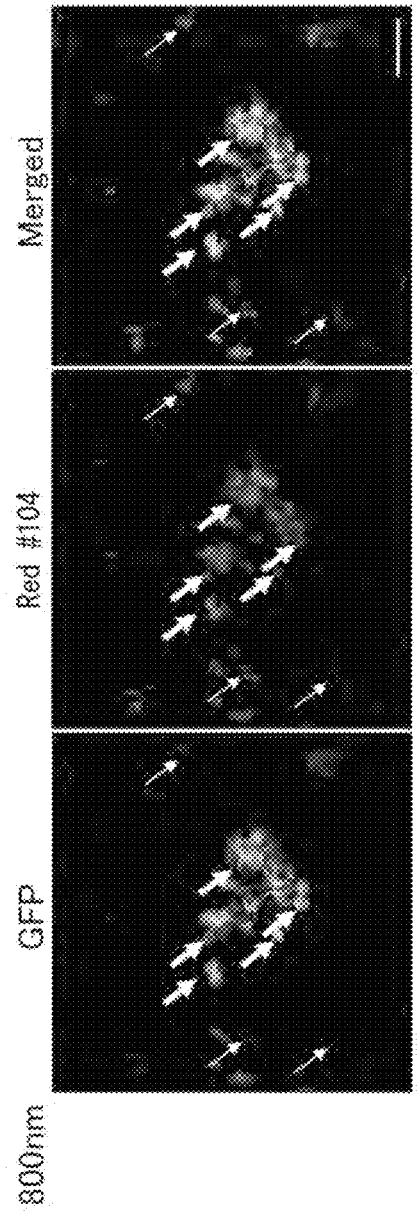
FIG. 19 shows specific staining of cancer cells by Red #104 (phloxine). Thick white arrows: All GFP-Ras$^{V12}$ positive cells stained with Red #104. The GFP-Ras$^{V12}$ positive cells were stained with Red #104, from a minimum of one to a cell population of several. The cancer cell staining intensity was 6.7 times the normal cell staining intensity. Thin white arrows: Small number of normal cells also stained with Red #104 dye.
Figure 20:
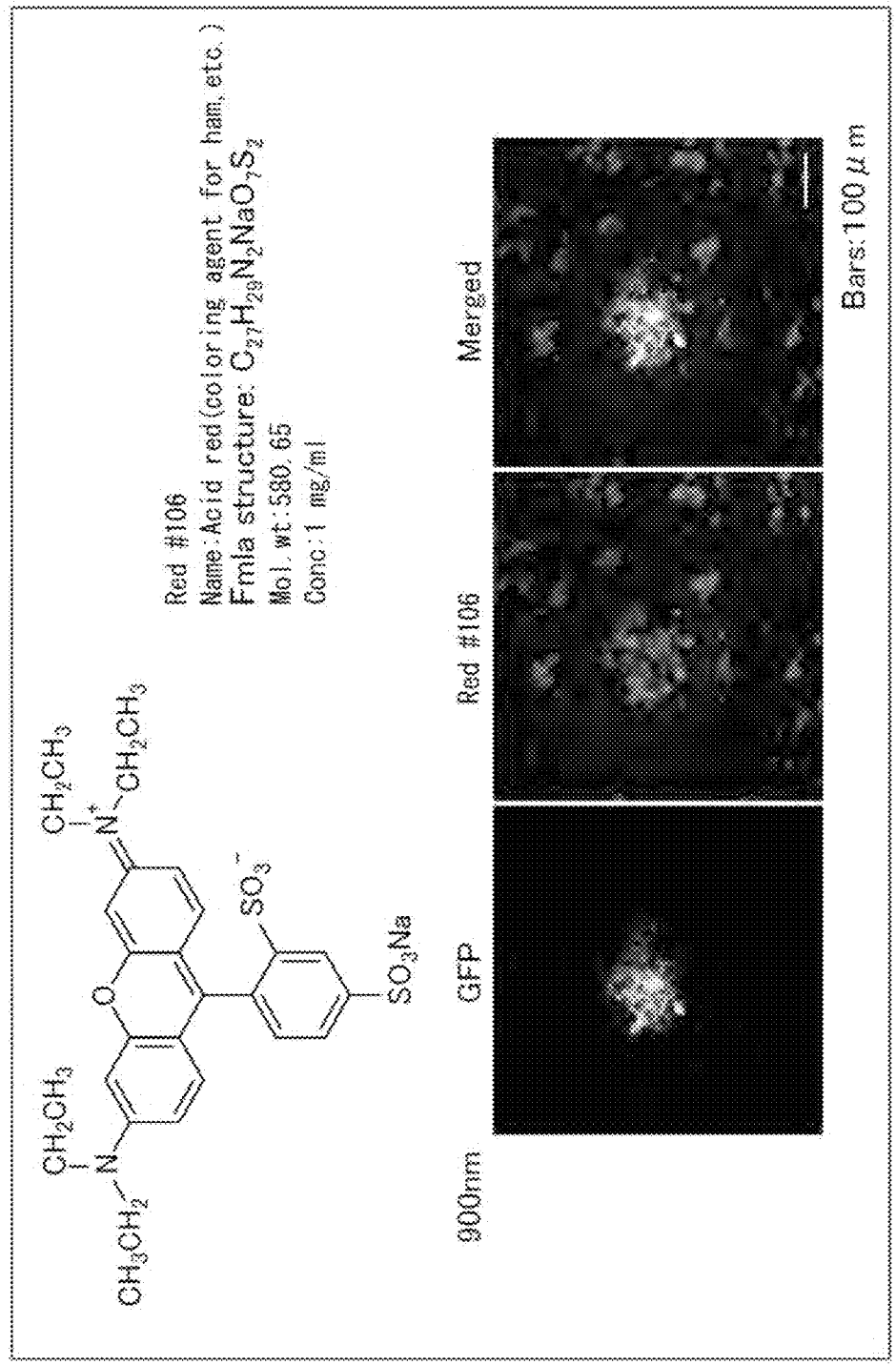
FIG. 20 shows staining of both normal cells and cancer cells by Acid Red.
Figure 21A:
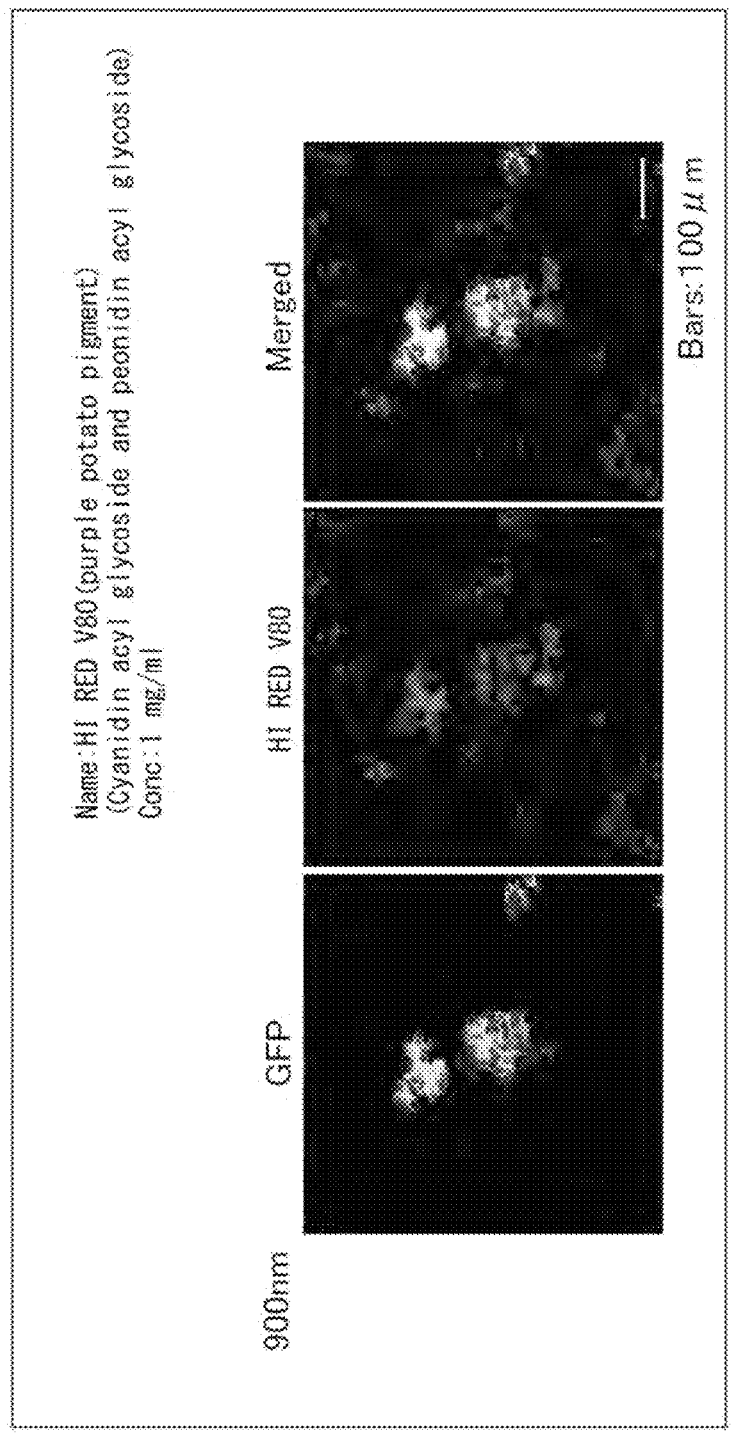
FIG. 21A shows staining of both normal cells and cancer cells by HI RED V80 (purple potato dye).
Figure 21C:
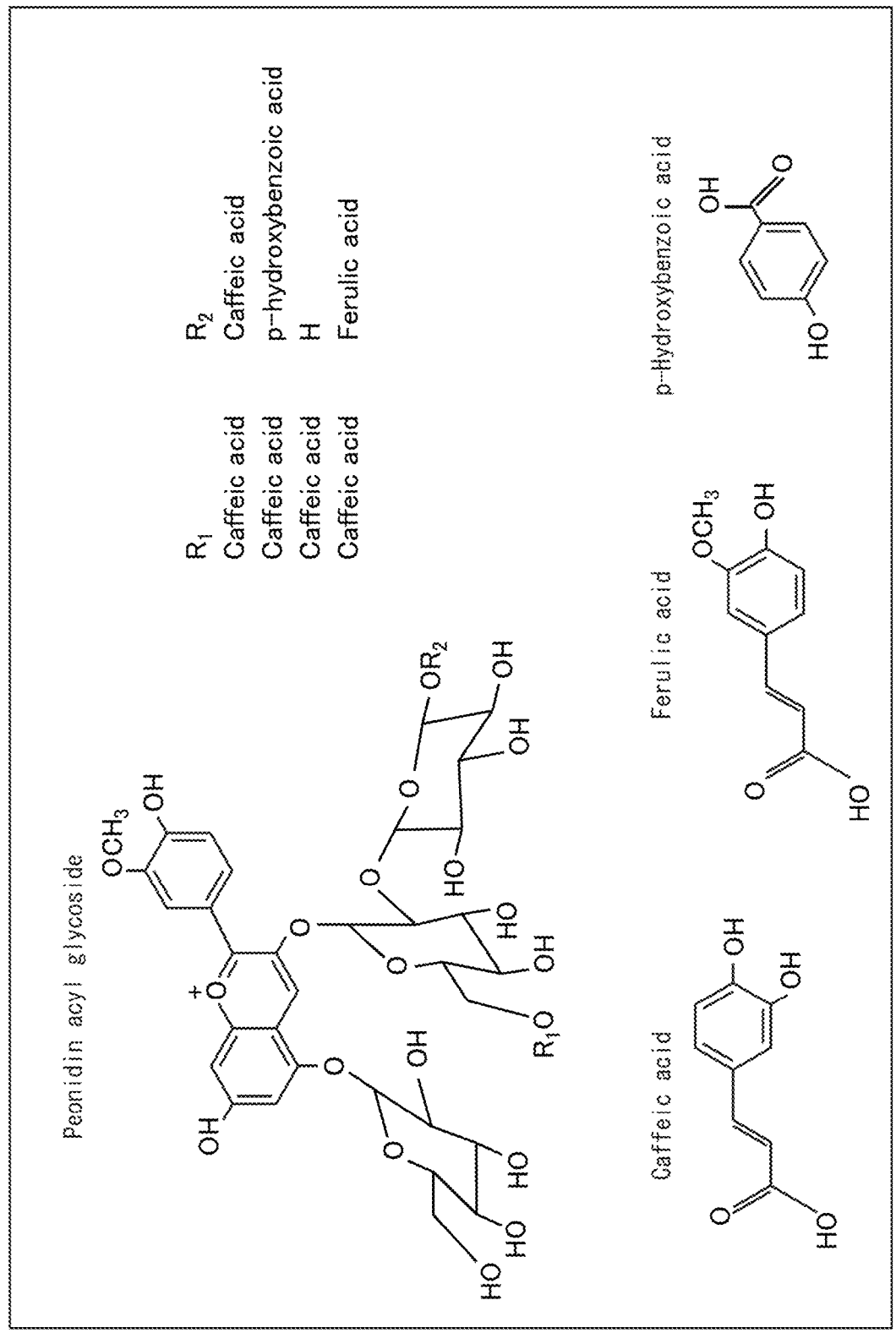
FIG. 21C shows the constituent component peonidin acyl glucoside of HI RED V80.

Among the 1200 different types of the Prestwick Chemical Library, 3 compounds, meclocycline sulfosalicylate, methacycline hydrochloride and merbromin, were identified as compounds that wereintensely labeled in GFP-Ras$^{V12}$ positive cancerized cell small aggregates compared to normal cells, i.e. that exhibit strong fluorescence, of red visible light by photon excitation in all of the regions of 750, 800, 850 and 900 nm (FIGS. 10, 11 and 12). The fluorescence states shown in FIG. 10 to FIG. 12 will now be explained. FIG. 10 shows the evaluation results for meclocycline sulfosalicylate, with the structural formula shown at the top. In this figure, evaluation was performed using 850 nm laser light, and the photograph labeled "GFP" at the left is a case where green fluorescence was clearly observed in MDCK-GFP-Ras$^{V12}$ cells. The center image labeled "Meclocycline sulfosalicylate" in FIG. 10 is a case where staining was by meclocycline sulfosalicylate and red fluorescence was clearly observed. Since red fluorescence is emitted in a broad wavelength range depending on the multiphoton laser, it was extracted with a red filter, centering on red fluorescence. The image labeled "Merged" at the right of FIG. 10 is a merged composite of "GFP" and "Meclocycline sulfosalicylate". Although it may be difficult to appreciate the precision in the black and white images in this patent specification, it will be appreciated that the MDCK-GFP-Ras$^{V12}$ cells shown in "GFP" and the fluorescence by staining with meclocycline sulfosalicylate overlap to a very high degree of precision. This demonstrates that staining with meclocycline sulfosalicylate accurately indicates cancer cells by fluorescence. Similar evaluations are shown using methacycline hydrochloride in FIG. 11, and merbromin in FIG. 12, both of which show green fluorescence in the image at left labeled "GFP", and red fluorescence in the center image with staining, showing a reddish green color (luminescence close to yellow) by similar highly precise overlapping as in FIG. 10 in the image labeled "Merged" at the right, similar to FIG. 10. This demonstrates that staining with methacycline hydrochloride or with merbromin also accurately indicates cancer cells by fluorescence. Also, two different compounds mitoxantrone dihydrochloride and doxorubicin hydrochloride (FIGS. 13 and 14), as compounds intensely labeling MDCK normal cells compared to cancerized cell small aggregates by photon excitation in all of the regions of 750, 800, 850 and 900 nm, and the fluorescence states shown in FIG. 13 and FIG. 14 differ from FIG. 10 to FIG. 12 in that only normal cells exhibit fluorescence by staining, the center images in both figures showing red fluorescence in normal cells, thus indicating that the sites not exhibiting fluorescence are cancer cells. Two compounds, pyrvinium pamoate and Chicago sky blue 6B (FIGS. 15 and 16) were identified as compounds labeling both cancerized cell small aggregates and normal cells. The fluorescence states shown in FIG. 15 and FIG. 16 are green fluorescence emitted in cancer cells by "GFP" at left, and red fluorescence emitted in both normal cells and cancer cells by "Pyrvinium pamoate" and "Chicago sky blue", at the center. Among the Ministry of Health, Labour and Welfare-approved food additives, 3 compounds, Fast Green FCF, erythrosine and phloxine (FIGS. 17, 18 and 19) were identified as compounds that labeled GFP-Ras$^{V12}$-positive cancerized cell small aggregates more intensely than normal cells by red visible light upon photon excitation in all of the regions of 750, 800, 850 and 900 nm. In FIG. 17 to FIG. 19, in each center image, it is seen that strong fluorescence was emitted and observed in cancer cells. Also, 2 compounds, Acid Red and HI RED V80 (purple potato dye) (FIGS. 20 and 21) were identified as compounds that labeled both cancerized cell small aggregates and normal cells. Emission of red fluorescence can be seen in both normal cells and cancer cells, in each of the center images of FIG. 20 to FIG. 21.

In other words, there were identified 6 compounds: meclocycline sulfosalicylate, methacycline hydrochloride, merbromin, Fast Green FCF, erythrosine and phloxine, as compounds that intensely label GFP-Ras$^{V12}$-positive cancerized cell small aggregates compared to normal cells, 2 compounds: mitoxantrone dihydrochloride and doxorubicin hydrochloride, as compounds that intensely label MDCK normal cells compared to cancerized cell small aggregates, and 4 compounds: pyrvinium pamoate, Chicago sky blue 6B, Acid Red and HI RED V80 (purple potato dye), as compounds that label both cancerized cell small aggregates and normal cells.

The compounds identified among the Prestwick Chemical Library of 1200 types of FDA-approved compounds all stained the cells with stain concentrations of 1 μM. In addition, the food additives identified among the Ministry of Health, Labour and Welfare-approved food additives all stained the cells at concentrations of 1 mg/ml. As explained above, by using a mixture of a substance that specifically stains either cancer cells or normal cells and emits fluorescence and a substance that stains both, it becomes easy to increase detection accuracy and to ascertain the region near the border between both tissues. Removing the normal cells near the border may be effectively employed as a strategy for avoiding false negative assessments and preventing recurrence. The reporter gene "GFP" was used here as one that intensely labels cancer cells, but the same evaluation can be made using a reporter gene that intensely labels normal cells.

Example 3

1. Evaluation of Dye Compound Stainability

Drinking water containing 2% (w/v) dextran sodium sulfate (DSS) was given to 8-week-old C57B6 mice (male, approximately 20 g) for 7 days. After intraperitoneal injection of 0.2 ml of 5% chloral hydrate for anesthesia, the mouse abdominal wall was incised vertically to about 1 cm, and the gastrointestinal tract was raised over the abdominal wall to about 1 cm. Blood flow to the gastrointestinal tract was maintained during this time by the blood vessel flowing into the mesenteric attachment site. The gastrointestinal tract was incised vertically to about 1 cm on the opposite side of the mesenteric attachment site, including the tunica muscularis and mucosa. The opposite side of the mesenteric attachment site was incised in order to prevent severance and damage of the blood vessel and minimize bleeding. When the incision site of the gastrointestinal tract was opened vertically, the mucosal surface of the gastrointestinal tract, as the food channel, became visible. When food digestion products were present they were wiped off with tissue paper.

In order to more clearly observe the gastrointestinal tract mucosal surface, a 1% pronase solution was dropped onto the mucosal surface and was allowed to stand still for 15 minutes. This pronase treatment removed the mucus from the mucosal surface, rendering the cell structure more easily visible. Next, the pronase was removed from the mucosal surface and rinsed with physiological saline (PBS).

A metal ring (outer diameter: 16 millimeters, inner diameter, 6 millimeters) was placed on a laboratory stage, and a rapid bonding adhesive (AronAlpha) was coated over the entire periphery of the surface on one side. Forceps were used to hold the rapid bonding adhesive-coated metal ring with the adhesive-coated surface facing downward, and it was set on the pronase-treated mucosal surface. During a period of about 5 minutes, the metal ring became anchored to the mucosa with the rapid bonding adhesive, and the region where the dye compound was to be applied was rinsed with PBS.

Figure 32:
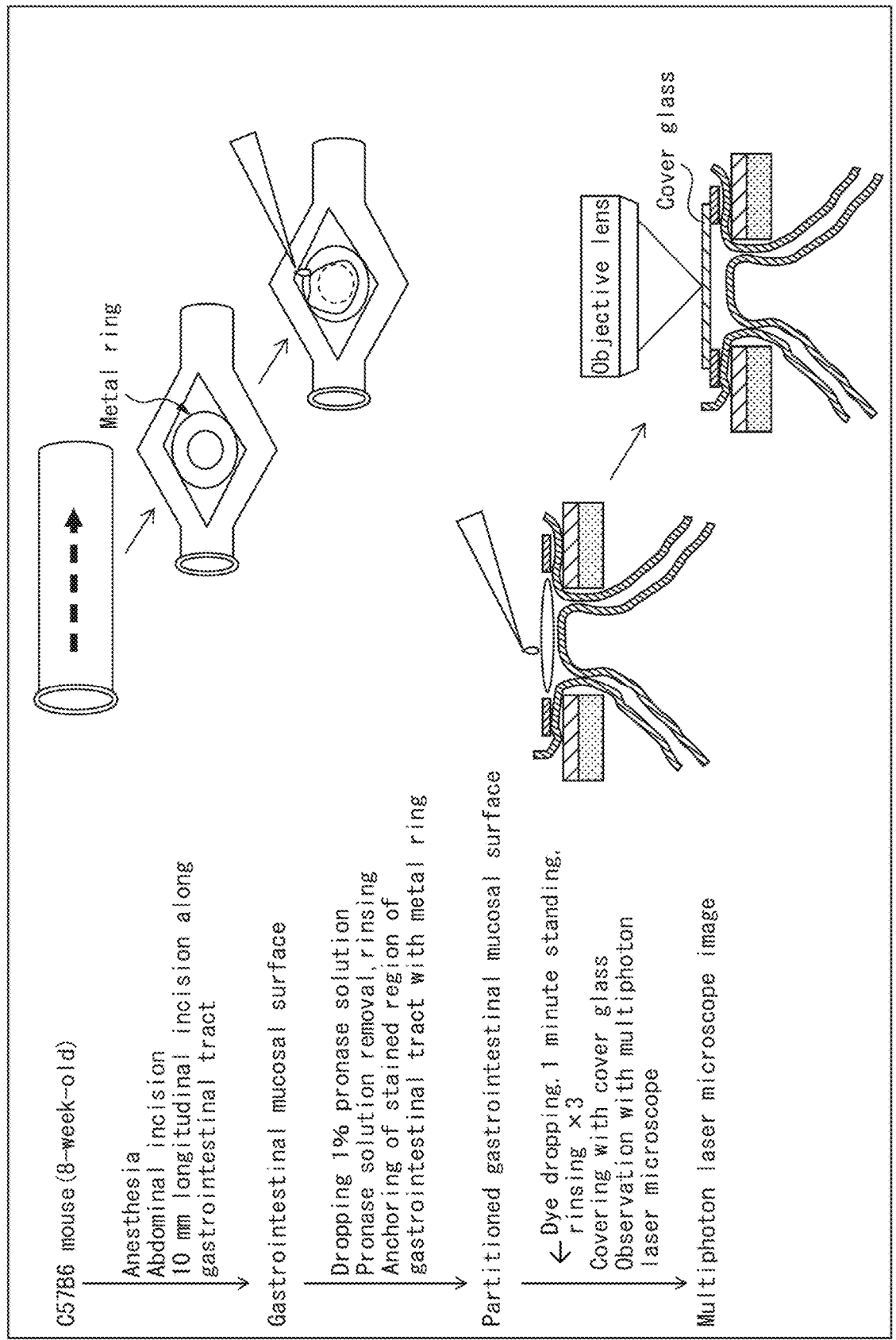
FIG. 32 is a flow chart illustrating the steps of evaluating stainability of a dye compound.

In order to avoid drying of the mucosal surface, a curcumin stock solution or sulfuretin stock solution diluted with physiological saline (PBS) (see Table 1 for the dilution factors) was added dropwise onto the pronase-treated mucosal surface, and after allowing it to stand for 1 minute, it was rinsed 3 times with PBS, a cover glass was placed over the metal ring, and the objective lens of a multiphoton laser microscope (FV1000 MPE by Olympus Corp.) was brought near to the top of the cover glass for image observation. FIG. 32 is a drawing for illustration of a stainability evaluation step for the aforementioned dye compounds.

The conditions used to evaluate the dye compounds, and the evaluation results, are shown in the following tables.

TABLE 4

| | Exo vivo Large intestine | Small intestine | Stomach | Esophageal | Excitation wavelength | Concentration used |
|---|---|---|---|---|---|---|
| Curcumin (turmeric extract) | VG 0.05% | VG 0.05% | VG (Epithelium and glands) | G | 780-800 nm | 0.50% |
| Curcumin (pure) | VG 0.01 mg/ml | VG 0.1 mg/ml | | | 780-800 nm | |
| Sulfuretin | VG Blood vessels powerfully stained at 1 mg/ml, 0.1 mg/ml | VG 0.1 mg/ml | G Epithelium: G | G | 780-800 nm | 1 mg/ml |
| Erythrosine (Red #3) | F | VG 0.1 mg/ml | | | 800 nm | 0.1 mg/ml |
| Acid Red (Red #106) | VG 0.1 mg/ml, Cell membrane. Appeared as goblet cells. Blood vessels visible even at low concentration. | VG 0.1 mg/ml Appeared as muscle layer. | | | 840 nm | 0.1 mg/ml |
| Epigallocatechin gallate | G | G | | | 760 nm | 0.1 mg/ml |

| | Stock concentration | Stock solvent | LD50 | | |
|---|---|---|---|---|---|
| Curcumin (turmeric extract) | | | 2000 mg/kg | Mouse | Oral |
| Curcumin (pure) | 100 mg/ml | 45% EtOH/ glycerol | 2000 mg/kg | Mouse | Oral |
| Sulfuretin | 100 mg/ml | DMSO | 300 mg/kg | Mouse | Oral |
| Erythrosine (Red #3) | | PBS | 6800 mg/kg | Mouse | Oral |
| Acid Red (Red #106) | | PBS | >20000 mg/kg | Mouse | Oral |
| Epigallocatechin gallate | 100 mg/ml | DMSO | 2170 mg/kg | Mouse | Oral |

VG: Image having ideal brightness and contrast for image diagnosis; G: Image having sufficient brightness and contrast for image diagnosis, P: Image having insufficient brightness and contrast for image diagnosis; F: State between G and P.

In observation by multiphoton laser microscopy, the photon doses necessary to obtain fluorescent images when the mucosal surfaces were coated with curcumin and sulfuretin were sufficient at 3% and 4% compared to non-staining, respectively (results not shown).

2. Comparison of Staining Patterns in Normal Site and Cancer Tumor Site

Figure 22:
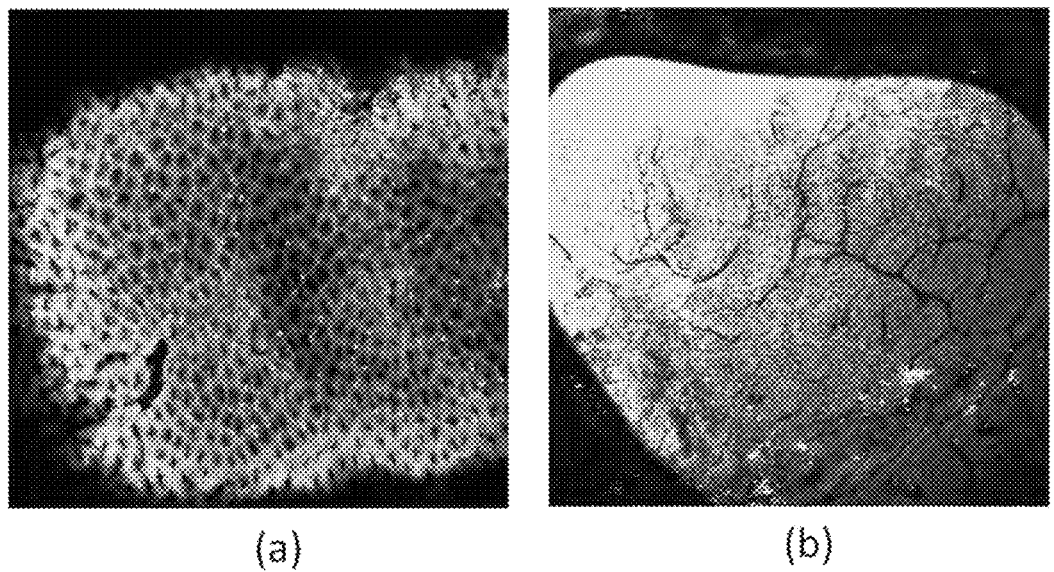
FIG. 22 shows a pair of multiphoton laser microscope photographs, a normal large intestine mucosa (a) and a colon tumor site (b), stained with curcumin.

Next, the large intestine of a mouse confirmed to have fungoid processes (cancer) with a diameter of 2 to 4 millimeters on the large intestinal mucosal surface was stained (without pronase treatment), and curcumin and sulfuretin both stained the cancer lesion site significantly more intensely than the normal mucosa. The results of staining with curcumin are shown in FIG. 22 (10× objective: Z stack image).

Figure 23:
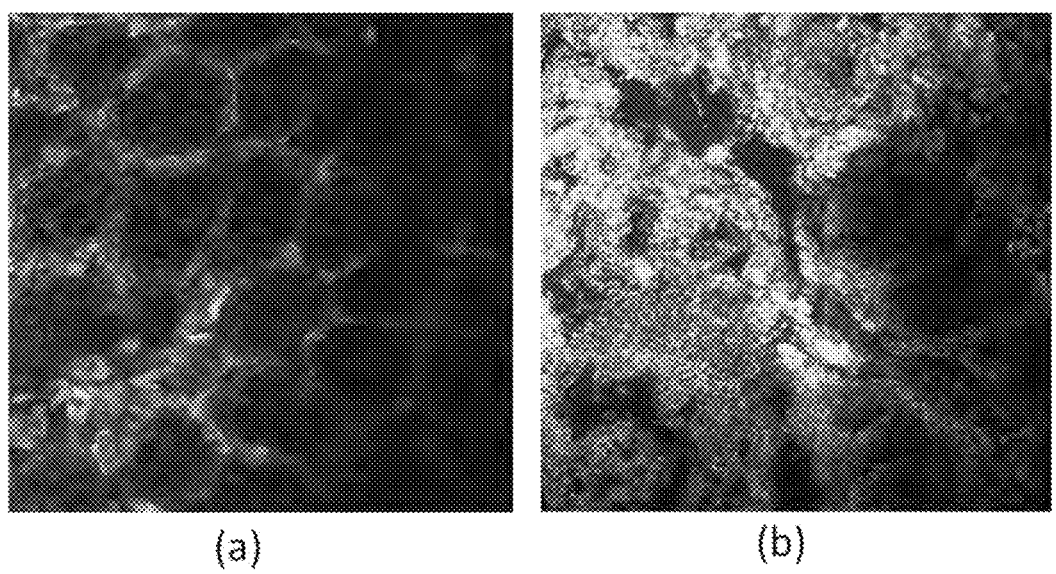
FIG. 23 shows a pair of multiphoton laser microscope photographs, a normal large intestine mucosa (a) and a colon tumor site (b), stained with curcumin after treatment with 1% pronase.

Also, FIG. 23 shows a curcumin staining pattern after 15 minutes treatment with 1% pronase MS (high-power magnification, 25× objective). Surprisingly, curcumin clearly stained the cancer lesion site significantly more intensely than the normal mucosa, regardless of whether or not the mucosal surface had been pronase treated. Similar results were obtained for sulfuretin as well (results not shown). Both of the staining photographs of the normal site and cancer tumor site were taken under the same conditions.

While it is not our intent to be constrained by theory, it is possible that the reason for intense staining of the cancer lesion site is that in cancer lesion sites the intercellular adhesion is weak and many gaps are present between the cells, compared to normal mucosa where cellular adhesion is strong and there are virtually no intercellular gaps, and therefore the dye easily remained in the gaps. A second conceivable possibility is that cancer cells, which undergo rapid cell division, have higher uptake activity for extracellular lipophilic substances (most dyes having the nature of dissolving well in oils), compared to normal cells. The results are not shown, but the property of the dye of staining cancer cells more intensely than normal cells upon application to the mucosal epithelial surface was also confirmed with monolayer culture cells.

Figure 24:
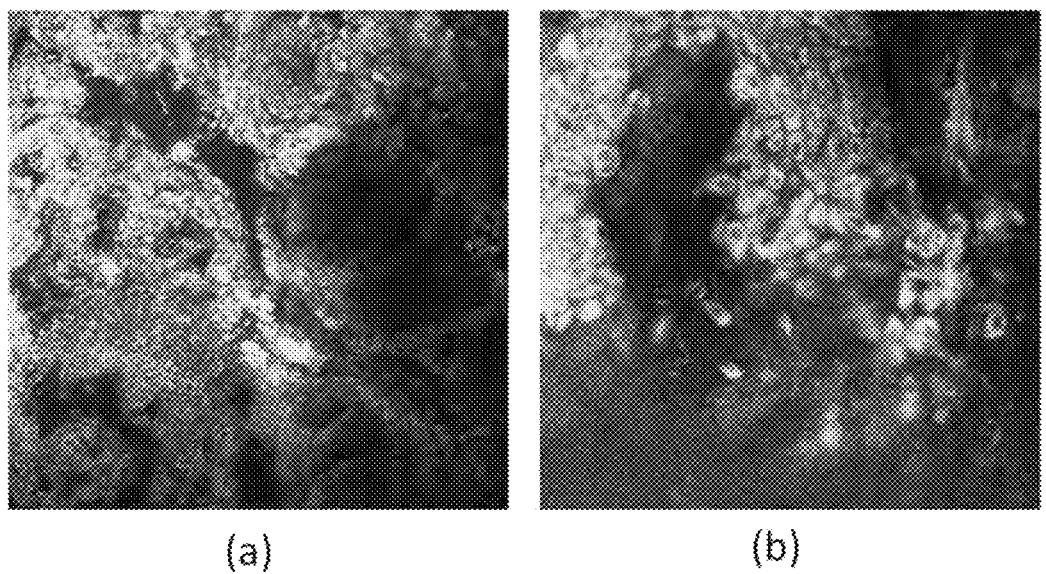
FIG. 24 is a pair of multiphoton laser microscope photographs showing structural atypia (a) and cellular atypia (b), of a colon cancer stained with curcumin.

In addition, a multiphoton laser microscope image was taken of the mouse colon cancer and it was confirmed to have atypia as a morphological characteristic of the cancer type. The results obtained using curcumin are shown in FIG. 24. Based on the results, it was possible to confirm the structural atypia and cellular atypia necessary for detection of cancer. In FIG. 24(a), the cell population is not orderly arranged on the basal membrane and a glandular structure is not formed, thus confirming structural atypia. In FIG. 3(b), on the other hand, cellular atypia was confirmed, such as disparate sizes of individual cells, large nuclei, non-uniform locations, polar non-homogeneity and cell adhesion dissociation.

3. Further Examination of Staining Property

Figure 25:
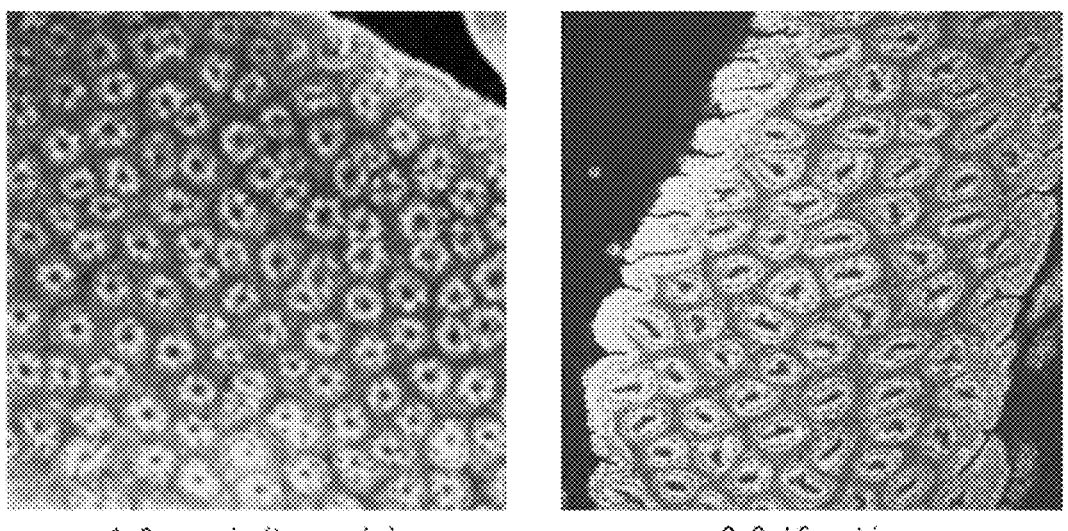
FIG. 25 is a pair of high-contrast multiphoton laser microscope images taken with curcumin staining and sulfuretin staining.

In addition, when curcumin and sulfuretin were applied onto the mucosal surface of mouse large intestine they were strongly excited by a multiphoton laser and provided bright images. The results are shown in FIG. 25. The procedure from administration of the dye compound to observation was conducted as described above under "Evaluation of stainability" (same hereunder). The concentration of dye administered to the mucosal surface was 5 mg/ml for curcumin and 1 mg/ml for sulfuretin.

Figure 26A:
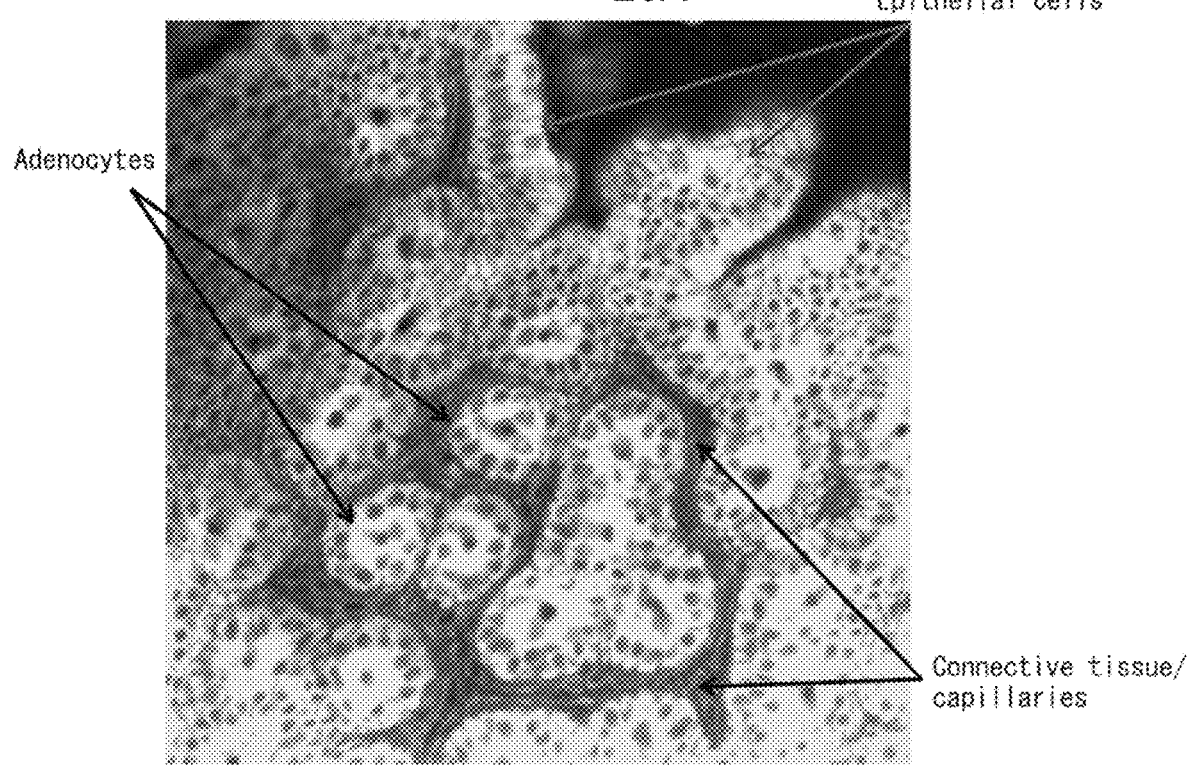
FIG. 26A is a multiphoton laser microscope photograph of epithelial cells/adenocytes preferentially stained with curcumin.
Figure 26B:
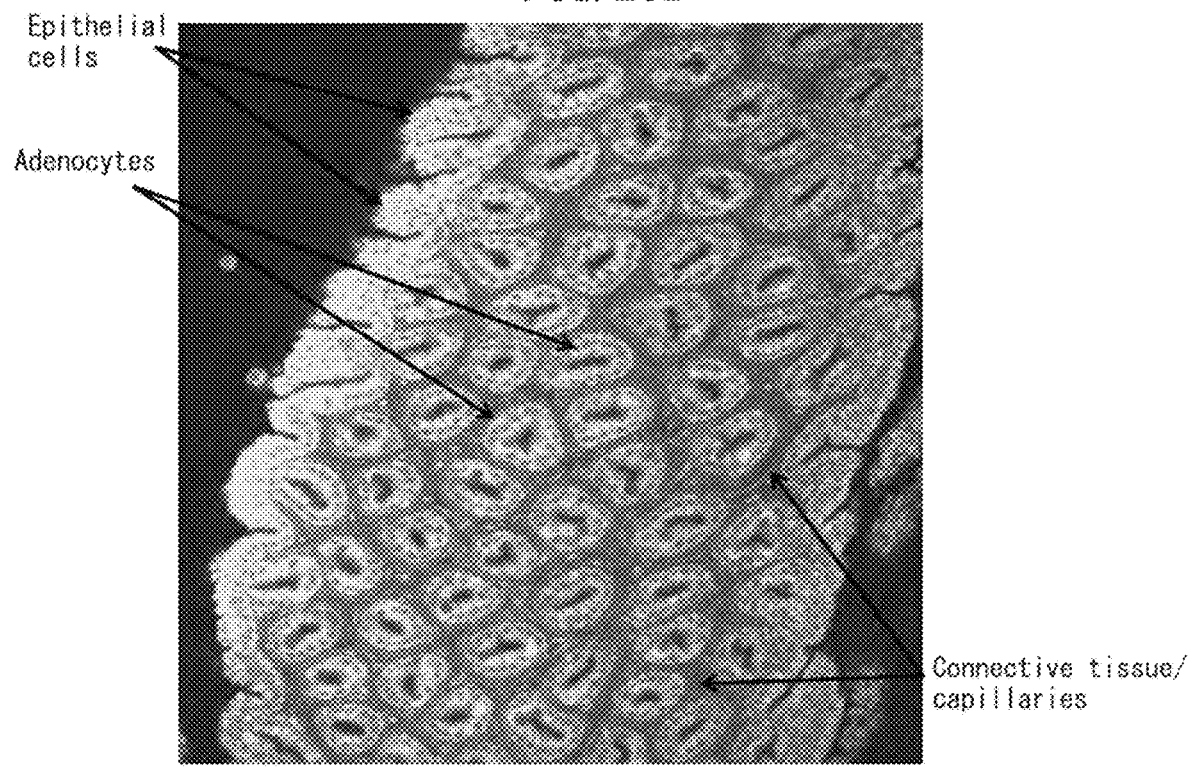
FIG. 26B is a multiphoton laser microscope photograph of epithelial cells/adenocytes preferentially stained with sulfuretin.

Moreover, the property of curcumin and sulfuretin to preferentially stain epithelial cells/adenocytes was also confirmed. The results are shown in FIGS. 26A and B. These dyes intensely stained epithelial cells/adenocytes and faintly stained connective tissue/capillaries.

4. Elimination of Cancer Cells by Laser Irradiation

Figure 27A:
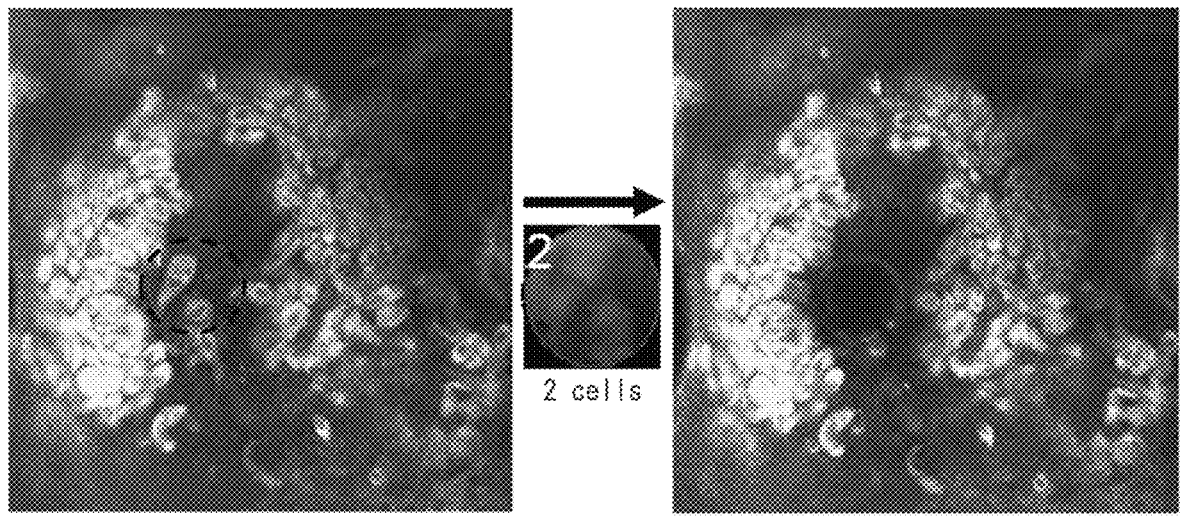
FIG. 27A is a pair of multiphoton laser microscope photographs showing a process in which only two cancer cells were eliminated by laser irradiation (power: 45%, irradiation time: 2 seconds).
Figure 27B:
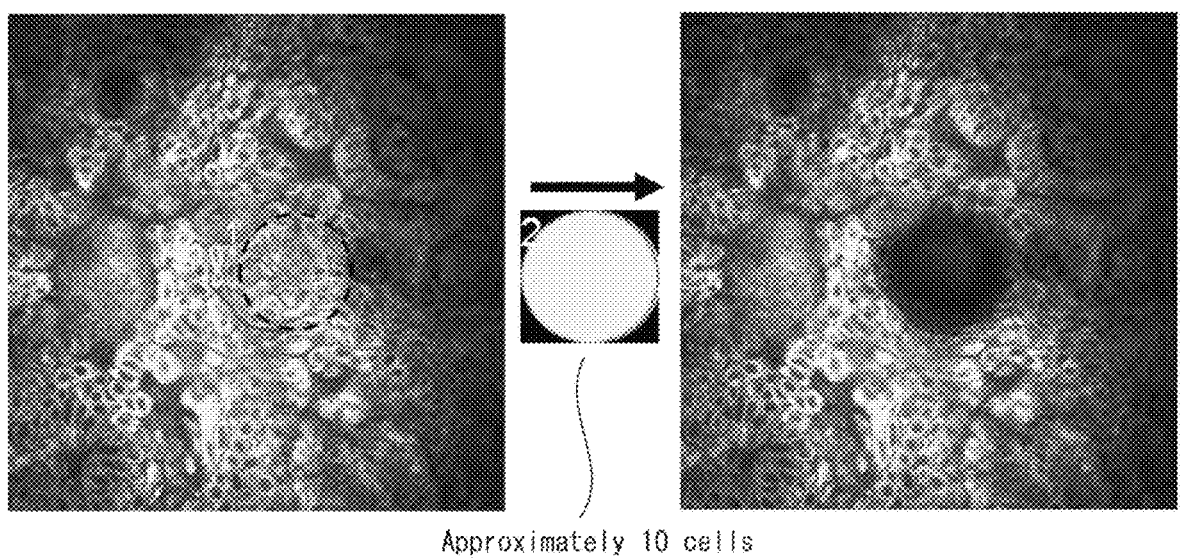
FIG. 27B is a pair of multiphoton laser microscope photographs showing a process in which only 10 cancer cells were eliminated by laser irradiation (power: 45%, irradiation time: 10 seconds).

Among the cells stained by the procedure described above, the cancer cells were eliminated in a pinpoint manner by multiphoton laser irradiation. The cancer cells to be eliminated were pinpointed directly using the coordinate axes of the image used for detection. The irradiation conditions were a laser power of approximately 45% and an irradiation time of 2 to 10 seconds. The results are shown in FIGS. 27A and B.

The conditions were then changed to a laser power of 100% and an irradiation time of 20 seconds, and cancer cells with 0.5 millimeter diameters, detected on the mucosal surface of the gastrointestinal tract, were successfully completely eliminated (FIG. 28). Also, although the results are not shown, it was possible to destroy the cell membranes and eliminate the cancer cells even by laser irradiation on portions of the cell membranes with a lower light dose.

In the multiphoton laser microscope photograph taken at a laser power of 82% of mouse bladder epithelial cells without curcumin staining, with autologous fluorescence of the cells (FIG. 29A), the image was dark and the contrast was low, making the cellular image insufficient for diagnosis, but in the multiphoton laser microscope photograph taken at a laser power of 3%, with curcumin staining of mouse bladder epithelial cells (FIG. 29B), an image with sufficient brightness and contrast for diagnosis was obtained.

In the multiphoton laser microscope photograph taken at a laser power of 82% of mouse tracheal epithelial cells without curcumin staining, with autologous fluorescence of the cells (FIG. 30(a)), the image was dark and the contrast was low, making the cellular image insufficient for diagnosis, but in the multiphoton laser microscope photograph taken at a laser power of 3%, with curcumin staining of mouse tracheal epithelial cells (FIG. 30(b)), an image with sufficient brightness and contrast for diagnosis was obtained.

Similar staining also occurred with surgically excised fresh human gastric mucosa. A multiphoton laser microscope photograph taken of a human normal gastric mucosa site stained with curcumin, with a laser power of 1%, is shown in FIG. 31(a). In this photograph, the circularly arranged normal epithelial cells are stained, forming circular structures of essentially uniform size. The centers of the circular structures are the exits of the fundic glands. It was thus possible to confirm the characteristic of normal tissue whereby epithelial cells arrange in a circular manner without disparate sizes. A multiphoton laser microscope photograph taken of a stomach cancer site in fresh human gastric mucosa obtained in the same manner and stained with curcumin, with a laser power of 1%, is shown in FIG. 31(b). In this photograph, cancer cells are stained, the sizes of the cells being notably disparate and the cell arrangements being irregular. The blackened elliptical portions in each cell are the nuclei. It was thus possible to confirm the characteristic of cancer tissue whereby epithelial cells arrange in an irregular manner without notably disparate sizes.

INDUSTRIAL APPLICABILITY

With the vital stain of the invention it is possible to notably reduce photodamage including genetic damage and thermal damage to cells by ultraviolet rays, compared to conventional observation of autologous fluorescence under multiphoton laser microscopy, and to accomplish imaging of cellular tissue morphology with high contrast. Thus, a vital stain of the invention can be suitably used for histopathological diagnosis of a wide range of epithelial cells/adenocytes, connective tissue/capillary cells and the like, including those in the digestive organs.

EXPLANATION OF SYMBOLS

11 Multiphoton laser diagnosis and treatment apparatus
13 Laser oscillator
17 Two-dimensional scanner
19 Dichroic mirror
21 Objective lens 23 Focal depth controller
25 Photodetector
27 Fluorescent image generating device
29 Monitor
31 Controller
33 Operating controller
35 Diagnostic pulse intensity setting adjuster
37 Treatment pulse intensity setting adjuster
39 Irradiation range setting adjuster
41 Irradiation time setting adjuster
43 Laser irradiation head
45 Patient immobilizing platform
47 Moving apparatus
49 Endoscope
50 Optical system
51 Shield member
52 Tissue
53 Space
54 Vent hole
55 Vent hole
56 Fluid supply inlet
57 Fluid drainage outlet
61 Shield member-equipped endoscope
62 Tip section
63 Insertion member
64 Forceps hole
65 Forceps
66 Angle knob actuator
67 Eyepiece
68 Eyepiece lens
69 Air supply and water supply actuator
70 Aspiration actuator
71 Connector
72 Light guide

What is claimed is:
1. An in vivo method of detecting cancer cells, using a stain, the method of detecting cancer cells comprising:
   1) applying the stain to the cells in vivo, and
   2) distinguishing normal cells and cancer cells based on a difference in cell staining intensity, using a multiphoton laser microscope,
   wherein said stain specifically stains cancer cells in contrast to normal cells, and wherein the stain comprises curcumin.

* * * * *